United States Patent
Cannas et al.

(10) Patent No.: US 10,414,875 B2
(45) Date of Patent: Sep. 17, 2019

(54) CATALYST CONTAINING GUANIDINE GROUPS

(71) Applicant: SIKA TECHNOLOGY AG, Baar (CH)

(72) Inventors: Rita Cannas, Dübendorf (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/572,331

(22) PCT Filed: May 10, 2016

(86) PCT No.: PCT/EP2016/060478
§ 371 (c)(1),
(2) Date: Nov. 7, 2017

(87) PCT Pub. No.: WO2016/180840
PCT Pub. Date: Nov. 17, 2016

(65) Prior Publication Data
US 2018/0148545 A1    May 31, 2018

(30) Foreign Application Priority Data
May 11, 2015 (EP) .................................. 15167147

(51) Int. Cl.
*C08G 77/46* (2006.01)
*C07C 277/08* (2006.01)
*C08K 5/31* (2006.01)
*C08G 65/336* (2006.01)
*C08J 3/24* (2006.01)
*C09D 183/12* (2006.01)
*C09J 183/12* (2006.01)

(52) U.S. Cl.
CPC ............ *C08G 77/46* (2013.01); *C07C 277/08* (2013.01); *C08G 65/336* (2013.01); *C08J 3/24* (2013.01); *C08K 5/31* (2013.01); *C09D 183/12* (2013.01); *C09J 183/12* (2013.01); *C07C 2601/14* (2017.05); *C08J 2383/12* (2013.01)

(58) Field of Classification Search
None
See application file for complete search history.

(56) References Cited

U.S. PATENT DOCUMENTS

| 4,732,910 A * | 3/1988 | Yaginuma ............... C12P 17/02 514/475 |
| 2005/0249692 A1* | 11/2005 | Hiwatashi ............ A61K 8/8152 424/70.16 |
| 2010/0136647 A1* | 6/2010 | Algotsson ............ C12N 5/0075 435/179 |
| 2011/0046299 A1* | 2/2011 | Maliverney ........... C07F 7/1804 524/588 |
| 2013/0190469 A1 | 7/2013 | Barrandon et al. |
| 2016/0289237 A1* | 10/2016 | Kumano ............... C07D 487/04 |

FOREIGN PATENT DOCUMENTS

WO    2015/026687 A1    2/2015

OTHER PUBLICATIONS

Jul. 8, 2016 International Search Report issued in International Patent Application No. PCT/EP2016/060478.
Nov. 23, 2017 International Preliminary Report on Patentability issued in International Application No. PCT/EP2016/060478.
Apr. 23, 2019 Office Action issued in Chinese Application No. 201680034285.8.

* cited by examiner

*Primary Examiner* — Robert S Loewe
(74) *Attorney, Agent, or Firm* — Oliff PLC

(57) ABSTRACT

The use of a catalyst of the formula (I) for the crosslinking of a curable composition. The catalyst of the formula (I) contains at least one aliphatic guanidine group. It is substantially odorless and nonvolatile at room temperature and accelerates the crosslinking of curable compositions very efficiently, without impairing the storage stability thereof. It is particularly suitable for compositions based on polymers containing silane groups, where it has very good compatibility, as a result of which such compositions do not have a tendency to separation or migration or evaporation of the catalyst.

15 Claims, No Drawings

CATALYST CONTAINING GUANIDINE GROUPS

TECHNICAL FIELD

The invention relates to catalysts for curable compositions, especially for compositions containing silane groups.

STATE OF THE ART

Curable compositions play a significant role in many industrial applications, for example as adhesives, sealants or coatings. The curing thereof is brought about by crosslinking reactions which proceed via free or latent reactive groups, for example isocyanate groups, epoxide groups, hydroxyl groups, amino groups or silane groups, wherein these react with themselves or one another following a mixing operation or through heating or through contact with moisture, and hence bind the formation components present in the composition covalently to form a polymeric network. Acceleration of such crosslinking reactions is frequently accomplished using catalysts. These are very often substances of toxicological concern which constitute a potential hazard to users and the environment, especially after the curing of the composition, if the catalyst or degradation products thereof are released by outgassing, migration or washing-out.

Compositions curable at room temperature that are based on polymers containing silane groups are confronted with this problem to a significant degree. Polymers containing silane groups here are especially polyorganosiloxanes, which are commonly referred to as "silicones" or "silicone rubbers", and organic polymers containing silane groups, which are also referred to as "silane-functional polymers", "silane-modified polymers" (SMP) or "silane-terminated polymers" (STP). The crosslinking thereof proceeds via the condensation of silanol groups to form siloxane bonds and is conventionally catalyzed by means of organotin compounds such as dialkyltin(IV) carboxylates in particular. These are notable for very high activity in relation to the silanol condensation and are very hydrolysis-resistant, but they are harmful to health and a severe water pollution hazard. They are often combined with further catalysts, mainly basic compounds, such as amines in particular, which specifically accelerate the preceding hydrolysis of the silane groups. Because greater weight is being given to EHS aspects by professional organizations and users and because of stricter government regulation, there have been increased efforts for some time to replace organotin compounds with other catalysts of lower toxicity. For instance, organotitanates, -zirconates and -aluminates have been described as alternative metal catalysts. However, these usually have lower catalytic activity in relation to the silanol condensation and bring about much slower crosslinking. Because of their lack of hydrolysis stability, they can lose a large part of their activity in the course of storage of the composition as a result of residual moisture in the ingredients, which causes the curing to slow significantly or stop entirely.

A further known alternative to organotin compounds is highly basic nitrogen compounds from the class of the amidines and guanidines, which can be used in combination with the metal catalysts mentioned or else alone. However, many of the commonly used amidine and guanidine catalysts, such as, in particular, 1,8-diazabicyclo[5.4.0]undec-7-ene (DBU) and 1,1,3,3-tetramethylguanidine (TMG), are volatile and odorous substances that are likewise harmful to health and hazardous to the environment. Moreover, they have a tendency to migrate because of low compatibility in the composition and hence to cause separation, exudation or substrate soiling. The described use of aromatic amidines and guanidines that are solid at room temperature provides a remedy here, but requires the use of suitable solvents and brings losses in catalytic activity and hence crosslinking rate.

SUMMARY OF THE INVENTION

It is therefore an object of the present invention to provide a catalyst for the crosslinking of curable compositions, especially compositions containing silane groups, which has a high catalytic activity for the crosslinking reaction and hence enables rapid curing of the composition applied, and also have a high selectivity for this crosslinking reaction and hence does not unduly impair the storage stability of the composition. Furthermore, the catalyst is to have a low vapor pressure and high compatibility with the composition, such that it has no tendency either to separate or migrate or to evaporate, and is to have minimum odor and low toxicity.

This object is achieved by the use of a catalyst of the formula (I) as claimed in claim 1. The catalyst of the formula (I) contains an aliphatic guanidine group and exhibits high catalytic activity, whereas aromatic guanidines are barely catalytically active or completely catalytically inactive. By contrast with many catalysts having aliphatic amidine or guanidine groups that are known from the prior art, the catalyst of the formula (I) is substantially odorless and nonvolatile at room temperature. It exhibits high catalytic activity coupled with good selectivity, especially in compositions based on polymers containing silane groups. This is particularly surprising, given that, on the basis of its relatively high molecular weight and the strong intermolecular interactions via hydrogen bonds, reduced activity would be expected as compared with smaller, less polar and hence more mobile guanidines.

With these properties, the catalyst of the formula (I) is particularly suitable for use in compositions based on polymers containing silane groups, where, as sole catalyst or in combination with further catalysts, it enables rapid curing to give a mechanically high-quality and durable material, without impairing the storability of the uncured composition. Both before and after curing, it has excellent compatibility with the composition and does not have any tendency either to separate or to migrate, by contrast with many similar compositions comprising amidine or guanidine catalysts according to the prior art, where catalyst-related migration effects play a major role. It enables low-emission and low-odor products which have neither greasy nor tacky surfaces, nor do they cause substrate soiling. Finally, the catalyst of the formula (I) is preparable in a surprisingly simple process without auxiliaries from commercially available, inexpensive starting materials.

Further aspects of the invention are the subject of further independent claims. Particularly preferred embodiments of the invention are the subject of the dependent claims.

Ways of Executing the Invention

The invention provides for the use of a catalyst of the formula (I)

where
p is an integer from 1 to 6 and r is an integer from 0 to 5, where (p+r) is an integer from 1 to 6, L is
- a (p+r)-valent hydrocarbyl radical having a mean molecular weight in the range from 14 to 20'000 g/mol, optionally having heteroatoms, especially oxygen or nitrogen or silicon in the form of ether, tertiary amino, ester, amide, urethane, urea, uretdione, isocyanurate, biuret, allophanate, uretonimine, iminooxadiazinedione, oxadiazinetrione or alkoxysilane groups,
- or is a (p+r+1)-valent hydrocarbyl radical having 4 to 12 carbon atoms, which together with Q' forms an optionally substituted 5- or 6-membered ring,
- or is a covalent bond,
- or is a hydrogen radical, Q is a reactive group selected from epoxide, aziridine, carbonate, carboxylic anhydride, carboxylic acid, carboxylic ester, lactone, carbonyl chloride, ketone, aldehyde, 1,3-diketone, 1,3-keto ester, 1,3-keto amide, cyanate, thiocyanate, isocyanate, isothiocyanate, (meth)acrylate, (meth)acrylamide, (meth)acrylonitrile, maleate, maleamide, maleimide, fumarate, fumaramide, itaconate, itaconamide, crotonate and crotonamide, Q' is a di- or trivalent connecting unit formed from the reaction of Q with HX, Y is N or X, where X is O or S or $NR^3$ where $R^3$ is a hydrogen radical or is an alkyl or cycloalkyl or aralkyl radical which has 1 to 8 carbon atoms and optionally contains a tertiary amino group or a guanidine group, A is a divalent hydrocarbyl radical which has 2 to 30 carbon atoms and optionally contains unsaturated components and optionally ether oxygen or secondary or tertiary amine nitrogen, where A together with $R^3$ may also be a trivalent hydrocarbyl radical which has 5 to 10 carbon atoms and optionally contains a tertiary amine nitrogen, and Z is a guanidine group which is bonded via a nitrogen atom and does not contain any nitrogen atom which is bonded directly to an aromatic ring or is part of a heteroaromatic ring system, for example imidazole or pyrimidine, for the crosslinking of a curable composition.

In the present document, the term "silane group" refers to a silyl group which is bonded to an organic radical or to a polyorganosiloxane radical and has one to three, especially two or three, hydrolyzable substituents on the silicon atom. Particularly useful hydrolyzable substituents are alkoxy radicals. These silane groups are also referred to as "alkoxysilane groups". Silane groups may also be in partly or fully hydrolyzed form.

"Hydroxysilane", "isocyanatosilane", "aminosilane" and "mercaptosilane" refer respectively to organoalkoxysilanes having one or more hydroxyl, isocyanato, amino or mercapto groups on the organic radical in addition to the silane group.

"Primary amino group" and "primary amine nitrogen" refer respectively to an $NH_2$ group and the nitrogen atom thereof that is bonded to an organic radical, and "secondary amino group" and "secondary amine nitrogen" refer respectively to an NH group and the nitrogen atom thereof that is bonded to two organic radicals which may also together be part of a ring, and "tertiary amino group" and "tertiary amine nitrogen" refer respectively to an N group and the nitrogen atom thereof that is bonded to three organic radicals, two or three of which together may also be part of one or more rings.

Substance names beginning with "poly", such as polyol or polyisocyanate, refer to substances containing, in a formal sense, two or more of the functional groups that occur in their name per molecule.

The term "organic polymer" encompasses a collective of macromolecules that are chemically homogeneous but differ in relation to degree of polymerization, molar mass and chain length, which has been prepared by a poly reaction (polymerization, polyaddition, polycondensation) and has a majority of carbon atoms in the polymer backbone, and reaction products of such a collective of macromolecules. Polymers having a polyorganosiloxane backbone (commonly referred to as "silicones") are not organic polymers in the context of the present document.

The term "polyether containing silane groups" also encompasses organic polymers which contain silane groups and which, in addition to polyether units, may also contain urethane groups, urea groups or thiourethane groups. Such polyethers containing silane groups may also be referred to as "polyurethanes containing silane groups".

"Molecular weight" is understood in the present document to mean the molar mass (in grams per mole) of a molecule or part of a molecule, also referred to as "radical". "Mean molecular weight" is understood to mean the number-average $M_n$ of an oligomeric or polymeric mixture of molecules or radicals, which is typically determined by means of gel permeation chromatography (GPC) against polystyrene as standard.

"Storage-stable" or "storable" refers to a substance or composition when it can be stored at room temperature in a suitable container over a prolonged period, typically at least 3 months up to 6 months or more, without any change in its application or use properties, especially in the viscosity and crosslinking rate, to a degree of relevance for the use thereof as a result of the storage.

A dotted line in the formulae in this document in each case represents the bond between a substituent and the corresponding molecular radical.

"Room temperature" refers to a temperature of about 23° C.

If L is a covalent bond, the catalyst of the formula (I) has either the formula Q-Q'-Y-A-Z or formula Z-A-Y-Q'-Q'-Y-A-Z.

Preferably, A has 2 to 20 carbon atoms.

More preferably, A is either selected from the group consisting of 1,2-ethylene, 1,2-propylene, 1,3-propylene, 1,3-pentylene, 1,1-dimethyl-1,2-ethyl, 1,5-pentylene, 2-methyl-1,5-pentylene, 1,6-hexylene, 2,2(4),4-trimethyl-1,6-hexamethylene, 1,8-octylene, 1,10-decylene, 1,12-dodecylene, (1,5,5-trimethylcyclohexan-1-yl)methane-1,3, 1,3-cyclohexylenebis(methylene), 1,4-cyclohexylenebis (methylene), 1,3-phenylenebis(methylene), 2- and/or 4-methyl-1,3-cyclohexylene, N-methyl-4-aza-1,7-heptylene, 3-oxa-1,5-pentylene, 3,6-dioxa-1,8-octylene, 4,7-dioxa-1,10-decylene and a polyoxypropylene radical having a mean molecular weight in the range from about 200 to 250 g/mol, or A together with $R^3$ including the nitrogen atom of X is a radical selected from the group consisting of piperidin-4-ylmethyl, 2-(piperidin-4-yl)ethyl and 2-piperazinoethyl.

If A together with $R^3$ including the nitrogen atom of X is piperidin-4-ylmethyl or 2-(piperidin-4-yl)ethyl or 2-piperazinoethyl, the catalyst of the formula (I) has the formula

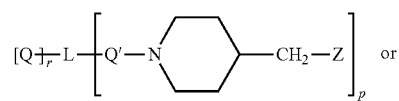 or

-continued

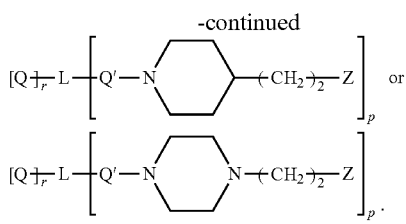

Y is preferably N or O or $NR^3$.

$R^3$ is preferably a hydrogen radical.

$R^3$ is further preferably an alkyl or cycloalkyl radical having 1 to 8 carbon atoms.

$R^3$ is further preferably a radical of the formula

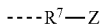

where $R^7$ is an optionally branched alkylene radical having 2 to 6 carbon atoms, especially 1,2-ethylene, 1,3-propylene or 1,6-hexylene, and Z has the definitions given.

$R^3$ is further preferably an N,N-dimethylaminopropyl radical.

$R^3$ is further preferably, together with A and with inclusion of the nitrogen atom of X, piperidin-4-ylmethyl or 2-(piperidin-4-yl)ethyl or 2-piperazinoethyl.

Z is preferably

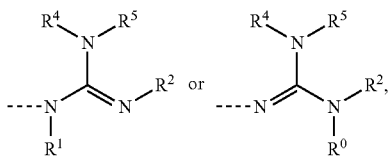

where $R^0$ and $R^1$ are independently a hydrogen radical or an alkyl or cycloalkyl or aralkyl radical having 1 to 8 carbon atoms, $R^2$ is a hydrogen radical or an alkyl, cycloalkyl or aralkyl radical which has 1 to 18 carbon atoms and optionally contains ether oxygen or tertiary amine nitrogen, $R^4$ and $R^5$ are each independently a hydrogen radical or an alkyl, cycloalkyl or aralkyl radical which has 1 to 18 carbon atoms and optionally contains an ether oxygen or a tertiary amine nitrogen, where $R^2$ and $R^0$ together may also be an alkylene radical which has 3 to 6 carbon atoms and optionally contains an ether oxygen or a tertiary amine nitrogen, $R^4$ and $R^5$ together may also be an alkylene radical which has 4 to 7 carbon atoms and optionally contains an ether oxygen or a tertiary amine nitrogen, and $R^2$ and $R^5$ together may also be an alkylene radical having 2 to 12 carbon atoms.

$R^1$ and $R^0$ are preferably each independently a hydrogen radical or an alkyl radical having 1 to 4 carbon atoms, especially a hydrogen radical.

$R^2$ is preferably a hydrogen radical or an alkyl, cycloalkyl or aralkyl radical which has 1 to 12 carbon atoms, especially 1 to 8 carbon atoms, and optionally contains ether oxygen or tertiary amine nitrogen.

$R^4$ and $R^5$ are preferably each independently a hydrogen radical or an alkyl, cycloalkyl or aralkyl radical which has 1 to 12 carbon atoms and optionally contains an oxygen atom or a nitrogen atom.

Further preferably, $R^4$ and $R^5$ together are an alkylene radical which has 4 to 7 carbon atoms and optionally contains an oxygen atom or a nitrogen atom.

$R^1$ and $R^0$ are preferably each independently a hydrogen radical or an alkyl radical having 1 to 4 carbon atoms, especially a hydrogen radical.

$R^2$ is preferably a hydrogen radical or an alkyl, cycloalkyl or aralkyl radical which has 1 to 12 carbon atoms, especially 1 to 8 carbon atoms, and optionally contains ether oxygen or tertiary amine nitrogen.

$R^4$ and $R^5$ are preferably each independently a hydrogen radical or an alkyl, cycloalkyl or aralkyl radical which has 1 to 12 carbon atoms and optionally contains an oxygen atom or a nitrogen atom.

Further preferably, $R^4$ and $R^5$ together are an alkylene radical which has 4 to 7 carbon atoms and optionally contains an oxygen atom or a nitrogen atom.

$R^4$ is more preferably a hydrogen radical.

$R^5$ is more preferably an alkyl, cycloalkyl or aralkyl radical which has 1 to 12 carbon atoms, especially 1 to 8 carbon atoms, and optionally contains an ether oxygen or tertiary amine nitrogen.

More preferably, Z is

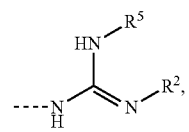

where $R^2$ and $R^5$ have the definitions already given.

More preferably, $R^2$ and $R^5$ are each independently ethyl, isopropyl, tert-butyl, 3-(dimethylamino)propyl or cyclohexyl, especially isopropyl or cyclohexyl. Such a catalyst of the formula (I) has, as $R^3$, preferably a hydrogen radical or an alkyl or cycloalkyl radical having 1 to 8 carbon atoms or a radical of the formula

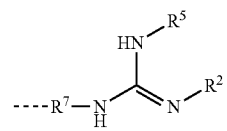

where $R^7$, $R^2$ and $R^5$ have the definitions already given, or an N,N-dimethylaminopropyl radical.

Q is preferably epoxide, carbonate, carboxylic anhydride, carboxylic ester, lactone, ketone, aldehyde, 1,3-diketone, 1,3-keto ester, 1,3-keto amide, cyanate, isocyanate, acrylate, methacrylate, acrylamide, methacrylamide, maleate, maleimide, fumarate or itaconate.

Q is more preferably epoxide, carbonate, carboxylic ester, lactone, ketone, aldehyde, 1,3-diketone, 1,3-keto ester, isocyanate, acrylate or methacrylate. The epoxide group preferably takes the form of a glycidyl group, especially of a glycidyloxy group.

The aziridine group is preferably an N-aziridinyl group.

Q' is preferably selected from the group consisting of

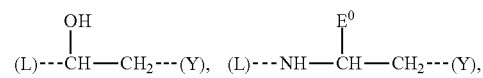

-continued

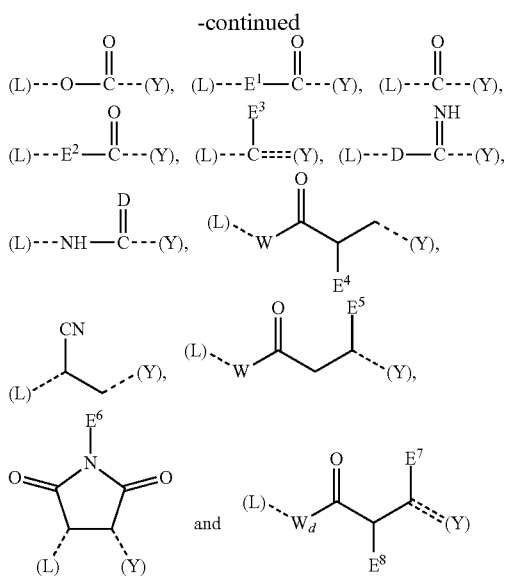

where

D is O or S,

W is O or $NR^6$ where $R^6$ is a hydrogen radical or is a monovalent hydrocarbyl radical having 1 to 8 carbon atoms, $E^0$ is a hydrogen radical or is a methyl radical, $E^1$ is a carboxyl-substituted alkylene, alkenediyl or phenylene radical having 2 to 8 carbon atoms, $E^2$ is a hydroxyalkylene radical having 2 to 5 carbon atoms or is an O-bonded hydroxyalkyleneoxy radical having 2 or 3 carbon atoms, $E^3$ is a hydrogen radical or is a monovalent hydrocarbyl radical which has 1 to 6 carbon atoms and optionally has heteroatoms in the form of ether, ester, amino or amide groups, or together with L is an optionally substituted 1,4-butylene or 1,5-pentylene radical, $E^4$ is a hydrogen or methyl or alkoxycarbonylmethyl radical having 2 to 9 carbon atoms, $E^5$ is an alkoxycarbonyl radical having 1 to 8 carbon atoms or is a methyl radical, $E^6$ is a hydrogen radical or is an alkyl radical having 1 to 8 carbon atoms, $E^7$ is a monovalent hydrocarbyl radical having 1 to 6 carbon atoms, $E^8$ is a hydrogen radical or is a monovalent hydrocarbyl radical having 1 to 6 carbon atoms, and d is 0 or 1.

The letters (L) and (Y) between brackets represent the bond from Q' to L and Y respectively.

Preferably, D is O.

Preferably, W is O.

Preferably, $E^1$ is 2-carboxy-1,2-ethylene, 2-carboxy-1,2-ethenediyl, 3-carboxy-1,3-propylene, 2-carboxy-1,2-cyclohexylene or 2-carboxy-1,2-phenylene.

Preferably, $E^2$ is 1-hydroxy-1,2-ethylene, 1-hydroxy-1,3-propylene, 1-hydroxy-1,4-butylene, 1-hydroxy-1,5-pentylene, 2-hydroxy-1,2-ethyleneoxy or 3-hydroxy-1,3-propyleneoxy.

Preferably, $E^3$ is a hydrogen radical or is a methyl radical.

Preferably, $E^4$ is a hydrogen radical or is methyl, methoxycarbonylmethyl, ethoxycarbonylmethyl or butoxycarbonylmethyl, especially a hydrogen radical or a methyl radical.

Preferably, $E^5$ is methoxycarbonyl, ethoxycarbonyl or butoxycarbonyl or is methyl.

Preferably, $E^6$ is a hydrogen radical or methyl, ethyl or butyl.

Preferably, $E^7$ is methyl.

Preferably, $E^8$ is a hydrogen radical.

Preferably, p is 1 or 2 or 3.

Preferably, r is 0.

Preferably, (p+r) is 1 or 2 or 3.

More preferably, p is 1 or 2 or 3 and r is 0.

The preferred catalysts of the formula (I) are preparable from readily available starting materials in a simple process.

The catalyst of the formula (I) may also be in tautomeric form. All possible tautomeric forms of these catalysts are considered to be equivalent in the context of the present invention.

In addition, the catalyst of the formula (I) may be in protonated form.

The catalyst of the formula (I) may likewise be in complexed form, especially with cations of zinc, iron or molybdenum.

In a preferred embodiment of the invention, Q is an epoxide group. In this case, Y is preferably S or $NR^3$, especially $NR^3$, Q' is a connecting unit of the formula

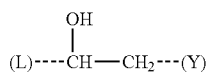

and L is preferably a (p+r)-valent hydrocarbyl radical which has a molecular weight in the range from 15 to 1'500 g/mol and especially has (p+r) ether oxygens and optionally an alkoxysilane group. More particularly, L here is a radical selected from the group consisting of 2-ethylhexyl glycidyl ether, $C_8$- to $C_{10}$-alkyl glycidyl ether, $C_{12}$- to $C_{14}$-alkyl glycidyl ether, cresyl glycidyl ether, tert-butylphenyl glycidyl ether, cardanol glycidyl ether, butane-1,4-diol diglycidyl ether, hexane-1,6-diol diglycidyl ether, neopentyl glycol diglycidyl ether, polypropylene glycol diglycidyl ether having a mean molecular weight in the range from 280 to 1'500 g/mol, bisphenol A diglycidyl ether, bisphenol F diglycidyl ether, 3-glycidoxypropyltrimethoxysilane and 3-glycidoxypropyltriethoxysilane, in each case after removal of the epoxide groups.

In a further preferred embodiment of the invention, Q is a cyclic carbonate group. In this case, in particular, r is 0 and p is 1, Y is X and Q' is a connecting unit of the formula

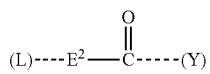

in which $E^2$ is an O-bonded hydroxyalkyleneoxy radical having 2 or 3 carbon atoms, and L is especially a hydrogen radical or a linear alkyl radical having 1 to 12 carbon atoms.

More preferably, $E^2$ is 1-hydroxy-1,2-ethyleneoxy and L is a methyl radical.

In a further preferred embodiment of the invention, Q is a carboxylic ester group. In this case, Y is X, Q' is a connecting unit of the formula

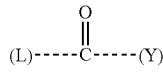

and L is preferably either a hydrogen radical or a covalent bond or a (p+r)-valent hydrocarbyl radical which has a mean molecular weight in the range from 14 to 500 g/mol and optionally has unsaturated components and optionally has ether oxygen.

More particularly, either r is 0, p is 1 and L is a radical selected from 1-pentyl, 3-heptyl, 1-undecyl and phenyl, or (p+r) is 2 and L is a radical selected from 1,4-butylene, 1,2-phenylene, 1,3-phenylene and 1,4-phenylene.

In a further preferred embodiment of the invention, Q is a lactone group. In this case, in particular, r is 0 and p is 1, Y is X and Q' is a connecting unit of the formula

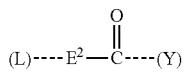

in which $E^2$ is a hydroxyalkylene radical having 2 to 5 carbon atoms, and L is especially a hydrogen radical or a linear alkyl radical having 1 to 12 carbon atoms.

More particularly, $E^2$ and L together are 3-hydroxypropyl, 3-hydroxy-3-methylpropyl, 4-hydroxybutyl, 4-hydroxy-4-methylbutyl or 5-hydroxypentyl.

In a further preferred embodiment of the invention, Q is a ketone group. In this case, in particular, r is 0, p is 1, Y is N and Q' is a connecting unit of the formula

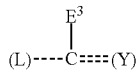

in which either $E^3$ is a monovalent hydrocarbyl radical having 1 to 6 carbon atoms and L is a monovalent hydrocarbyl radical having 1 to 20 carbon atoms, or $E^3$ and L together are a 1,4-butylene or 1,5-pentylene radical.

More particularly, $E^3$ is a methyl radical and L is selected from methyl, ethyl, isopropyl, isobutyl and phenyl, or $E^3$ and L together are 1,4-butylene or 1,5-pentylene.

In a further preferred embodiment of the invention, Q is an aldehyde group. In this case, in particular, r is 0, p is 1, Y is N and Q' is a connecting unit of the formula

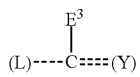

in which $E^3$ is a hydrogen radical and L is a monovalent hydrocarbyl radical which has 1 to 20 carbon atoms and optionally contains oxygen or nitrogen in the form of ester groups, amide groups, ether groups or tertiary amino groups.

More particularly, $E^3$ is a radical selected from 2-propyl, 3-heptyl, 1-undecyl, phenyl, 3-acetyloxy-2-methylprop-2-yl, 3-lauroyloxy-2-methylprop-2-yl and 3-(N-morpholino)-2-methylprop-2-yl.

In a further preferred embodiment of the invention, Q is a 1,3-diketone group. In this case, in particular, r is 0, p is 1, Y is N and Q' is a connecting unit of the formula

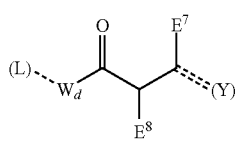

in which d is 0, $E^7$ and L are each a methyl radical and $E^8$ is a hydrogen radical.

In a further preferred embodiment of the invention, Q is a 1,3-keto ester group or a 1,3-keto amide group. In this case, in particular, r is 0 and p is 1 or (p+r) is 2, Y is N and Q' is a connecting unit of the formula

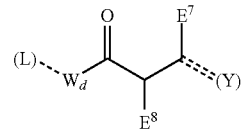

in which d is 1.

In the case that r is 0, p is 1 and W is 0, in particular, $E^7$ is methyl, $E^8$ is hydrogen and L is methyl or ethyl or isopropyl or tert-butyl.

In the case that (p+r) is 2 and W is O, in particular, $E^7$ is methyl, $E^8$ is hydrogen and L is selected from 1,2-ethylene, 1,2-propylene, 3-oxa-1,5-pentylene, 5-methyl-4-oxa-2,6-hexylene, 1,3-propylene, 1,4-butylene, 1,5-pentylene, 3-methyl-1,5-pentylene, 1,6-hexylene and 2,2(4),4-trimethyl-1,6-hexylene.

In the case that r is 0, p is 1 and W is $NR^6$, in particular, $E^7$ is methyl, $E^8$ is hydrogen, and $R^6$ and L are each methyl or ethyl or butyl or 2-ethylhexyl or 2-methoxyethyl.

In a further preferred embodiment of the invention, Q is an isocyanate group. In this case, Y is X and Q' is a connecting unit of the formula

in which D is O, and L is preferably a (p+r)-valent hydrocarbyl radical which has a mean molecular weight in the range from 14 to 20'000 g/mol and optionally has oxygen or nitrogen in the form of ether, ester, urethane, urea, uretdione, isocyanurate, biuret, allophanate, uretonimine, iminooxadiazinedione, oxadiazinetrione or alkoxysilane groups.

In particular, L is a radical selected from butyl, hexyl, lauryl, stearyl, cyclohexyl, phenyl, 3-trimethoxysilylpropyl, 3-triethoxysilylpropyl and polyurethane polymers that contain isocyanate groups from the reaction of polyols with diisocyanates having a mean molecular weight in the range from 500 to 20'000 g/mol after removal of one or more isocyanate groups.

In a further preferred embodiment of the invention, Q is an acrylate or methacrylate group. In this case, Y is X, X is $NR^3$ and Q' is a connecting unit of the formula

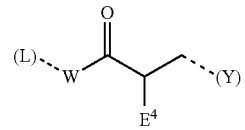

in which W is O and $E^4$ is a hydrogen radical or a methyl radical, and L is preferably a (p+r)-valent hydrocarbyl radical which has a mean molecular weight in the range from 28 to 20'000 g/mol and optionally has oxygen or nitrogen or silicon in the form of ether, ester, urethane, urea, uretdione, isocyanurate, biuret, allophanate, uretonimine, iminooxadiazinedione, oxadiazinetrione or alkoxysilane groups. L here is especially a radical selected from butyl, 2-ethylhexyl, trimethoxysilylpropyl, triethoxysilylpropyl, 1,2-ethylene, 3,6,9-trioxa-1,11-undecylene, 2,5-dimethyl-3,6-dioxa-1,8-nonylene, a polyoxyethylene radical having a molecular weight in the range from 200 to 2'000 g/mol, a polyoxypropylene radical having a molecular weight in the range from 200 to 2'000 g/mol, 1,4-butylene, 1,6-hexylene, 2,2-dimethyl-1,3-propylene, trimethylolpropane after removal of three hydroxyl groups, and polyurethane polymers having (meth)acrylate groups and having a mean molecular weight in the range from 500 to 20'000 g/mol, especially from the reaction of hydroxy-functional (meth)acrylates such as, in particular, 2-hydroxyethyl acrylate with polyurethane polymers containing isocyanate groups.

A suitable catalyst of the formula (I) is especially obtained by the reaction of
at least one guanidine of the formula (II)

HX-A-Z    (II)

where X, A and Z have the definitions given,
with at least one functional compound having at least one reactive group selected from epoxide, aziridine, carbonate, carboxylic anhydride, carboxylic acid, carboxylic ester, lactone, carbonyl chloride, ketone, aldehyde, 1,3-diketone, 1,3-keto ester, 1,3-keto amide, cyanate, thiocyanate, isocyanate, isothiocyanate, (meth)acrylate, (meth)acrylamide, (meth)acrylonitrile, maleate, maleamide, maleimide, fumarate, fumaramide, itaconate, itaconamide, crotonate and crotonamide.

The reaction product from this reaction is preferably used, without workup or purification, as catalyst for the crosslinking of a curable composition. If the reaction gives rise to elimination products owing to condensation reactions, these are preferably removed, especially by distillation, optionally under reduced pressure.

In the reaction of the guanidine of the formula (II) with a functional compound having at least one ketone, aldehyde, 1,3-diketone, 1,3-keto ester or 1,3-keto amide group, the guanidine suitably has an $NH_2$ group as HX group. This gives rise, in a condensation reaction with release of water, to a catalyst of the formula (I) in which the connecting unit Q' is trivalent and Y is N.

The present invention thus provides a process for preparing the catalyst of the formula (I), wherein
at least one guanidine of the formula (II)

HX-A-Z    (II)

where X, A and Z have the definitions given,
is reacted with at least one functional compound having at least one reactive group selected from epoxide, aziridine, carbonate, carboxylic anhydride, carboxylic acid, carboxylic ester, lactone, carbonyl chloride, ketone, aldehyde, 1,3-diketone, 1,3-keto ester, 1,3-keto amide, cyanate, thiocyanate, isocyanate, isothiocyanate, (meth)acrylate, (meth)acrylamide, (meth)acrylonitrile, maleate, maleamide, maleimide, fumarate, fumaramide, itaconate, itaconamide, crotonate and crotonamide.

A preferred reactive group is epoxide, carbonate, carboxylic anhydride, carboxylic ester, lactone, ketone, aldehyde, 1,3-diketone, 1,3-keto ester, 1,3-keto amide, cyanate, isocyanate, acrylate, methacrylate, acrylamide, methacrylamide, maleate, maleimide, fumarate or itaconate.

Particular preference is given to epoxide, carbonate, carboxylic ester, lactone, ketone, aldehyde, 1,3-diketone, 1,3-keto ester, isocyanate, acrylate or methacrylate.

Compounds having the preferred reactive groups are obtainable in a particularly simple manner and enable stable reaction products having a high catalytic activity in a particularly simple process.

A preferred epoxide group is a glycidyl group, especially a glycidyloxy group. A functional compound of this kind can be reacted with a guanidine of the formula (II) in a particularly simple manner.

A preferred aziridine group is an N-aziridinyl group. A functional compound of this kind is readily available and can be reacted with a guanidine of the formula (II) in a particularly efficient manner.

The functional compound preferably has one to six of the reactive groups mentioned, more preferably one or two or three of the reactive groups mentioned.

If the functional compound has more than one reactive group, these are preferably the same, as, for example, in diepoxides or triacrylates. Alternatively, it is possible that the functional compound has various reactive groups.

Suitable functional compounds are especially commercially available substances.

Suitable functional compounds having at least one epoxide group are especially
aliphatic monoepoxides, preferably propylene oxide, butylene oxide, hexylene oxide, allyl glycidyl ether, butyl glycidyl ether, hexyl glycidyl ether, 2-ethylhexyl glycidyl ether, and glycidyl ethers of fatty alcohols, such as, in particular, $C_8$- to $C_{10}$-alkyl glycidyl ether or $C_{12}$- to $C_{14}$-alkyl glycidyl ether, and epoxysilanes such as 3-glycidoxypropyltrimethoxysilane, 3-glycidoxypropyltriethoxysilane, 3-glycidoxypropyldimethoxymethylsilane or 3-glycidoxypropyldiethoxymethylsilane;
aromatic monoepoxides, preferably styrene oxide, or glycidyl ethers of phenol, cresol, tert-butylphenol or cardanol;
aliphatic or cycloaliphatic polyepoxides containing ether groups, preferably glycidyl ethers of glycols such as ethylene glycol, propylene glycol, butylene glycol, hexanediol, octanediol, polypropylene glycols, dimethylolcyclohexane, neopentyl glycol, castor oil, trimethylolpropane, trimethylolethane, pentaerythritol, glycerol, alkoxylated glycerol or alkoxylated trimethylolpropane, and ring-hydrogenated bisphenol A, F or A/F liquid resins; or
aromatic polyepoxides, preferably diglycidyl ethers of bisphenol A, bisphenol F or bisphenol A/F or novolak glycidyl ethers, especially in the form of what are called liquid resins as commercially available, for example, from Dow, Huntsman or Hexion.

Suitable functional compounds having at least one aziridine group are N-alkylaziridines, especially Michael adducts of aziridine or 2-methylaziridine, preferably methyl 3-(aziridin-1-yl)propanoate, methyl 3-(2-methylaziridin-1-yl)-propanoate, butyl 3-(aziridin-1-yl)propanoate, butyl 3-(2-methylaziridin-1-yl)-propanoate, 1,1,1-trimethylolpropane tris(3-(aziridin-1-yl)-propanoate), 1,1,1-trimethylolpropane tris(3-(2-methylaziridin-1-yl)propanoate), pentaerythritol tetrakis (3-(aziridin-1-yl)propanoate or pentaerythritol tetrakis(3-(2-methylaziridin-1-yl)propanoate).

Suitable functional compounds having at least one carbonate group are dialkyl carbonates, preferably dimethyl carbonate, and especially cyclic carbonates, preferably ethylene carbonate, 1,2-propylene carbonate, 4-ethyl-1,3-dioxolan-2-one, 1,3-dioxan-2-one or 5,5-diethyl-1,3-dioxan- 2-one, or cyclic carbonates obtainable by insertion of $CO_2$ into the epoxide group(s) of the abovementioned functional compounds having at least one epoxide group. Particular preference is given to 1,2-propylene carbonate.

Suitable functional compounds having at least one carboxylic anhydride group are anhydrides of monocarboxylic acids, preferably acetic anhydride, and especially cyclic anhydrides of dicarboxylic acids or polycarboxylic acids, preferably succinic anhydride, maleic anhydride, hexahydrophthalic anhydride, methylhexahydrophthalic anhydride, tetrahydrophthalic anhydride, phthalic anhydride, methylphthalic anhydride, trimellitic anhydride, pyromellitic dianhydride or 4,4'-[(isopropylidene)bis(p-phenyleneoxy)]diphthalic dianhydride.

Suitable functional compounds having at least one carboxylic ester group are especially

- alkyl esters of aliphatic, cycloaliphatic and arylaliphatic monocarboxylic acids, preferably of formic acid, acetic acid, propionic acid, butyric acid, isobutyric acid, valeric acid, caproic acid, 2-ethylcaproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, palmitoleic acid, oleic acid, erucic acid, cyclohexanecarboxylic acid or phenylacetic acid, and mixtures of saturated and/or mono- and/or polyunsaturated fatty acids as obtained in the hydrolysis of natural fats and oils of vegetable or animal origin;
- alkyl esters of aromatic monocarboxylic acids, preferably of benzoic acid, toluic acid, salicylic acid, anisic acid or naphthoic acid;
- dialkyl esters of aliphatic and cycloaliphatic dicarboxylic acids (called dibasic esters), preferably of oxalic acid, malonic acid, succinic acid, glutaric acid, adipic acid, pimelic acid, suberic acid, azelaic acid, sebacic acid, dodecane-1,12-dioic acid, hexahydrophthalic acid, hexahydroisophthalic acid, methylhexahydrophthalic acid, hexahydroterephthalic acid, dimer fatty acids, 3,6,9-trioxaundecanedioic acid or of similar derivatives of polyethylene glycol;
- dialkyl esters of aromatic dicarboxylic acids, preferably of phthalic acid, isophthalic acid or terephthalic acid;
- esters of tri- or polyfunctional carboxylic acids, preferably of citric acid or trimellitic acid.

Particular preference is given here to the methyl or ethyl esters.

Suitable functional compounds having at least one lactone group are β-, γ-, δ- or ε-lactones, preferably β-butyrolactone, γ-butyrolactone, γ-valerolactone, γ-caprolactone, γ-heptalactone, γ-octalactone, γ-nonalactone, γ-decalactone, γ-undecalactone, γ-dodecalactone, δ-valerolactone, δ-caprolactone, δ-heptalactone, δ-octalactone, δ-nonalactone, δ-decalactone, δ-undecalactone, δ-dodecalactone, ε-caprolactone, ε-heptalactone, ε-octalactone, ε-nonalactone, ε-decalactone, ε-undecalactone or ε-dodecalactone. Especially suitable are γ-, δ- or ε-lactones, preferably γ-butyrolactone, γ-valerolactone, γ-caprolactone, γ-octalactone, γ-nonalactone, γ-decalactone, γ-undecalactone, γ-dodecalactone, δ-valerolactone, δ-caprolactone, δ-nonalactone, δ-decalactone, δ-undecalactone, δ-dodecalactone, ε-caprolactone, ε-decalactone, ε-undecalactone or ε-dodecalactone. Particular preference is given to γ-butyrolactone, γ-valerolactone, δ-valerolactone, δ-caprolactone or ε-caprolactone.

Suitable functional compounds having at least one keto group are especially

- aliphatic, cycloaliphatic or aromatic ketones, preferably acetone, methyl ethyl ketone, methyl propyl ketone, methyl isopropyl ketone, methyl isobutyl ketone, methyl pentyl ketone, methyl isopentyl ketone, diethyl ketone, dipropyl ketone, diisopropyl ketone, dibutyl ketone, diisobutyl ketone, cyclopentanone, cyclohexanone, acetophenone, propiophenone or benzophenone;
- diketones, preferably butane-2,3-dione, pentane-2,3-dione, hexane-2,3-dione, hexane-3,4-dione, hexane-2,5-dione, 3,4-dimethylhexane-2,5-dione, 1,2-dibenzoylethane, 1,4-bis(2-furyl)butane-1,4-dione, 2-(2-oxopropyl)-cyclopentanone, 1,2-diacetylbenzene, 1,3-diacetylbenzene, 1,4-diacetylbenzene, 1,2-diacetylcyclohexane, 1,3-diacetylcyclohexane or 1,4-diacetylcyclohexane;
- triketones, preferably 1,3,5-triacetylbenzene or 1,3,5-triacetylcyclohexane.

Suitable functional compounds having at least one aldehyde group are especially

- aliphatic, cycloaliphatic or aromatic aldehydes, preferably formaldehyde, acetaldehyde, propanal, 2-methylpropanal, 2,2-dimethylpropanal, 2,2-dimethyl-3-phenylpropanal, butanal, 2-methylbutanal, 2-ethylbutanal, pentanal, 2-methylpentanal, 3-methylpentanal, 4-methylpentanal, 2,3-dimethylpentanal, hexanal, 2-ethylhexanal, heptanal, octanal, nonanal, decanal, undecanal, 2-methylundecanal, dodecanal, methoxyacetaldehyde, cyclopropanecarboxaldehyde, cyclopentanecarboxaldehyde, cyclohexanecarboxaldehyde, diphenylacetaldehyde, benzaldehyde, the isomeric tolualdehydes, 4-ethyl- or 4-propyl- or 4-isopropyl or 4-butyl-benzaldehyde, 2,4-dimethylbenzaldehyde, 2,4,5-trimethylbenzaldehyde, 4-acetoxybenzaldehyde, 4-anisaldehyde, 4-ethoxybenzaldehyde, the isomeric di- or trialkoxybenzaldehydes, 2-, 3- or 4-nitrobenzaldehyde, 2-, 3- or 4-formylpyridine, furfural, 2-thiophenecarbaldehyde, 1- or 2-naphthylaldehyde, 3- or 4-phenyloxybenzaldehyde, quinoline-2-carbaldehyde or the positional 3, 4, 5, 6, 7 or 8 isomers thereof, anthracene-9-carbaldehyde, cinnamaldehyde or substituted cinnamaldehydes;
- aldehydes having hydroxyl groups, preferably 2,2-dimethyl-3-hydroxypropanal, 3-bis(2-hydroxyethyl)amino-2,2-dimethylpropanal, 3-bis(2-hydroxypropyl)amino-2,2-dimethylpropanal, the isomeric salicylaldehydes or vanillin;
- aldehydes having ester groups, preferably 2,2-dimethyl-3-formoxypropanal, 2,2-dimethyl-3-acetoxypropanal, 2,2-dimethyl-3-isobutoyloxypropanal, 2,2-dimethyl-3-caproyloxypropanal, 2,2-dimethyl-3-(2-ethylhexoyloxy)propanal, 2,2-dimethyl-3-capryloyloxypropanal, 2,2-dimethyl-3-caprinoyloxypropanal, 2,2-dimethyl-3-lauroyloxypropanal, 2,2-dimethyl-3-myristoyloxypropanal, 2,2-dimethyl-3-palmitoyloxypropanal, 2,2-dimethyl-3-stearoyloxypropanal, 2,2-dimethyl-3-oleyloxypropanal, 2,2-dimethyl-3-benzoyloxypropanal or methyl or ethyl glyoxylate;
- aldehydes having ether groups, preferably 2,2-dimethyl-3-phenoxypropanal, 3-cyclohexyloxy-2,2-dimethylpropanal, 2,2-dimethyl-3-(2-ethylhexyloxy)-propanal, 2,2-dimethyl-3-lauroxypropanal or 2,2-dimethyl-3-stearoxypropanal;
- aldehydes having tertiary amino groups, preferably 2,2-dimethyl-3-(N,N-dimethylamino)propanal, 2,2-dimethyl-3-(N,N-diethylamino)propanal, 2,2-dimethyl-3-(N,N-dibutylamino)propanal, 2,2-dimethyl-3-(N-pyrrolidino)-propanal, 2,2-dimethyl-3-(N-piperidino)propanal, 2,2-dimethyl-3-(N-morpholino)propanal, 3-(N-(2,6-dimethylmorpholino))propanal, 3-bis-(methoxyethyl)amino-2,2-dimethylpropanal or 3-bis(2-hydroxypropyl)amino-2,2-dimethylpropanal;

dialdehydes, preferably glyoxal, glutaraldehyde, orthophthalaldehyde, isophthalaldehyde, terephthalaldehyde, naphthalenedicarboxaldehyde, anthracenedicarboxaldehyde, 2,5-furandicarbaldehyde, 2,5-thiophenedicarbaldehyde, cyclopentanedicarbaldehyde, 1,2-cyclohexanedicarbaldehyde, 1,3-cyclohexanedicarbaldehyde, 1,4-cyclohexanedicarbaldehyde, 2(3),5(6)-diformylbicyclo[2.2.1]heptane (norbornanedicarbaldehyde), 3(4),8(9)-diformyltricyclo[5.2.1.0$^{2,6}$]decane (tricyclodecanedicarbaldehyde or TCD dialdehyde), 2,5-tetrahydrofuran-dicarbaldehyde, 2,5-tetrahydrothiophenedicarbaldehyde, 1,3-bis(4,4-dimethyl-5-oxo-2-pentyl)benzene, 1,4-bis(4,4-dimethyl-5-oxo-2-pentyl)-benzene, 3-(3-oxopropyl)cyclohexanecarbaldehyde, 4-(3-oxopropyl)-cyclohexanecarbaldehyde, 3-(1-formylethyl)cyclohexanecarbaldehyde, 4-(1-formylethyl)cyclohexanecarbaldehyde, N,N'-bis(2,2-dimethyl-3-oxopropyl)-piperazine, N,N'-bis(2,2-diethyl-3-oxopropyl)piperazine, N,N'-bis(2-methyl-2-propyl-3-oxopropyl)piperazine or N,N'-bis(2-butyl-2-ethyl-3-oxopropyl)-piperazine;

trialdehydes, preferably benzene-1,3,5-tricarbaldehyde or cyclohexane-1,3,5-tricarbaldehyde.

Preferred functional compounds having at least one 1,3-diketo group are pentane-2,4-dione, heptane-3,5-dione, 6-methylheptane-3,5-dione, 2,2,6,6-tetramethylheptane-3,5-dione, 2,2,4,6,6-pentamethylheptane-3,5-dione, 1,3-diphenylpropane-1,3-dione, 3-phenylpentane-2,4-dione, 2-acetylcyclopentanone or 2-acetylcyclohexanone.

Preferred functional compounds having at least one 1,3-keto ester group are methyl acetoacetate, ethyl acetoacetate, propyl acetoacetate, isopropyl acetoacetate, butyl acetoacetate, tert-butyl acetoacetate, ethyl 3-oxovalerate or ethyl 3-oxohexanoate, or polyfunctional acetoacetates from the polyesterification of polyols, preferably ethylene glycol bis(acetoacetate), propylene glycol bis(acetoacetate), diethylene glycol bis(acetoacetate), dipropylene glycol bis(acetoacetate), propane-1,3-diol bis(acetoacetate), butane-1,4-diol bis(acetoacetate), pentane-1,5-diol bis(acetoacetate), 3-methyl-pentane-1,5-diol bis(acetoacetate), hexane-1,6-diol bis(acetoacetate), 2,2(4),4-trimethylhexane-1,6-diol bis(acetoacetate), poly(oxyalkylene) bis(acetoacetate), cyclohexane-1,3-dimethanol bis(acetoacetate), cyclohexane-1,4-diol bis(acetoacetate), glycerol tris(acetoacetate) or trimethylolpropane tris(acetoacetate).

Preferred functional compounds having at least one 1,3-keto amide group are N,N-diethyl-3-oxobutanamide, N,N-dibutyl-3-oxobutanamide, N,N-bis(2-ethylhexyl)-3-oxobutanamide, N,N-bis(2-methoxyethyl)-3-oxobutanamide, N,N-dibutyl-3-oxoheptanamide, N,N-bis(2-methoxyethyl)-3-oxoheptanamide, N,N-bis(2-ethylhexyl)-2-oxocyclopentanecarboxamide, N,N-dibutyl-3-oxo-3-phenylpropanamide or N,N-bis(2-methoxyethyl)-3-oxo-3-phenylpropanamide, or polyfunctional keto amides formed from the polyamidation of polyether amines with diketene or a 1,3-keto ester.

Suitable functional compounds having at least one cyanate group are especially cyanic esters of phenols or polyphenols, preferably phenyl cyanate, 2,2-bis(4-cyanatophenyl)propane (bisphenol A dicyanate), bis(4-cyanato-phenyl)methane, bis(4-cyanato-3,5-dimethylphenyl)methane, 1,1-bis(4-cyanatophenyl)ethane, bis(4-cyanatophenyl)dicyclopentadiene, m-phenylene dicyanate, p-phenylene dicyanate, 4,4'-dicyanatodiphenyl sulfone, 1,3,5-tricyanatobenzene, novolak cyanates, cyanates of ester-modified bisphenols, especially of caprolactone-modified bisphenols, and polymers, having cyanate groups, of the polycyanates mentioned with polyols, especially polyether polyols or polyester polyols.

Suitable functional compounds having at least one isocyanate group are especially aliphatic or cycloaliphatic or aromatic monoisocyanates, preferably, butyl isocyanate, hexyl isocyanate, lauryl isocyanate, stearyl isocyanate, cyclohexyl isocyanate, allyl isocyanate or phenyl isocyanate, and also 3-isocyanatopropyltrimethoxysilane, 3-isocyanatopropyltriethoxysilane, 3-isocyanatopropyldimethoxymethylsilane or 3-isocyanatopropyldiethoxy-methylsilane;

aliphatic or cycloaliphatic di- or triisocyanates, preferably tetramethylene 1,4-diisocyanate, 2-methylpentamethylene 1,5-diisocyanate, hexamethylene 1,6-diisocyanate (HDI), 2,2,4- and/or 2,4,4-trimethylhexamethylene 1,6-diisocyanate (TMDI), decamethylene 1,10-diisocyanate, dodecamethylene 1,12-diisocyanate, lysine diisocyanate or lysine ester diisocyanate, cyclohexane 1,3- or 1,4-diisocyanate, 1-methyl-2,4- and/or -2,6-diisocyanatocyclohexane (H$_6$TDI), 1-isocyanato-3,3,5-trimethyl-5-isocyanatomethylcyclohexane (IPDI), perhydro-2,4'- and/or -4,4'-diphenylmethane diisocyanate (H$_{12}$MDI), 1,3- or 1,4-bis-(isocyanatomethyl)-cyclohexane, m- or p-xylylene diisocyanate (m- or p-XDI), tetramethyl-xylylene 1,3- or 1,4-diisocyanate (m- or p-TMXDI), bis(1-isocyanato-1-methylethyl)naphthalene, dimer or trimer fatty acid isocyanates such as, in particular, 3,6-bis(9-isocyanatononyl)-4,5-di-(1-heptenyl)cyclohexene (dimeryl diisocyanate); more preferably HDI or IPDI;

aromatic di- or triisocyanates, preferably tolylene 2,4- and/or 2,6-diisocyanate (TDI), diphenylmethane 4,4'- and/or 2,4'- and/or 2,2'-diisocyanate (MDI), mixtures of MDI and MDI homologs (polymeric MDI or PMDI), phenylene 1,3- or 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODD, dianisidine diisocyanate (DADI), 1,3,5-tris(isocyanatomethyl)benzene, tris(4-isocyanatophenyl)methane or tris(4-isocyanatophenyl) thiophosphate; more preferably MDI or TDI;

oligomers and derivatives of the di- and triisocyanates mentioned, preferably derived from HDI, IPDI, MDI or TDI. Especially suitable among these are commercially available types, preferably HDI biurets, HDI isocyanurates, HDI uretdiones, HDI iminooxadiazinediones, HDI allophanates, IPDI isocyanurates, TDI oligomers or mixed isocyanurates based on TDI/HDI, or room temperature liquid forms of MDI (called "modified MDI"), which are mixtures of MDI with MDI derivatives such as, in particular, MDI carbodiimides or MDI uretonimines or MDI urethanes, mixtures of MDI and MDI homologs (polymeric MDI or PMDI). In practice, oligomeric polyisocyanates of this kind are typically mixtures of substances having different degrees of oligomerization and/or chemical structures. They preferably have a mean NCO functionality of 2.1 to 4.0.

Polyurethane polymers containing isocyanate groups from the reaction of polyols, especially polyether polyols, with polyisocyanates, as described hereinafter.

Preferably, the functional compound having at least one isocyanate group has aliphatic isocyanate groups, especially derived from IPDI or HDI. These isocyanate groups have moderate reactivity, which facilitates the reaction with a guanidine of the formula (II).

A suitable polyurethane polymer containing isocyanate groups is preferably obtained from the reaction of polyols with a superstoichiometric amount of polyisocyanates, especially diisocyanates. The reaction is preferably conducted with exclusion of moisture at a temperature in the range from 50° C. to 100° C., optionally in the presence of suitable catalysts. The excess of polyisocyanate is preferably chosen so as to leave, in the polyurethane polymer after the conversion of all hydroxyl groups, a content of free isocyanate groups in the range from 0.5% to 20% by weight, preferably 0.5% to 10% by weight, more preferably 0.5% to 5% by weight, based on the overall polymer.

A suitable polyurethane polymer containing isocyanate groups preferably has a mean molecular weight in the range from 500 to 20'000 g/mol.

Suitable polyisocyanates are especially diisocyanates, preferably hexamethylene 1,6-diisocyanate (HDI), 1-isocyanato-3,3,5-trimethyl-5-isocyanatomethylcyclohexane (isophorone diisocyanate or IPDI), tolylene 2,4- and/or 2,6-diisocyanate (TDI) or diphenylmethane 4,4'-, 2,4'- and/or 2,2'-diisocyanate (MDI).

Suitable polyols are especially polyether polyols, preferably polyoxyalkylene polyols, which are polymerization products of ethylene oxide or 1,2-propylene oxide or 1,2- or 2,3-butylene oxide or oxetane or tetrahydrofuran or mixtures thereof, possibly polymerized with the aid of a starter molecule having two or more active hydrogen atoms; polyester polyols, preferably products from the polycondensation of diols or triols with lactones or dicarboxylic acids or esters or anhydrides thereof; polycarbonate polyols, OH-terminal block copolymers having at least two different blocks having polyether, polyester or polycarbonate units; polyacrylate polyols or polymethacrylate polyols; polyhydroxy-functional fats or oils, especially natural fats or oils; or polyhydrocarbon polyols, for example polyhydroxy-functional polyolefins.

Further suitable polyols are di- or polyhydric alcohols of low molecular weight, preferably ethane-1,2-diol, propane-1,2-diol, neopentyl glycol, dibromoneopentyl glycol, diethylene glycol, triethylene glycol, the isomeric dipropylene glycols or tripropylene glycols, the isomeric butanediols, pentanediols, hexanediols, heptanediol, octanediols, nonanediols, decanediols, undecanediol, cyclohexane-1,3- or -1,4-dimethanol, hydrogenated bisphenol A, dimer fatty acid alcohols, 1,1,1-trimethylolethane, 1,1,1-trimethylolpropane, glycerol, pentaerythritol, sugar alcohols or sugars, or low molecular weight alkoxylation products of the di- or polyhydric alcohols mentioned.

Also especially suitable are mixtures of the polyols mentioned.

Especially suitable are diols or triols or mixtures thereof.

Suitable functional compounds having at least one isothiocyanate group are especially methyl isothiocyanate, ethyl isothiocyanate, propyl isothiocyanate, isopropyl isothiocyanate, n-butyl isothiocyanate, 2-isothiocyanatobutane, cyclohexyl isothiocyanate, n-octyl isothiocyanate, allyl isothiocyanate, phenyl isothiocyanate, o- or m- or p-tolyl isothiocyanate, phenylene 1,2- or 1,3- or 1,4-diisothiocyanate or tolylene 2,4- and/or 2,6-diisothiocyanate.

Suitable functional compounds having at least one acrylate or methacrylate group are especially acrylic esters or methacrylic esters, preferably methyl (meth)acrylate, ethyl (meth)acrylate, butyl (meth)acrylate, 2-ethylhexyl (meth)acrylate, lauryl (meth)acrylate, stearyl (meth)acrylate, cyclohexyl (meth)acrylate, tetrahydrofuryl (meth)acrylate, isobornyl (meth)acrylate, 2-phenoxyethyl (meth)acrylate, 2-(2-phenoxyethoxy)ethyl (meth)acrylate, 2-(4-nonyl-phenoxy)ethyl (meth)acrylate, or 3-(meth)acryloyloxypropyltrimethoxysilane, 3-(meth)acryloyloxypropyltriethoxysilane, 3-(meth)acryloyloxypropyldi-methoxymethylsilane or 3-(meth)acryloyloxypropyldiethoxymethylsilane;

di- or polyfunctional acrylates or methacrylates of aliphatic polyethers, polyesters, novolaks, phenols, aliphatic or cycloaliphatic alcohols, glycols, polyester glycols or mono- or polyalkoxylated derivatives of the aforementioned compounds, preferably ethylene glycol di(meth)acrylate, tetraethylene glycol di(meth)acrylate, tripropylene glycol di(meth)acrylate, polyethylene glycol di(meth)acrylate, polypropylene glycol di(meth)acrylate, butane-1,4-diol di(meth)acrylate, hexane-1,6-diol di(meth)acrylate, neopentyl glycol di(meth)acrylate, trimethylolpropane tri(meth)acrylate, pentaerythritol tetra(meth)acrylate, dipentaerythritol tetra(meth)acrylate, dipentaerythritol penta(meth)acrylate, dipentaerythritol hexa(meth)acrylate; di- or polyacryloyl- or -methacryloyl-functional polybutadienes, polyisoprenes or block copolymers thereof; adducts formed from di- or polyfunctional epoxides, such as those already mentioned, with acrylic acid or methacrylic acid; di- or polyfunctional polyurethane acrylates or methacrylates, especially reaction products of polyurethane polymers containing isocyanate groups with 2-hydroxyethyl acrylate; tris(2-hydroxyethyl) isocyanurate tri(meth)acrylate or tris(2-hydroxyethyl) cyanurate tri(meth)acrylate;

polyurethane polymers having two or more acrylate or methacrylate groups, especially having a mean molecular weight in the range from 500 to 20'000 g/mol, especially from the reaction of hydroxy-functional (meth)acrylates, such as 2-hydroxyethyl acrylate in particular, with polyurethane polymers containing isocyanate groups.

Suitable functional compounds having at least one acrylamide or methacrylamide group are especially acrylamide, methacrylamide or N-substituted acrylamides or methacrylamides, preferably N,N-dimethylacrylamide, N,N-diethylacryl-amide, N-methylacrylamide, N-ethylacrylamide, N-propylacrylamide, N-isopropylacrylamide, N-butylacrylamide, N-tert-butylacrylamide, N,N-dimethylaminopropylacrylamide, N-butoxymethylacrylamide, N-isobutoxymethylacrylamide or diacetoneacrylamide;

di- or polyfunctional acrylamides or methacrylamides, preferably N,N'-methylenebis(acrylamide), N,N'-ethylenebis(acrylamide) or N,N',N"-tris((meth)acryloyl)perhydrotriazine.

Suitable functional compounds having at least one acrylonitrile or methacrylonitrile group are especially acrylonitrile or methacrylonitrile.

Preference is given to acrylonitrile.

Suitable functional compounds having at least one maleate group are especially dialkyl maleates, preferably dimethyl maleate, diethyl maleate or dibutyl maleate.

Suitable functional compounds having at least one fumarate group are especially dialkyl fumarates, preferably dimethyl fumarate, diethyl fumarate or dibutyl fumarate.

Suitable functional compounds having at least one maleimide group are especially maleimide and N-alkylmaleimides, preferably N-methylmaleimide, N-ethylmaleimide, N-butylmaleimide, N-hexylmaleimide or 1,1-(1,6-hexylene)bis-(1H-pyrrole-2,5-dione).

Suitable functional compounds having at least one itaconate group are especially dialkyl itaconates, preferably dimethyl itaconate, diethyl itaconate, dibutyl itaconate or dihexyl itaconate.

More preferably, the functional compound is selected from the group consisting of 2-ethylhexyl glycidyl ether, $C_8$- to $C_{10}$-alkyl glycidyl ethers, $C_{12}$- to $C_{14}$-alkyl glycidyl ethers, cresyl glycidyl ether, tert-butylphenyl glycidyl ether, cardanol glycidyl ether, butane-1,4-diol diglycidyl ether, hexane-1,6-diol diglycidyl ether, neopentyl glycol diglycidyl ether, polypropylene glycol diglycidyl ether having a mean molecular weight in the range from 280 to 1000 g/mol, bisphenol A diglycidyl ether, bisphenol F diglycidyl ether, 3-glycidoxypropyl-trimethoxysilane, 3-glycidoxypropyltriethoxysilane, 1,2-propylene carbonate, succinic anhydride, maleic anhydride, hexahydrophthalic anhydride, phthalic anhydride, methyl caproate, ethyl caproate, methyl 2-ethylcaproate, ethyl 2-ethylcaproate, methyl laurate, ethyl laurate, methyl benzoate, ethyl benzoate, dimethyl adipate, diethyl adipate, dimethyl phthalate, diethyl phthalate, dimethyl isophthalate, diethyl isophthalate, dimethyl terephthalate, diethyl terephthalate, γ-butyrolactone, γ-valerolactone, δ-valerolactone, δ-caprolactone, ε-caprolactone, acetone, methyl ethyl ketone, methyl isopropyl ketone, methyl isobutyl ketone, cyclopentanone, cyclohexanone, acetophenone, 2-methylpropanal, 2-ethylhexanal, dodecanal, benzaldehyde, 2,2-dimethyl-3-acetoxypropanal, 2,2-dimethyl-3-lauroyloxypropanal, 2,2-dimethyl-3-(N-morpholino)propanal, 3-bis(methoxyethyl)amino-2,2-dimethylpropanal, terephthalaldehyde, pentane-2,4-dione, methyl acetoacetate, ethyl acetoacetate, isopropyl acetoacetate, tert-butyl acetoacetate, ethylene glycol bis(acetoacetate), propylene glycol bis(acetoacetate), diethylene glycol bis(acetoacetate), dipropylene glycol bis(acetoacetate), propane-1,3-diol bis(acetoacetate), butane-1,4-diol bis(acetoacetate), pentane-1,5-diol bis(acetoacetate), 3-methylpentane-1,5-diol bis(acetoacetate), hexane-1,6-diol bis(acetoacetate), 2,2(4),4-trimethyl-1,6-hexanediol bis(acetoacetate), N,N-dimethyl-3-oxobutanamide, N,N-diethyl-3-oxobutanamide, N,N-dibutyl-3-oxobutanamide, N,N-bis(2-ethylhexyl)-3-oxobutanamide, N,N-bis(2-methoxyethyl)-3-oxobutanamide, butyl isocyanate, hexyl isocyanate, lauryl isocyanate, stearyl isocyanate, cyclohexyl isocyanate, phenyl isocyanate, 3-isocyanatopropyltrimethoxysilane, 3-isocyanatopropyltriethoxysilane, polyurethane polymers containing isocyanate groups and having a mean molecular weight in the range from 500 to 20'000 g/mol from the reaction of polyols with diisocyanates, methyl isothiocyanate, ethyl isothiocyanate, isopropyl isothiocyanate, butyl isothiocyanate, cyclohexyl isothiocyanate, phenyl isothiocyanate, butyl (meth)acrylate, 2-ethylhexyl (meth)acrylate, (meth)acryloyloxypropyltrimethoxysilane, (meth)acryloyloxypropyltriethoxysilane, ethylene glycol di(meth)acrylate, tetraethylene glycol di(meth)acrylate, tripropylene glycol di(meth)acrylate, polyethylene glycol di(meth)acrylate having a mean molecular weight in the range from 200 to 2000 g/mol, polypropylene glycol di(meth)acrylate having a mean molecular weight in the range from 200 to 2000 g/mol, butane-1,4-diol di(meth)acrylate, hexane-1,6-diol di(meth)acrylate, neopentyl glycol di(meth)acrylate, trimethylolpropane tri(meth)acrylate, polyurethane polymers having (meth)acrylate groups and having a mean molecular weight in the range from 500 to 20'000 g/mol, especially from the reaction of hydroxy-functional (meth)acrylates with polyurethane polymers containing isocyanate groups, acrylonitrile, diethyl maleate, diethyl fumarate, N-ethylmaleimide and diethyl itaconate.

A catalyst of the formula (I) from the reaction of at least one guanidine of the formula (II) with at least one of the functional compounds described is preferably obtained by roughly stoichiometric use of the HX groups in relation to the reactive groups of the functional compound, as a result of which the catalyst obtained is substantially free of the reactive groups mentioned. The reaction can alternatively be conducted in sub- or superstoichiometric mode. Especially in the case of use of a functional compound containing more than one of the reactive groups mentioned, a substoichiometric conversion of the reactive groups may be advantageous since the catalyst of the formula (I), because of the reactive groups present, has an additional functionality that can serve, for example, for incorporation thereof into the polymer matrix or anchoring thereof onto a substrate or a filler.

A 1,3-diketone or 1,3-keto ester or 1,3-keto amide or (meth)acrylate or maleate or fumarate or itaconate group can react twice with HX groups. If the reaction is conducted in a stoichiometric manner in such a way that just one HX group is present per group of this kind, it is preferably condensed onto the keto group or added onto the double bond. If, by contrast, more than one HX group is present, a transesterification or amidation is additionally possible. Preferably, such a group is reacted just once.

The reaction is especially effected under conditions as typically used for reactions between the reactive groups involved in the particular reaction, preferably at a temperature in the range from 0° C. to 160° C. The reaction can be effected with use of a solvent or preferably in a solvent-free manner. It is optionally possible to also use auxiliaries, for example catalysts, initiators, desiccants or stabilizers.

A suitable guanidine of the formula (II) for the reaction with at least one functional compound is especially obtained from the reaction of at least one amine of the formula (III)

$$HX'\text{-}A'\text{-}NHR^1 \qquad \text{(III)}$$

where

X' is O or S or $NR^8$ and $R^8$ is a hydrogen radical or is an alkyl or cycloalkyl or aralkyl radical which has 1 to 8 carbon atoms and optionally contains a primary or secondary or tertiary amino group, A' is A, where A' together with $R^8$ may also be a trivalent hydrocarbyl radical which has 5 to 10 carbon atoms and optionally contains a tertiary amine nitrogen, and A and $R^1$ have the definitions already given, with at least one reagent for introduction of guanidine groups, selected from the group consisting of cyanamides, carbodiimides, ureas, O-alkylisoureas, thioureas, S-alkylisothioureas, aminoiminomethanesulfonic acids, guanylpyrazoles and guanidines.

X' is preferably O or $NR^8$.

$R^8$ is preferably a hydrogen radical.

$R^8$ is further preferably an alkyl or cycloalkyl radical having 1 to 8 carbon atoms.

$R^8$ is further preferably a radical of the formula

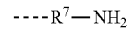

—$R^7$—$NH_2$ where $R^7$ has the definitions already given.

R[8] is further preferably an N,N-dimethylaminopropyl radical.

R[8] is further preferably, together with A' and with inclusion of the nitrogen atom, piperidin-4-ylmethyl or 2-(piperidin-4-yl)ethyl or 2-piperazinoethyl.

The reaction is preferably conducted at elevated temperature, optionally under elevated pressure and optionally in the presence of a catalyst, wherein elimination products released from the reagent are preferably removed during or after the reaction, especially by means of distillation, optionally under reduced pressure.

Preferably, the ratio between the amine of the formula (III) and the reagent is chosen such that the reagent is fully converted in the reaction.

Preferred reagents for introduction of guanidine groups are cyanamides or carbodiimides.

A particularly preferred reagent for introduction of guanidine groups is a carbodiimide of the formula $R^5$—N═C═N—$R^2$ where $R^2$ and $R^5$ have the definitions described.

N,N'-Diisopropylcarbodiimide (DIC), N,N'-di-tert-butylcarbodiimide, N,N'-dicyclohexylcarbodiimide (DCC) or N-ethyl-N'-(3-dimethylaminopropyl)carbodiimide (EDC) is particularly suitable, especially N,N'-diisopropylcarbodiimide (DIC) or N,N'-dicyclohexylcarbodiimide (DCC). These reagents are readily available and can be converted efficiently to guanidines.

Suitable amines of the formula (III) are especially aliphatic or cycloaliphatic hydroxylamines, especially 2-aminoethanol, 2-methylaminoethanol (2-amino-1-propanol), 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol, a primary amino group-bearing derivative of glycols such as diethylene glycol, dipropylene glycol, dibutylene glycol, or higher oligomers or polymers of these glycols, especially 2-(2-aminoethoxy)ethanol, 2-(2-(2-aminoethoxy)ethoxy)ethanol, α-(2-hydroxymethylethyl)-ω-(2-aminomethylethoxy)poly(oxy(methyl-1,2-ethanediyl)), polyalkoxylated tri- or polyhydric alcohol derivatives that bear one hydroxyl group and one primary amino group, products from the single cyanoethylation and subsequent hydrogenation of glycols, especially 3-(2-hydroxyethoxy)propylamine, 3-(2-(2-hydroxyethoxy)ethoxy)propylamine or 3-(6-hydroxyhexyloxy)-propylamine, and also hydroxylamines having one primary and one secondary amino group, such as, in particular, N-(2-aminoethyl)-2-aminoethanol or N-(3-aminopropyl)-2-aminoethanol;

aliphatic mercapto amines, especially 2-aminoethanethiol (cysteamine), 3-aminopropanethiol, 4-amino-1-butanethiol, 6-amino-1-hexanethiol, 8-amino-1-octanethiol, 10-amino-1-decanethiol or 12-amino-1-dodecanethiol;

aliphatic, cycloaliphatic or arylaliphatic primary diamines, especially ethylenediamine, propane-1,2- and -1,3-diamine, 2-methylpropane-1,2-diamine, 2,2-dimethylpropane-1,3-diamine, butane-1,3- and -1,4-diamine, pentane-1,3-diamine (DAMP), pentane-1,5-diamine, 1,5-diamino-2-methylpentane (MPMD), 2-butyl-2-ethylpentane-1,5-diamine (C11 neodiamine), hexane-1,6-diamine, 2,5-dimethylhexane-1,6-diamine, 2,2,4- and 2,4,4-trimethylhexamethylenediamine (TMD), heptane-1,7-diamine, octane-1,8-diamine, nonane-1,9-diamine, decane-1,10-diamine, undecane-1,11-diamine, dodecane-1,12-diamine, 1,2-, 1,3- or 1,4-diaminocyclo-hexane, bis(4-aminocyclohexyl)methane, bis(4-amino-3-methylcyclohexyl)-methane, bis(4-amino-3-ethylcyclohexyl)methane, bis(4-amino-3,5-dimethyl-cyclohexyl)methane, bis(4-amino-3-ethyl-5-methylcyclohexyl)methane, 1-amino-3-aminomethyl-3,5,5-trimethylcyclohexane (isophoronediamine or IPD), 2- and/or 4-methyl-1,3-diaminocyclohexane, 1,3- or 1,4-bis(amino-methyl)cyclohexane, 2,5(2,6)-bis(aminomethyl)bicyclo[2.2.1]heptane (NBDA), 3(4),8(9)-bis(aminomethyl)tricyclo[5.2.1.0$^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]undecane, 1,3-bis(aminomethyl)-benzene, 1,4-bis(aminomethyl)benzene, 4-aminomethyl-1,8-octanediamine, or products from the double cyanoethylation and subsequent reduction of fatty amines derived from natural fatty acids, such as N,N-bis(3-amino-propyl)dodecylamine or N,N-bis(3-aminopropyl)tallowalkylamine, available as Triameen® Y12D or Triameen® YT (from Akzo Nobel);

aliphatic or cycloaliphatic primary diamines containing ether groups, especially bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine, cycloaliphatic diamines containing ether groups from the propoxylation and subsequent amination of 1,4-dimethylolcyclohexane, obtainable especially as Jeffamine® RFD-270 (from Huntsman), polyoxyalkyleneamines having a mean molecular weight in the range from 200 to 500 g/mol, as commercially available, for example, under the Jeffamine® trade name (from Huntsman), Polyetheramine (from BASF) and PC Amine® (from Nitroil), characterized in that they bear 2-aminopropyl or 2-aminobutyle end groups, especially Jeffamine® D-230, Jeffamine® D-400, Jeffamine® XTJ-582, Jeffamine® HK-511 or Jeffamine® XTJ-566 (all from Huntsman), or analogous products from BASF and Nitroil;

diamines having one primary and one secondary amino group, especially N-methylethane-1,2-diamine, N-ethylethane-1,2-diamine, N-butylethane-1,2-diamine, N-hexylethane-1,2-diamine, N-(2-ethylhexyl)ethane-1,2-diamine, N-cyclohexylethane-1,2-diamine, 4-aminomethylpiperidine, 4-((2-amino)-ethyl)piperidine, N-methylpropane-1,3-diamine, N-ethylpropane-1,3-diamine, N-butylpropane-1,3-diamine, N-hexylpropane-1,3-diamine, N-(2-ethylhexyl)-propane-1,3-diamine, N-dodecylpropane-1,3-diamine, N-cyclohexylpropane-1,3-diamine, 3-methylamino-1-pentylamine, 3-ethylamino-1-pentylamine, 3-butylamino-1-pentylamine, 3-hexylamino-1-pentylamine, 3-(2-ethylhexyl)-amino-1-pentylamine, 3-dodecylamino-1-pentylamine, 3-cyclohexylamino-1-pentylamine, or 3-aminopropylated fatty amines such as, in particular, N-coco-alkylpropane-1,3-diamine, N-oleylpropane-1,3-diamine, N-soyaalkylpropane-1,3-diamine, N-tallowalkylpropane-1,3-diamine or N—($C_{16-22}$-alkyl)propane-1,3-diamine, as available, for example, under the Duomeen® trade name (from Akzo Nobel);

polyalkyleneamines and further polyamines having primary and secondary amino groups and/or tertiary amino groups, especially diethylenetriamine (DETA), triethylenetetramine (TETA), tetraethylenepentamine (TEPA), pentaethylenehexamine (PEHA), polyethylenepolyamine having 5 to 7 ethyleneamine units (called "higher ethylenepolyamine", HEPA), dipropylenetriamine (DPTA), N-(2-aminoethyl)propane-1,3-diamine (N3 amine), N,N'-bis(3-aminopropyl)ethylenediamine (N4 amine), bishexamethylenetriamine (BHMT), N3-(3-aminopentyl)pentane-1,3-diamine, N5-(3-aminopropyl)-2-methylpentane-1,5-diamine, N5-(3-amino-1-ethylpropyl)-2-methylpentane-1,5-diamine, N-(2-aminoethyl)piperazine, N-(2-aminopropyl)piperazine, N1-((3-dimethylamino)propyl)-1,3-diaminopropane, N-methyl-N'-(2-aminoethyl)ethane-1,2-diamine, N-methyl-N'-(3-aminopropyl)ethane-1,2-diamine, N-methyl-N'-(2-aminoethyl)propane-1,3-diamine or N-methyl-N'-(3-aminopropyl)propane-1,3-diamine.

Preferably, the amine of the formula (III) is selected from the group consisting of ethylenediamine, propane-1,2-diamine, propane-1,3-diamine, N-methylethane-1,2-diamine, N-ethylethane-1,2-diamine, N-butylethane-1,2-diamine, N-hexylethane-1,2-diamine, N-(2-ethylhexyl)ethane-1,2-diamine, N-cyclohexylethane-1,2-diamine, N-methylpropane-1,3-diamine, N-ethylpropane-1,3-diamine, N-butylpropane-1,3-diamine, N-hexylpropane-1,3-diamine, N-(2-ethylhexyl)propane-1,3-diamine, N-cyclohexylpropane-1,3-diamine, pentane-1,3-diamine (DAMP), 1,5-diamino-2-methylpentane (MPMD), hexane-1,6-diamine, 2,2,4- and 2,4,4-trimethylhexamethylenediamine (TMD), octane-1,8-diamine, decane-1,10-diamine, dodecane-1,12-diamine, 1-amino-3-aminomethyl-3,5,5-trimethylcyclohexane (isophoronediamine or IPD), 1,3-bis(aminomethyl)cyclohexane, 1,4-bis(aminomethyl)cyclohexane, 1,3-bis(aminomethyl)benzene, 2- and/or 4-methyl-1,3-diaminocyclohexane, 4-aminomethylpiperidine, 4-((2-amino)ethyl)piperidine, N-(2-aminoethyl)piperazine, diethylenetriamine, dipropylenetriamine, N-(2-aminoethyl)propane-1,3-diamine (N3 amine), bis(hexamethylene)triamine (BHMT), N'-methyl-N'-(3-aminopropyl)propane-1,3-diamine, $N^1$-((3-dimethylamino)propyl)-1,3-diaminopropane, bis(2-aminoethyl) ether, 3,6-dioxaoctane-1,8-diamine, 4,7-dioxadecane-1,10-diamine, 2-aminoethanol, 1-amino-2-propanol, 3-amino-1-propanol, 2-amino-2-methylpropanol, 5-amino-1-pentanol, 6-amino-1-hexanol, 3-aminomethyl-3,5,5-trimethylcyclohexanol, 2-(2-aminoethoxy)ethanol, 2-(2-(2-aminoethoxy)ethoxy)ethanol and polyoxypropylenediamines having a mean molecular weight in the range from about 220 to 250 g/mol, such as, more particularly, Jeffamine® D-230.

Among these, preference is given to amines having one secondary and two primary amino groups, i.e. especially diethylenetriamine, dipropylenetriamine, N-(2-aminoethyl)propane-1,3-diamine (N3 amine) or bis(hexamethylene)triamine (BHMT). These amines can be converted to guanidines of the formula (II) having two guanidine groups, where X is $NR^3$ and $R^3$ is the radical of the formula

----$R^7$—Z.

In this way, catalysts of the formula (I) with particularly high activity are obtainable.

Among these, preference is further given to amines having one primary and one secondary and optionally one tertiary amino group, i.e. especially N-methylpropane-1,3-diamine, N-ethylpropane-1,3-diamine, N-butylethane-1,2-diamine, N-hexylethane-1,2-diamine, N-(2-ethylhexyl)ethane-1,2-diamine, N-cyclohexylethane-1,2-diamine, N-methylpropane-1,3-diamine, N-ethylpropane-1,3-diamine, N-butylpropane-1,3-diamine, N-hexylpropane-1,3-diamine, N-(2-ethylhexyl)propane-1,3-diamine, N-cyclohexylpropane-1,3-diamine, 4-aminomethylpiperidine, 4-((2-amino)ethyl)piperidine, N-(2-aminoethyl)piperazine or $N^1$-((3-dimethylamino)propyl)-1,3-diaminopropane. These amines can be converted particularly selectively to guanidines of the formula (II), which can in turn be converted further in a particularly simple manner to catalysts of the formula (I). Any tertiary amino groups present are advantageous in that they can further increase the catalytic activity.

The guanidine of the formula (II) for the reaction with at least one functional compound is preferably selected from the group consisting of 1-(2-aminoethyl)-2,3-diisopropylguanidine, 1-(2-aminoethyl)-2,3-dicyclohexylguanidine, 1-(2-aminopropyl)-2,3-diisopropylguanidine, 1-(2-aminopropyl)-2,3-dicyclohexylguanidine, 1-(3-aminopropyl)-2,3-diisopropylguanidine, 1-(3-aminopropyl)-2,3-dicyclohexylguanidine, 1-(2-methylaminoethyl)-2,3-diisopropylguanidine, 1-(2-methylaminoethyl)-2,3-dicyclohexylguanidine, 1-(2-ethylaminoethyl)-2,3-diisopropylguanidine, 1-(2-ethylaminoethyl)-2,3-dicyclohexylguanidine, 1-(2-cyclohexylaminoethyl)-2,3-diisopropylguanidine, 1-(2-cyclohexylaminoethyl)-2,3-dicyclohexylguanidine, 1-(3-methylaminopropyl)-2,3-diisopropylguanidine, 1-(3-methylaminopropyl)-2,3-dicyclohexylguanidine, 1-(3-ethylaminopropyl)-2,3-diisopropylguanidine, 1-(3-ethylaminopropyl)-2,3-dicyclohexylguanidine, 1-(3-cyclohexylaminopropyl)-2,3-diisopropylguanidine, 1-(3-cyclohexylaminopropyl)-2,3-dicyclohexylguanidine, 1-(3-aminopentyl)-2,3-diisopropylguanidine, 1-(3-aminopentyl)-2,3-dicyclohexylguanidine, 1-(5-amino-4-methylpentyl)-2,3-diisopropylguanidine, 1-(5-amino-4-methylpentyl)-2,3-dicyclohexylguanidine, 1-(5-amino-2-methylpentyl)-2,3-diisopropylguanidine, 1-(5-amino-2-methylpentyl)-2,3-dicyclohexylguanidine, 1-(6-aminohexyl)-2,3-diisopropylguanidine, 1-(6-aminohexyl)-2,3-dicyclohexylguanidine, 1-(6-amino-2,2(4),4-trimethylhexyl)-2,3-diisopropylguanidine, 1-(6-amino-2,2(4),4-trimethylhexyl)-2,3-dicyclohexylguanidine, 1-(6-amino-3,3(5),5-trimethylhexyl)-2,3-diisopropylguanidine, 1-(6-amino-3,3(5),5-trimethylhexyl)-2,3-dicyclohexylguanidine, 1-(8-aminooctyl)-2,3-diisopropylguanidine, 1-(8-aminooctyl)-2,3-dicyclohexylguanidine, 1-(12-aminododecyl)-2,3-diisopropylguanidine, 1-(12-aminododecyl)-2,3-dicyclohexylguanidine, 1-(3-aminomethyl-3,5,5-trimethylcyclohexyl)-2,3-diisopropylguanidine, 1-(3-aminomethyl-3,5,5-trimethylcyclohexyl)-2,3-dicyclohexylguanidine, 1-(3-amino-1,5,5-trimethylcyclohexylmethyl)-2,3-diisopropylguanidine, 1-(3-amino-1,5,5-trimethylcyclohexylmethyl)-2,3-dicyclohexylguanidine, 1-(3-aminomethylcyclohexyl)-2,3-diisopropylguanidine, 1-(3-aminomethylcyclohexyl)-2,3-dicyclohexylguanidine, 1-(3-aminomethylbenzyl)-2,3-diisopropylguanidine, 1-(3-aminomethylbenzyl)-2,3-dicyclohexylguanidine, 1-(3-amino-2(4)-methylcyclohexyl)-2,3-diisopropylguanidine, 1-(3-amino-2(4)-methylcyclohexyl)-2,3-dicyclohexylguanidine, 1,1'-(3-aza-1,5-pentylene)bis(2,3-diisopropylguanidine), 1-(piperidin-4-ylmethyl)-2,3-diisopropylguanidine, 1-(piperidin-4-ylmethyl)-2,3-dicyclohexylguanidine, 1-(2-(piperidin-4-yl)ethyl)-2,3-diisopropylguanidine, 1-(2-(piperidin-4-yl)ethyl)-2,3-dicyclohexylguanidine, 1-(2-piperazinoethyl)-2,3-diisopropylguanidine, 1-(2-piperazinoethyl)-2,3-dicyclohexylguanidine, 1,1'-(3-aza-1,5-pentylene)bis(2,3-dicyclohexylguanidine), 1,1'-(4-aza-1,7-heptylene)bis(2,3-diisopropylguanidine), 1,1'-(4-aza-1,7-heptylene)bis(2,3-dicyclohexylguanidine), 1,1'-(3-aza-1,6-hexylene)bis(2,3-diisopropylguanidine), 1,1'-(3-aza-1,6-hexylene)bis(2,3-dicyclohexylguanidine), 1,1'-(7-aza-1,13-tridecylene)bis(2,3-diisopropylguanidine), 1,1'-(7-aza-1,13-tridecylene)bis(2,3-dicyclohexylguanidine), 1-(3-((3-aminopropyl)(methyl)amino)propyl)-2,3-diisopropylguanidine, 1-(3-((3-aminopropyl)(methyl)amino)propyl)-2,3-dicyclohexylguanidine, 1-(3-((3-dimethylaminopropyl)amino)propyl)-2,3-diisopropylguanidine, 1-(3-((3-dimethylaminopropyl)amino)propyl)-2,3-dicyclohexylguanidine, 1-(5-amino-3-oxapentyl)-2,3-diisopropylguanidine, 1-(5-amino-3-oxapentyl)-2,3-dicyclohexylguanidine, 1-(8-amino-3,6-dioxadoctyl)-2,3-diisopropylguanidine, 1-(8-amino-3,6-dioxadoctyl)-2,3-dicyclohexylguanidine, 1-(10-amino-4,7-dioxadecyl)-2,3-diisopropylguanidine, 1-(10-amino-4,7-dioxadecyl)-2,3-dicyclohexylguanidine, 1-(2-hydroxyethyl)-2,3-diisopropylguanidine, 1-(2-hydroxyethyl)-2,3-dicyclohexylguanidine, 1-(2-hydroxypropyl)-2,3-diisopropylguanidine, 1-(2-hydroxypropyl)-2,3-dicyclohexylguanidine, 1-(3-hydroxypropyl)-2,3-diisopropylguanidine, 1-(3-hydroxypropyl)-2,3-dicyclohexylguanidine, 1-(2-hydroxy-1,1-dimethylethyl)-2,3-diisopropylguanidine, 1-(2-hydroxy-1,1-dimethylethyl)-2,3-dicyclohexylguanidine, 1-(5-hydroxypentyl)-2,3-diisopropylguanidine, 1-(5-hydroxypentyl)-2,3-dicyclohexylguanidine, 1-(6-hydroxyhexyl)-2,3-diisopropylguanidine, 1-(6-hydroxyhexyl)-2,3-dicyclohexylguanidine, 1-(3-hydroxy-1,5,5-trimethylcyclohexylmethyl)-2,3-diisopropylguanidine, 1-(3-hydroxy-1,5,5-trimethylcyclohexylmethyl)-2,3-dicyclohexylguanidine, 1-(2-(2-hydroxyethoxy)ethyl)-2,3-diisopropylguanidine, 1-(2-(2-hydroxyethoxy)ethyl)-2,3-dicyclohexylguanidine, 1-((2-(2-hydroxyethoxy)ethoxy)ethyl)-2,3-diisopropylguanidine, 1-((2-(2-hydroxyethoxy)ethoxy)ethyl)-2,3-dicyclohexylguanidine, 1-(ω-2-aminopropylpolyoxypropylene)-2,3-diisopropylguanidine having a molecular weight in the range from about 320 to 400 g/mol and 1-(ω-2-aminopropylpolyoxypropylene)-2,3-dicyclohexylguanidine having a molecular weight in the range from about 400 to 500 g/mol.

Among these, preference is given to the guanidines having a primary or secondary amino group. They can be reacted particularly easily with functional compounds and enable catalysts of the formula (I) with particularly high activity.

Among these, preference is further given to the guanidines having a hydroxyl group or a secondary amino group. They can be prepared in particularly pure form.

Preference is also given to guanidines having a tertiary amino group. They enable catalysts of the formula (I) with particularly high activity.

A catalyst of the formula (I) can also be obtained by, in a first step, reacting an amine of the formula (III) with one of the functional compounds described, with reaction of at least one of the reactive groups thereof with the HX group to give an amine intermediate, and, in a second step, reacting the latter with the reagent for introduction of guanidine groups to give a catalyst of the formula (I). This preparation is especially suitable for amines in which X is NH$_2$, i.e. for polyamines having two primary amino groups.

The first step is preferably conducted such that the primary amino groups of the amine are present in a stoichiometric excess relative to the reactive groups of the functional compound, so as to form an amine intermediate having a primary amino group.

The reaction conditions for the reagents involved in the respective reactions here are preferably the same as already described.

In a preferred catalyst of the formula (I), p is p$^1$, r is 0, Y is X$^2$, Q' is

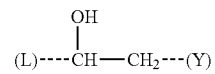

and L is L$^1$. The latter thus has the formula (I a)

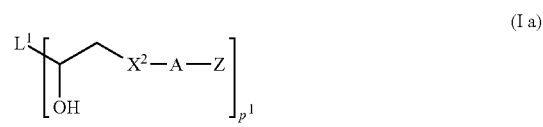

where
p$^1$ is an integer from 1 to 4,
L$^1$ is a p$^1$-valent hydrocarbyl radical which has a mean molecular weight in the range from 15 to 1'500 g/mol and which especially has one or more ether groups and optionally an alkoxysilane group,
X$^2$ is S or NR$^3$,
and A, R$^3$ and Z have the definitions described.
Preferably, p$^1$ is 1 or 2 or 3, more preferably 1 or 2.
Preferably, X$^2$ is NR$^3$.

A catalyst of the formula (I a) is especially obtained from the reaction of at least one guanidine of the formula (II) in which X is X$^2$ with at least one of the described functional compounds having at least one epoxy group. The reaction is preferably conducted at a temperature in the range from 20° C. to 140° C., especially 40° C. to 120° C.

In a further preferred catalyst of the formula (I), p is p$^2$, r is 0, Y is X$^1$, Q' is

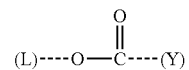

and L is L$^2$. The latter thus has the formula (I b)

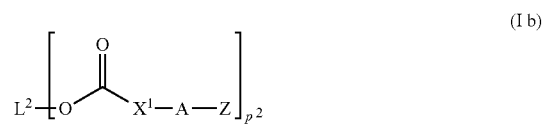

where
p$^2$ is 1 or 2,
X$^1$ is O or NR$^3$,
L$^2$ is an alkyl radical having 1 to 18 carbon atoms, and A, R$^3$ and Z have the definitions described.
Preferably, p$^2$ is 1.
Preferably, L$^2$ has a molecular weight in the range from 45 to 185 g/mol.

Preferably, $L^2$ is a hydroxyalkyl radical having 2 to 8 carbon atoms.

More preferably, $L^2$ is 2-hydroxyethyl, 2-hydroxypropyl or 3-hydroxypropyl, especially 2-hydroxypropyl.

A catalyst of the formula (I b) is especially obtained from the reaction of at least one guanidine of the formula (II) in which X is O or $NR^3$ with at least one dialkyl carbonate. The reaction is preferably conducted at a temperature in the range from 20° C. to 140° C., especially 40° C. to 120° C., and alcohols or phenols released are preferably removed during or after the reaction, especially by distillation under reduced pressure.

In a further preferred catalyst of the formula (I), p is $p^3$, r is 0, Y is Q' is

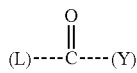

and L is $L^3$. The latter thus has the formula (I c)

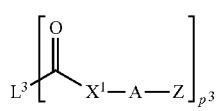

(I c)

where
$p^3$ is 1 or 2 or 3,
$X^1$ is O or $NR^3$,
$L^3$ is a covalent bond or a hydrogen radical or a $p^3$-valent hydrocarbyl radical which has a mean molecular weight in the range from 14 to 500 g/mol and optionally has unsaturated components and optionally ether groups or ester groups,
and A, $R^3$ and Z have the definitions described.

Preferably, $p^3$ is 1 or 2, especially 1.

A catalyst of the formula (I c) is especially obtained from the reaction of at least one guanidine of the formula (II) in which X is O or $NR^3$ with at least one of the described functional compounds having at least one carboxylic ester group.

The reaction is preferably conducted at a temperature in the range from 20° C. to 160° C., especially 40° C. to 140° C. The elimination products formed in the reaction, in the form of alcohols or phenols, are preferably removed during or after the reaction, especially by distillation under reduced pressure.

In a further preferred catalyst of the formula (I), p is 1, r is 0, Y is $X^1$, Q' is

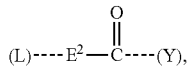

$E^2$ is $CH(OH)$—$(CH_2)_b$ or $CH(OH)$—$(CH_2)_c O$ and L is $L^4$. The latter thus has the formula (I d) or (I e)

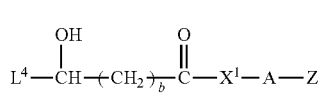

(I d)

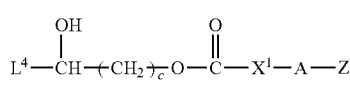

(I e)

where
$X^1$ is O or $NR^3$,
b is an integer in the range from 1 to 4,
c is 1 or 2,
$L^4$ is a hydrogen radical or a linear alkyl radical having 1 to 12 carbon atoms, and A, $R^3$ and Z have the definitions described.

Preferably, b is 2 or 3 or 4.
Preferably, c is 1.

In the case of formula (I d), $L^4$ is preferably a hydrogen radical or a linear alkyl radical having 1 to 8 carbon atoms, especially a hydrogen radical or a methyl radical.

In the case of formula (I e), $L^4$ is preferably a hydrogen radical or a methyl radical, especially a methyl radical.

A catalyst of the formula (I d) is especially obtained from the reaction of at least one guanidine of the formula (II) in which X is O or $NR^3$ with at least one of the lactones described.

A catalyst of the formula (I e) is especially obtained from the reaction of at least one guanidine of the formula (II) in which X is O or $NR^3$ with at least one of the cyclic carbonates described.

The reaction is preferably conducted at a temperature in the range from 20° C. to 140° C., especially 40° C. to 120° C.

In a further preferred catalyst of the formula (I), p is $p^5$, r is 0, Y is N, Q' is

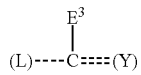

and L is $L^5$. The latter thus has the formula (I f)

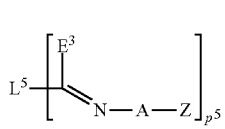

(I f)

where
$p^5$ is 1 or 2 or 3,
$L^5$ is a monovalent hydrocarbyl radical which has 1 to 20 carbon atoms and optionally contains heteroatoms, especially oxygen or nitrogen in the form of ester groups, amide groups, ether groups or tertiary amino groups, or together with $E^3$ is an optionally substituted 1,4-butylene or 1,5-pentylene radical, and A and Z have the definitions described.

Preferably, $p^5$ is 1 or 2, especially 1.

Preferably, $E^3$ is a hydrogen radical or is a methyl radical.

If $E^3$ is a hydrogen radical, $L^5$ is preferably prop-2-yl, hept-3-yl, undec-1-yl, phenyl, 1,1-dimethyl-2-acetoxyeth-1-yl, 1,1-dimethyl-2-lauroyloxyeth-1-yl, 1,1-dimethyl-2-(N-morpholino)eth-1-yl, 2-bis(methoxyethyl)amino-1,1-dimethyleth-1-yl or 2-bis(2-hydroxypropyl)amino-1,1-dimethyleth-1-yl.

If $E^3$ is a methyl radical, $L^5$ is preferably methyl, ethyl, prop-2-yl, 2-methylprop-1-yl, benzyl.

A catalyst of the formula (I f) is especially obtained from the reaction of at least one guanidine of the formula (II) in which X is NH with at least one of the described functional compounds having at least one ketone or aldehyde group. The reaction is preferably conducted at a temperature in the range from 0° C. to 120° C., especially 20° C. to 100° C. The water formed in the reaction is preferably removed during or after the reaction, especially by azeotropic distillation or distillation under reduced pressure.

In a further preferred catalyst of the formula (I), p is $p^6$, r is 0, Y is Q' is

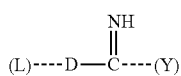

and L is $L^6$. The latter thus has the formula (I g)

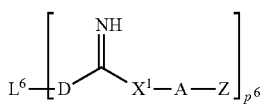

where
$p^6$ is an integer from 1 to 3,
$X^1$ is O or $NR^3$,
$L^6$ is a $p^6$-valent hydrocarbyl radical which has a mean molecular weight in the range from 77 to 5'000 g/mol and which optionally contains heteroatoms, especially oxygen in the form of ether groups or ester groups, or has fluorine atoms,
and D, A, $R^3$ and Z have the definitions described.
Preferably, $p^6$ is 2 or 3, especially 2.

A catalyst of the formula (I g) is especially obtained from the reaction of at least one guanidine of the formula (II) in which X is O or $NR^3$ with at least one of the described functional compounds having at least one cyanate or thiocyanate group. The reaction is preferably conducted at a temperature in the range from 20° C. to 150° C.

In a further preferred catalyst of the formula (I), p is $p^7$, r is 0, Y is $X^1$, Q' is

and L is $L^7$. The latter thus has the formula (I h)

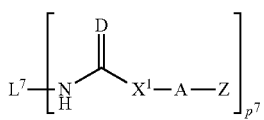

where
$p^7$ is an integer from 1 to 4,
$X^1$ is O or $NR^3$,
$L^7$ is a $p^7$-valent hydrocarbyl radical which has a mean molecular weight in the range from 15 to 20'000 g/mol and which optionally contains heteroatoms, especially in the form of ether groups, ester groups, amide groups, urethane groups, isocyanurate groups, cyanurate groups, isocyanate groups or alkoxysilane groups,
and D, A, $R^3$ and Z have the definitions described.
Preferably, $p^7$ is 1 or 2 or 3.

A catalyst of the formula (I h) is especially obtained from the reaction of at least one guanidine of the formula (II) in which X is O or $NR^3$ with at least one of the described functional compounds having at least one isocyanate or isothiocyanate group. The reaction is preferably conducted at a temperature in the range from 0° C. to 120° C. If X is $NR^3$, preference is given to a temperature in the range from 0° C. to 80° C. If X is O, preference is given to a temperature in the range from 40° C. to 120° C.

In a further preferred catalyst of the formula (I), p is $p^8$, r is 0, Y is $NR^3$, Q' is

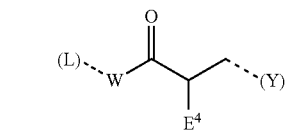

and L is $L^8$. The latter thus has the formula (I i)

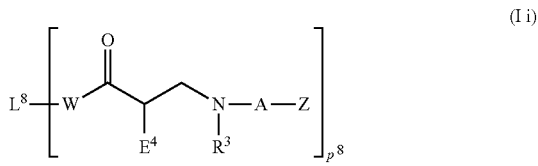

where
$p^8$ is an integer from 1 to 3,
$L^8$ is a hydrogen radical or a $p^8$-valent hydrocarbyl radical which has a mean molecular weight in the range from 14 to 20'000 g/mol and which optionally contains heteroatoms, especially in the form of ether groups, ester groups, urethane groups, isocyanurate groups, cyanurate groups or alkoxysilane groups,
and W, $E^4$, A, $R^3$ and Z have the definitions described.
Preferably, $p^8$ is 1 or 2, especially 1.

A catalyst of the formula (I i) is especially obtained from the reaction of at least one guanidine of the formula (II) in which X is $NR^3$ with at least one of the described functional compounds having at least one acrylate, methacrylate, acrylamide, methacrylamide, fumarate, fumaramide, itaconate or itaconamide group. The reaction is preferably conducted at a temperature in the range from 0° C. to 140° C., especially 20° C. to 120° C.

In a further preferred catalyst of the formula (I), p is $p^9$, r is 0, Y is N, Q' is

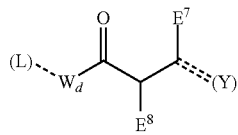

and L is $L^9$. The latter thus has the formula (I j)

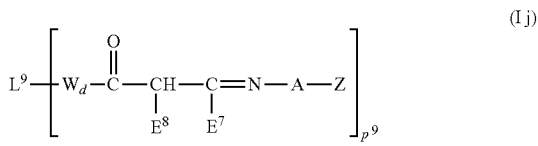

where
$p^9$ is 1 or 2 or 3,
$L^9$ is a $p^9$-valent hydrocarbyl radical which has a mean molecular weight in the range from 15 to 5'000 g/mol and which optionally contains heteroatoms, especially in the form of ether groups or ester groups, and d, W, $E^7$, $E^8$, A and Z have the definitions described. Preferably, $p^9$ is 1 or 2, especially 1.

A catalyst of the formula (I j) is especially obtained from the reaction of at least one guanidine of the formula (II) in which X is NH with at least one of the described functional compounds having at least one 1,3-diketone or 1,3-keto ester or 1,3-keto amide group. The reaction is preferably conducted at a temperature in the range from 0° C. to 120° C., especially 20° C. to 100° C. The water formed in the reaction is preferably removed during or after the reaction, especially by azeotropic distillation or distillation under reduced pressure.

The catalyst of the formula (I) is used for the crosslinking of a curable composition, where it accelerates the crosslinking or curing of the composition.

A suitable curable composition is especially an epoxy resin composition, especially high-temperature-curing systems that crosslink via dicyandiamide or carboxylic acids or carboxylic anhydrides, as used, for example, in adhesives, coatings and casting resins;

or a polyurethane composition, especially two-component systems that crosslink by reaction of polyols with isocyanates, as used, for example, for adhesives, coverings, potting compounds, sealing joints, moldings or slabstock foams, and also one-component systems having blocked isocyanate groups or blocked amino groups, as used, for example, in powder coatings, coil coatings, electrocoat materials and liquid paints;

or an epoxy resin-polyurethane composition;

or a cyanate ester resin composition;

or a composition containing silane groups.

A particularly advantageous use is for crosslinking of compositions containing silane groups, especially of compositions based on polymers containing silane groups. Compositions based on polymers containing silane groups cure rapidly even when the catalyst concentration is relatively low and do not have a tendency to migration-related defects such as separation, exudation or substrate soiling.

The polymer containing silane groups is especially selected from the group consisting of polyorganosiloxanes having terminal silane groups and organic polymers containing silane groups, as described more specifically hereinafter. A polyorganosiloxane having terminal silane groups has the advantage that, in the cured state, it is particularly water- and light-stable and enables particularly flexible properties.

An organic polymer containing silane groups has the advantage of having particularly good adhesion properties on a multitude of substrates and being particularly inexpensive.

The invention thus further provides a curable composition comprising at least one catalyst of the formula (I).

Preferably, the curable composition is an adhesive or a sealant or a coating.

Preferably, the curable composition further comprises at least one polymer containing silane groups.

A composition of this kind typically has good storability with no propensity to separation, and because of the low toxicity and low volatility of the catalyst of the formula (I) allows a low hazard classification and enables low-emissions and low-odor products that cure rapidly and at the same time form a mechanically high-quality and durable material. A particularly advantageous circumstance here is that this material shows barely any propensity to migration-related defects such as exudation or substrate soiling, by contrast with compositions comprising catalysts according to the prior art, for example DBU or TMG. Compositions comprising such catalysts known from the prior art have a propensity to migration effects, which can be manifested prior to curing by separation and after curing by tacky and/or greasy surfaces and/or substrate soiling. Particularly the latter effects are extremely undesirable, since tacky and greasy surfaces are rapidly soiled and are difficult to paint over, and substrate contaminants can lead to lasting discoloration.

In a preferred embodiment, the polymer containing silane groups is a polyorganosiloxane having terminal silane groups.

A preferred polyorganosiloxane having terminal silane groups has the formula (IV)

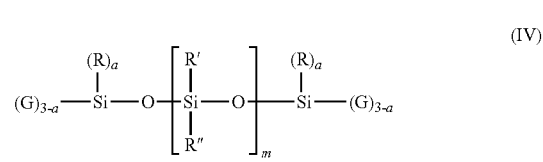

where

R, R' and R" are each independently a monovalent hydrocarbyl radical having 1 to 12 carbon atoms;

G is a hydroxyl radical or an alkoxy, acetoxy, ketoximato, amido or enoxy radical having 1 to 13 carbon atoms;

a is 0, 1 or 2; and m is an integer in the range from 50 to about 2'500.

R is preferably methyl, vinyl or phenyl.

R' and R" are preferably each independently an alkyl radical having 1 to 5, preferably 1 to 3, carbon atoms, especially methyl.

G is preferably a hydroxyl radical or an alkoxy or ketoximato radical having 1 to 6 carbon atoms, especially a hydroxyl, methoxy, ethoxy, methylethylketoximato or methylisobutylketoximato radical.

More preferably, G is a hydroxyl radical.

a is preferably 0 or 1, especially 0.

In addition, m is preferably chosen such that the polyorganosiloxane of the formula (IV) has a viscosity at room temperature in the range from 100 to 500'000 mPa·s, especially from 1000 to 100'000 mPa·s.

Polyorganosiloxanes of the formula (IV) are easy to handle and crosslink with moisture and/or silane crosslinkers to give solid silicone polymers having elastic properties.

Suitable commercially available polyorganosiloxanes of the formula (IV) are available, for example, from Wacker, Momentive Performance Material, GE Advanced Materials, Dow Corning, Bayer or Shin Etsu.

Preferably, the composition comprises, in addition to the polyorganosiloxane having terminal silane groups, a silane crosslinker, especially a silane of the formula (V),

where

R'" is a monovalent hydrocarbyl radical having 1 to 12 carbon atoms,

G' is a hydroxyl radical or is an alkoxy, acetoxy, ketoximato, amido or enoxy radical having 1 to 13 carbon atoms; and q has a value of 0, 1 or 2, especially 0 or 1.

Particularly suitable silanes of the formula (V) are methyltrimethoxysilane, ethyltrimethoxysilane, propyltrimethoxysilane, vinyltrimethoxysilane, methyltriethoxysilane, vinyltriethoxysilane, phenyltriethoxysilane, tetramethoxysilane, tetraethoxysilane, methyltris(methylethylketoximo)silane, vinyltris(methylethylketoximo)silane and methyltris(isobutylketoximo)silane.

In a further preferred embodiment, the polymer containing silane groups is an organic polymer containing silane groups, especially a polyolefin, polyester, polyamide, poly(meth)acrylate or polyether or a mixed form of these polymers, each of which bears one or preferably more than one silane group. The silane groups may be in pendant positions in the chain or in terminal positions and are bonded to the organic polymer via a carbon atom.

More preferably, the organic polymer containing silane groups is a polyolefin containing silane groups or a polyester containing silane groups or a poly(meth)acrylate containing silane groups or a polyether containing silane groups or a mixed form of these polymers.

Most preferably, the organic polymer containing silane groups is a polyether containing silane groups.

The silane groups present in the organic polymer containing silane groups are preferably alkoxysilane groups, especially alkoxysilane groups of the formula (VI)

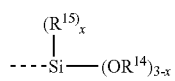
(VI)

where $R^{14}$ is a linear or branched, monovalent hydrocarbyl radical having 1 to 5 carbon atoms, especially methyl or ethyl or isopropyl;

$R^{15}$ is a linear or branched, monovalent hydrocarbyl radical having 1 to 8 carbon atoms, especially methyl or ethyl; and x as a value of 0 or 1 or 2, preferably 0 or 1, especially 0.

More preferably $R^{14}$ is methyl or ethyl.

For particular applications, the $R^{14}$ radical is preferably an ethyl group, since, in this case, ecologically and toxicologically harmless ethanol is released in the course of curing of the composition.

Particular preference is given to trimethoxysilane groups, dimethoxymethyl-silane groups or triethoxysilane groups.

In this context, methoxysilane groups have the advantage that they are particularly reactive, and ethoxysilane groups have the advantage that they are toxicologically advantageous and particularly storage-stable.

The organic polymer containing silane groups has an average of preferably 1.3 to 4, especially 1.5 to 3, more preferably 1.7 to 2.8, silane groups per molecule.

The silane groups are preferably terminal.

The organic polymer containing silane groups preferably has a mean molecular weight, determined by means of GPC against a polystyrene standard, in the range from 1'000 to 30'000 g/mol, especially from 2'000 to 20'000 g/mol. The organic polymer containing silane groups preferably has a silane equivalent weight of 300 to 25'000 g/eq, especially of 500 to 15'000 g/eq.

The organic polymer containing silane groups may be solid or liquid at room temperature. It is preferably liquid at room temperature.

Most preferably, the organic polymer containing silane groups is a polyether containing silane groups which is liquid at room temperature, where the silane groups are especially dialkoxysilane groups and/or trialkoxysilane groups, more preferably trimethoxysilane groups or triethoxysilane groups.

Processes for preparing polyethers containing silane groups are known to the person skilled in the art.

In a preferred process, polyethers containing silane groups are obtainable from the reaction of polyethers containing allyl groups with hydrosilanes, optionally with chain extension using, for example, diisocyanates.

In a further preferred process, polyethers containing silane groups are obtainable from the copolymerization of alkylene oxides and epoxysilanes, optionally with chain extension using, for example, diisocyanates.

In a further preferred process, polyethers containing silane groups are obtainable from the reaction of polyether polyols with isocyanatosilanes, optionally with chain extension using diisocyanates.

In a further preferred process, polyethers containing silane groups are obtainable from the reaction of polyethers containing isocyanate groups, especially NCO-terminated urethane polyethers from the reaction of polyether polyols with a superstoichiometric amount of polyisocyanates, with aminosilanes, hydroxysilanes or mercaptosilanes. Polyethers containing silane groups from this process are particularly preferred. This process enables the use of a multitude of inexpensive starting materials of good commercial availability, by means of which it is possible to obtain different polymer properties, for example high extensibility, high strength, low modulus of elasticity, low glass transition point or high weathering resistance.

More preferably, the polyether containing silane groups is obtainable from the reaction of NCO-terminated urethane polyethers with aminosilanes or hydroxysilanes. Suitable NCO-terminated urethane polyethers are obtainable from the reaction of polyether polyols, especially polyoxyalkylenediols or polyoxyalkylenetriols, preferably polyoxypropylenediols or polyoxypropylenetriols, with a superstoichiometric amount of polyisocyanates, especially diisocyanates.

Preferably, the reaction between the polyisocyanate and the polyether polyol is conducted with exclusion of moisture at a temperature of 50° C. to 160° C., optionally in the presence of suitable catalysts, with metered addition of the polyisocyanate in such a way that the isocyanate groups thereof are present in a stoichiometric excess in relation to the hydroxyl groups of the polyol. More particularly, the excess of polyisocyanate is chosen such that a content of free isocyanate groups of 0.1% to 5% by weight, preferably 0.2% to 4% by weight, more preferably 0.3% to 3% by weight, based on the overall polymer, remains in the resulting urethane polyether after the reaction of all hydroxyl groups.

Preferred diisocyanates are selected from the group consisting of hexamethylene 1,6-diisocyanate (HDI), 1-isocyanato-3,3,5-trimethyl-5-isocyanatomethylcyclohexane (=isophorone diisocyanate or IPDI), tolylene 2,4- and 2,6-diisocyanate and any desired mixtures of these isomers (TDI) and diphenylmethane 4,4'-, 2,4'- and 2,2'-diisocyanate and any desired mixtures of these isomers (MDI). Particular preference is given to IPDI or TDI. Most preferred is IPDI. In this way, polyethers containing silane groups with particularly good lightfastness are obtained.

Especially suitable as polyether polyols are polyoxyalkylenediols or polyoxyalkylenetriols having a degree of unsaturation lower than 0.02 meq/g, especially lower than 0.01 meq/g, and a mean molecular weight in the range from 400 to 25'000 g/mol, especially 1000 to 20'000 g/mol.

As well as polyether polyols, it is also possible to use portions of other polyols, especially polyacrylate polyols, and low molecular weight diols or triols.

Suitable aminosilanes for the reaction with an NCO-terminated urethane polyether are primary and secondary aminosilanes. Preference is given to 3-aminopropyltrimethoxysilane, 3-aminopropyldimethoxymethylsilane, 4-aminobutyltrimethoxysilane, 4-amino-3-methylbutyltrimethoxysilane, 4-amino-3,3-dimethylbutyltrimethoxysilane, N-butyl-3-aminopropyltrimethoxysilane, N-phenyl-3-aminopropyltrimethoxysilane, adducts formed from primary amino-silanes such as 3-aminopropyltrimethoxysilane, 3-aminopropyldimethoxy-methylsilane or N-(2-aminoethyl)-3-aminopropyltrimethoxysilane and Michael acceptors such as acrylonitrile, (meth)acrylic esters, (meth)acrylamides, maleic or fumaric diesters, citraconic diesters or itaconic diesters, especially dimethyl or diethyl N-(3-trimethoxysilylpropyl)aminosuccinate. Likewise suitable are analogs of the aminosilanes mentioned with ethoxy or isopropoxy groups in place of the methoxy groups on the silicon.

Suitable hydroxysilanes for the reaction with an NCO-terminated urethane polyether are especially obtainable from the addition of aminosilanes onto lactones or onto cyclic carbonates or onto lactides.

Aminosilanes suitable for the purpose are especially 3-aminopropyltrimeth-oxysilane, 3-aminopropyltriethoxysilane, 4-aminobutyltrimethoxysilane, 4-aminobutyltriethoxysilane, 4-amino-3-methylbutyltrimethoxysilane, 4-amino-3-methylbutyltriethoxysilane, 4-amino-3,3-dimethylbutyltrimethoxysilane, 4-amino-3,3-dimethylbutyltriethoxysilane, 2-aminoethyltrimethoxysilane or 2-aminoethyltriethoxysilane. Particular preference is given to 3-aminopropyltrimethoxysilane, 3-aminopropyltriethoxysilane, 4-amino-3,3-dimethylbutyl-trimethoxysilane or 4-amino-3,3-dimethylbutyltriethoxysilane.

Suitable lactones are especially γ-valerolactone, γ-octalactone, δ-decalactone, and ε-decalactone, especially γ-valerolactone.

Suitable cyclic carbonates are especially 4,5-dimethyl-1,3-dioxolan-2-one, 4,4-dimethyl-1,3-dioxolan-2-one, 4-ethyl-1,3-dioxolan-2-one, 4-methyl-1,3-dioxolan-2-one or 4-(phenoxymethyl)-1,3-dioxolan-2-one.

Suitable lactides are especially 1,4-dioxane-2,5-dione (lactide formed from 2-hydroxyacetic acid, also called "glycolide"), 3,6-dimethyl-1,4-dioxane-2,5-dione (lactide formed from lactic acid, also called "lactide") and 3,6-diphenyl-1,4-dioxane-2,5-dione (lactide formed from mandelic acid).

Preferred hydroxysilanes which are obtained in this way are N-(3-triethoxysilylpropyl)-2-hydroxypropanamide, N-(3-trimethoxysilylpropyl)-2-hydroxypropanamide, N-(3-triethoxysilylpropyl)-4-hydroxypentanamide, N-(3-triethoxysilylpropyl)-4-hydroxyoctanamide, N-(3-triethoxysilylpropyl)-5-hydroxydecanamide and N-(3-triethoxysilylpropyl)-2-hydroxypropyl carbamate.

In addition, suitable hydroxysilanes are also obtainable from the addition of aminosilanes onto epoxides or from the addition of amines onto epoxysilanes. Preferred hydroxysilanes which are obtained in this way are 2-morpholino-4(5)-(2-trimethoxysilylethyl)cyclohexan-1-ol, 2-morpholino-4(5)-(2-triethoxysilyl-ethyl)cyclohexan-1-ol or 1-morpholino-3-(3-(triethoxysilyl)propoxy)propan-2-ol.

Further suitable polyethers containing silane groups are commercially available products, especially the following: MS Polymer™ (from Kaneka Corp.; especially the S203H, S303H, S227, S810, MA903 and S943 products); MS Polymer™ or Silyl™ (from Kaneka Corp.; especially the SAT010, SAT030, SAT200, SAX350, SAX400, SAX725, MAX450, MAX951 products); Excestar® (from Asahi Glass Co. Ltd.; especially the S2410, S2420, S3430, S3630 products); SPUR+* (from Momentive Performance Materials; especially the 1010LM, 1015LM, 1050MM products); Vorasil™ (from Dow Chemical Co.; especially the 602 and 604 products); Desmoseal® (from Bayer MaterialScience AG; especially the S XP 2458, S XP 2636, S XP 2749, S XP 2774 and S XP 2821 products), TEGOPAC® (from Evonik Industries AG; especially the Seal 100, Bond 150, Bond 250 products), Polymer ST (from Hanse Chemie AG/Evonik Industries AG, especially the 47, 48, 61, 61LV, 77, 80, 81 products); Geniosil® STP (from Wacker Chemie AG; especially the E10, E15, E30, E35 products).

Particularly preferred organic polymers containing silane groups have end groups of the formula (VII)

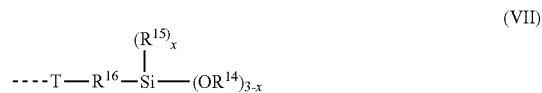

where

R$^{16}$ is a linear or branched divalent hydrocarbyl radical which has 1 to 12 carbon atoms and optionally has cyclic and/or aromatic moieties and optionally one or more heteroatoms, especially one or more nitrogen atoms;

T is a divalent radical selected from —O—, —S—, —N(R$^{17}$)—, —O—CO—N(R$^{17}$)—, —N(R$^{17}$)—CO—O— and —N(R$^{17}$)—CO—N(R$^{17}$)—, where R$^{17}$ is a hydrogen radical or a linear or branched hydrocarbyl radical which has 1 to 20 carbon atoms and optionally has cyclic moieties, and which optionally has an alkoxysilane, ether or carboxylic ester group; and R$^{14}$, R$^{15}$ and x have the definitions already given.

Preferably, R$^{16}$ is 1,3-propylene or 1,4-butylene, where butylene may be substituted by one or two methyl groups.

More preferably, R$^{16}$ is 1,3-propylene.

Preferably, the catalyst of the formula (I) is present in the composition in such an amount that the concentration of guanidine groups based on the amount of the polymer containing silane groups is in the range from 0.05 to 20 mmol/100 g of polymer, preferably 0.1 to 15 mmol/100 g of polymer, especially 0.1 to 10 mmol/100 g.

Such a composition has good storability and rapid curing.

In addition to the catalyst of the formula (I), the composition may comprise further catalysts, especially for the crosslinking of the silane groups. Suitable further catalysts are especially metal compounds and/or basic nitrogen or phosphorus compounds.

Suitable metal compounds are especially compounds of tin, titanium, zirconium, aluminum or zinc, especially diorganotin(IV) compounds such as, in particular, dibutyltin(IV) diacetate, dibutyltin(IV) dilaurate, dibutyltin(IV) dineodecanoate or dibutyltin(IV) bis(acetylacetonate) and dioctyltin (IV) dilaurate, and also titanium(IV) or zirconium(IV) or aluminum(III) or zinc(II) complexes, especially with alkoxy, carboxylate, 1,3-diketonate, 1,3-ketoesterate or 1,3-ketoamidate ligands.

Suitable basic nitrogen or phosphorus compounds are especially imidazoles, pyridines, phosphazene bases or preferably amines, hexahydrotriazines, biguanides, amidines or further guanidines.

Suitable amines are especially alkyl-, cycloalkyl- or aralkylamines such as triethylamine, triisopropylamine, 1-butylamine, 2-butylamine, tert-butylamine, 3-methyl-1-butylamine, 3-methyl-2-butylamine, dibutylamine, tributylamine, hexylamine, dihexylamine, cyclohexylamine, dicyclohexylamine, dimethylcyclohexylamine, benzylamine, dibenzylamine, dimethylbenzylamine, octylamine, 2-ethylhexylamine, di-(2-ethylhexyl)amine, laurylamine, N,N-dimethyllaurylamine, stearylamine, N,N-dimethylstearylamine; fatty amines derived from natural fatty acid mixtures, such as, more particularly, cocoalkylamine, N,N-dimethylcocoalkylamine, $C_{16-22}$-alkylamine, N,N-dimethyl-$C_{16-22}$-alkylamine, soyaalkylamine, N,N-dimethylsoyaalkylamine, oleylamine, N,N-dimethyloleylamine, tallowalkylamine or N,N-dimethyltallowalkylamine, obtainable, for example, under the Armeen® (from Akzo Nobel) or Rofamin® (from Ecogreen Oleochemicals) trade names; aliphatic, cycloaliphatic or araliphatic diamines such as ethylenediamine, butanediamine, hexamethylenediamine, dodecanediamine, neopentanediamine, 2-methyl-pentamethylenediamine (MPMD), 2,2(4),4-trimethylhexamethylenediamine (TMD), isophoronediamine (IPD), 2,5(2,6)-bis-(aminomethyl)bicyclo[2.2.1]-heptane (NBDA), 1,3-xylylenediamine (MXDA), N,N'-di(tert-butyl)ethylenediamine, N,N,N',N'-tetramethylethylenediamine, N,N,N',N'-tetramethyl-propylenediamine, N,N,N',N'-tetramethylhexamethylenediamine, 3-dimethylaminopropylamine, 3-(methylamino)propylamine, 3-(cyclohexylamino)-propylamine, piperazine, N-methylpiperazine, N,N'-dimethylpiperazine, 1,4-diazabicyclo[2.2.2]octane, fatty polyamines such as N-cocoalkyl-1,3-propane-diamine, N-oleyl-1,3-propanediamine, N-soyaalkyl-1,3-propanediamine, N-tallowalkyl-1,3-propanediamine or N—($C_{16-22}$-alkyl)-1,3-propanediamine, obtainable, for example, under the Duomeen® trade name (from Akzo Nobel); polyalkyleneamines such as diethylenetriamine, dipropylenetriamine, triethylenetetramine (TETA), tetraethylenepentamine (TEPA), pentamethylenehexamine (PEHA), 3-(2-aminoethyl)aminopropylamine, N,N'-bis(3-amino-propyl)ethylenediamine, N-(3-aminopropyl)-N-methylpropanediamine, bis(3-dimethylaminopropyl)amine, N-(3-dimethylaminopropyl)-1,3-propylenediamine, N-(2-aminoethyl)piperazine (N-AEP), N-(2-aminopropyl)piperazine, N,N'-di-(2-aminoethyl)piperazine, 1-methyl-4-(2-dimethylaminoethyl)piperazine, N,N,N',N'',N'''-pentamethyldiethylenetriamine, N,N,N',N'',N'''-pentamethyldipropylenetriamine, polyethyleneimines, obtainable, for example, under the Lupasol® (from BASF) and Epomin® (from Nippon Shokubai) trade names; etheramines such as, more particularly, 2-methoxyethylamine, 2-ethoxyethylamine, 3-methoxypropylamine, 3-ethoxypropylamine, 3-(2-ethylhexyloxy)propylamine, 3-(2-methoxyethoxy)propylamine, 2(4)-methoxyphenylethylamine, morpholine, N-methylmorpholine, N-ethyl-morpholine, 2-aminoethylmorpholine, bis(2-aminoethyl) ether, bis(dimethyl-aminoethyl) ether, bis(dimorpholinoethyl) ether, N,N,N'-trimethyl-N'-hydroxyethylbis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine or 2-aminopropyl-terminated glycols as obtainable, for example, under the Jeffamine® trade name (from Huntsman); amino alcohols such as, more particularly, ethanolamine, isopropanolamine, diethanolamine, diisopropanolamine, triethanolamine, triisopropanolamine, N-butylethanolamine, diglycolamine, N,N-diethylethanolamine, N-methyldiethanolamine, N-methyldiisopropylamine, N,N, N'-trimethylaminoethylethanolamine, N-(3-dimethylaminopropyl)-N,N-diisopropanolamine, N,N-bis(3-dimethylaminopropyl)-N-isopropanolamine, 2-(2-dimethylaminoethoxy)ethanolamine or adducts formed from mono- and polyamines with epoxides or diepoxides; amines containing phenol groups, such as, more particularly, condensation products formed from phenols, aldehydes and amines (what are called Mannich bases and phenalkamines), such as, more particularly, 2-(dimethylaminomethyl)phenol, 2,4,6-tris(dimethyl-aminomethyl)phenol or polymers formed from phenol, formaldehyde and N,N-dimethyl-1,3-propanediamine, and also phenalkamines commercially available under the Cardolite® (from Cardolite), Aradur® (from Huntsman) and Beckopox® (from Cytec) brand names; polyamines containing amide groups, called polyamidoamines, as commercially available, for example, under the Versamid® (from Cognis), Aradur® (from Huntsman), Euretek® (from Huntsman) or Beckopox® (from Cytec) brand names; or aminosilanes such as, more particularly 3-aminopropyltrimethoxysilane, 3-aminopropyldimethoxy-methylsilane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)propyl]ethylenediamine or analogs thereof with ethoxy in place of the methoxy groups on the silicon.

Suitable hexahydrotriazines are especially 1,3,5-hexahydrotriazine or 1,3,5-tris(3-(dimethylamino)propyl)hexahydrotriazine.

Suitable biguanides are especially biguanide, 1-butylbiguanide, 1,1-dimethylbiguanide, 1-butylbiguanide, 1-phenylbiguanide or 1-(o-tolyl)biguanide (OTBG).

Suitable amidines are especially 1,8-diazabicyclo[5.4.0]undec-7-ene (DBU), 1,5-diazabicyclo[4.3.0]non-5-ene (DBN), 6-dibutylamino-1,8-diaza-bicyclo[5.4.0]undec-7-ene, 6-dibutylamino-1,8-diazabicyclo[5.4.0]undec-7-ene, N,N'-di-n-hexylacetamidine (DHA), 2-methyl-1,4,5,6-tetrahydropyrimidine, 1,2-dimethyl-1,4,5,6-tetrahydropyrimidine, 2,5,5-trimethyl-1,4,5,6-tetrahydro-pyrimidine, N-(3-trimethoxysilylpropyl)-4,5-dihydroimidazole or N-(3-triethoxy-silylpropyl)-4,5-dihydroimidazole.

Suitable further guanidines are especially 1-butylguanidine, 1,1-dimethylguanidine, 1,3-dimethylguanidine, 1,1,3,3-tetramethylguanidine (TMG), 2-(3-(trimethoxysilyl)propyl)-1,1,3,3-tetramethylguanidine, 2-(3-(methyldimethoxysilyl)propyl)-1,1,3,3-tetramethylguanidine, 2-(3-(triethoxysilyl)propyl)-1,1,3,3-tetramethyl-guanidine, 1,5,7-triazabicyclo-[4.4.0]dec-5-ene (TBD), 7-methyl-1,5,7-triazabicyclo[4.4.0]dec-5-ene, 7-cyclohexyl-1,5,7-triazabicyclo[4.4.0]dec-5-ene, 1-phenylguanidine, 1-(o-tolyl)guanidine (OTG), 1,3-diphenylguanidine, 1,3-di(o-tolyl)guanidine or 2-guanidinobenzimidazole.

In addition, the composition may comprise, as cocatalyst, an acid, especially a carboxylic acid. Preference is given to aliphatic carboxylic acids such as formic acid, lauric acid, stearic acid, isostearic acid, oleic acid, 2-ethyl-2,5-dimethylcaproic acid, 2-ethylhexanoic acid, neodecanoic acid, fatty acid mixtures from the hydrolysis of natural fats and oils or di- and polycarboxylic acids, especially poly(meth)acrylic acids.

In a preferred embodiment, the composition is essentially free of organotin compounds. Organotin-free compositions are advantageous in terms of protection of health and protection of the environment. More particularly, the tin content of the curable composition is less than 0.1% A by weight, especially less than 0.05% by weight.

In a further preferred embodiment, the composition comprises a combination of at least one catalyst of the formula (I) and at least one organotin compound, especially a diorganotin(IV) compound such as those mentioned above. Such a composition has a high curing rate even in the case of a low tin content, which is advantageous for toxicological and environmental reasons.

In one embodiment, the composition additionally comprises, as well as the catalyst of the formula (I), at least one organotitanate. A combination of the catalyst described and an organotitanate has particularly high catalytic activity. This enables rapid curing of such a composition with a comparatively small use amount of organotitanate.

Suitable organotitanates are especially titanium(IV) complexes.

Preferred organotitanates are especially selected from titanium(IV) complexes having two 1,3-diketonate ligands, especially 2,4-pentanedionate (=acetylacetonate), and two alkoxide ligands;

titanium(IV) complexes having two 1,3-ketoesterate ligands, especially ethylacetoacetate, and two alkoxide ligands;

titanium(IV) complexes having one or more aminoalkoxide ligands, especially triethanolamine or 2-((2-aminoethyl)amino)ethanol, and one or more alkoxide ligands;

titanium(IV) complexes having four alkoxide ligands;

and more highly condensed organotitanates, especially oligomeric titanium(IV) tetrabutoxide, also referred to as polybutyl titanate;

where suitable alkoxide ligands are especially isobutoxy, n-butoxy, isopropoxy, ethoxy and 2-ethylhexoxy.

Especially suitable are the commercially available products Tyzor® AA, GBA, GBO, AA-75, AA-65, AA-105, DC, BEAT, BTP, TE, TnBT, KTM, TOT, TPT or IBAY (all from Dorf Ketal); Tytan PBT, TET, X85, TAA, ET, S2, S4 or S6 (all from Borica Company Ltd.) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Very particularly suitable organotitanates are selected from bis(ethylaceto-acetato)diisobutoxytitanium(IV) (commercially available, for example, as Tyzor® IBAY from Dorf Ketal), bis(ethylacetoacetato)diisopropoxytitanium (IV) (commercially available, for example, as Tyzor® DC from Dorf Ketal), bis(acetylacetonato)diisopropoxytitanium (IV), bis(acetylacetonato)diisobutoxy-titanium(IV), tris (oxyethyl)amine-isopropoxy-titanium(IV), bis[tris(oxyethyl)-amine]diisopropoxytitanium(IV), bis(2-ethylhexane-1,3-dioxy)titanium(IV), tris[2-((2-aminoethyl)amino) ethoxy]ethoxytitanium(IV), bis(neopentyl(diallyl)oxy)-diethoxytitanium(IV), titanium(IV) tetrabutoxide, tetra(2-ethylhexyloxy) titanate, tetra(isopropoxy) titanate and polybutyl titanate.

Most preferred are bis(ethylacetoacetato)diisobutoxytitanium(IV) or bis(ethylacetoacetato)diisopropoxytitanium (IV).

The composition may comprise further constituents, especially the following auxiliaries and additives:

adhesion promoters and/or crosslinkers, especially aminosilanes such as, in particular, 3-aminopropyltrimethoxysilane, 3-aminopropyldimethoxymethyl-silane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)-propyl] ethylenediamine or the analogs thereof with ethoxy in place of methoxy groups, and also N-phenyl-, N-cyclohexyl- or N-alkylaminosilanes, mercaptosilanes, epoxysilanes, (meth)acryloylsilanes, anhydridosilanes, carbamatosilanes, alkylsilanes or iminosilanes, oligomeric forms of these silanes, adducts formed from primary aminosilanes with epoxysilanes or (meth)acryloylsilanes or anhydridosilanes, amino-functional alkylsilsesquioxanes, especially amino-functional methylsilsesquioxane or amino-functional propylsilsesquioxane. Especially suitable are 3-amino-propyltrimethoxysilane, 3-aminopropyltriethoxysilane, N-(2-aminoethyl)-3-aminopropyltrimethoxysilane, N-(2-aminoethyl)-3-aminopropyltriethoxy-silane, 3-glycidoxypropyltrimethoxysilane, 3-glycidoxypropyltriethoxysilane or 3-ureidopropyltrimethoxysilane, or oligomeric forms of these silanes;

desiccants, especially tetraethoxysilane, vinyltrimethoxysilane, vinyltriethoxysilane or organoalkoxysilanes having a functional group in the α position to the silane group, especially N-(methyldimethoxysilylmethyl)-O-methylcarbamate, (methacryloyloxymethyl)silanes, methoxymethylsilanes, orthoformic esters, calcium oxide or molecular sieves, especially vinyltrimethoxysilane or vinyltriethoxysilane;

plasticizers, especially trialkylsilyl-terminated polydialkylsiloxanes, preferably trimethylsilyl-terminated polydimethylsiloxanes, especially having viscosities in the range from 10 to 1'000 mPa·s, or corresponding compounds in which some of the methyl groups have been replaced by other organic groups, especially phenyl, vinyl or trifluoropropyl groups, called reactive plasticizers, in the form of monofunctional polysiloxanes, i.e. those that are reactive at one end, carboxylic esters such as phthalates, especially dioctyl phthalate, bis(2-ethylhexyl) phthalate, bis(3-propylheptyl) phthalate, diisononyl phthalate or diisodecyl phthalate, diesters of ortho-cyclohexane-dicarboxylic acid, especially diisononyl 1,2-cyclohexanedicarboxylate, adipates, especially dioctyl adipate, bis(2-ethylhexyl) adipate, azelates, especially bis(2-ethylhexyl) azelate, sebacates, especially bis(2-ethylhexyl) sebacate or diisononyl sebacate, polyols, especially polyoxyalkylene polyols or polyester polyols, glycol ethers, glycol esters, organic phosphoric or sulfonic esters, sulfonamides, polybutenes, or fatty acid methyl or ethyl esters derived from natural fats or oils, also called "biodiesel", plasticizers containing siloxane groups being particularly suitable for polymers containing silane groups in the form of polyorganosiloxanes;

solvents;

inorganic or organic fillers, especially natural, ground or precipitated calcium carbonates, optionally coated with fatty acids, especially stearic acid, baryte (heavy spar), talcs, quartz flours, quartz sand, dolomites, wollastonites, kaolins, calcined kaolins, mica (potassium aluminum silicate), molecular sieves, aluminum oxides, aluminum hydroxides, magnesium hydroxide, silicas including finely divided silicas from pyrolysis processes, industrially produced carbon blacks, graphite, metal powders such as aluminum, copper, iron, silver or steel, PVC powder or hollow spheres;

fibers, especially glass fibers, carbon fibers, metal fibers, ceramic fibers or polymer fibers such as polyamide fibers or polyethylene fibers;

dyes;

pigments, especially titanium dioxide or iron oxides;

rheology modifiers, especially thickeners, especially sheet silicates such as bentonites, derivatives of castor oil, hydrogenated castor oil, polyamides, polyurethanes, urea compounds, fumed silicas, cellulose ethers or hydrophobically modified polyoxyethylenes;

stabilizers against oxidation, heat, light or UV radiation;

natural resins, fats or oils such as rosin, shellac, linseed oil, castor oil or soya oil;

non-reactive polymers such as, in particular, homo- or copolymers of unsaturated monomers, especially from the group comprising ethylene, propylene, butylene, isobutylene, isoprene, vinyl acetate or alkyl (meth) acrylates, especially polyethylenes (PE), polypropylenes (PP), polyisobutylenes, ethylene-vinyl acetate copolymers (EVA) or atactic poly-α-olefins (APAO);

flame-retardant substances, especially the already mentioned fillers aluminum hydroxide and magnesium hydroxide, or, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis (diphenyl phosphate) or ammonium polyphosphates;

surface-active substances, especially wetting agents, leveling agents, deaerating agents or defoamers;

biocides, especially algicides, fungicides or substances that inhibit fungal growth;

and other substances customarily used in curable compositions. It may be advisable to chemically or physically dry certain constituents before mixing them into the composition.

In a preferred embodiment, the composition comprises at least one desiccant and at least one adhesion promoter and/or crosslinker.

In a preferred embodiment, the composition does not comprise any phthalates as plasticizers. Such compositions are toxicologically advantageous and have fewer problems with migration effects.

The composition is preferably produced and stored with exclusion of moisture. Typically, it is storage-stable with exclusion of moisture in a suitable package or arrangement, such as, more particularly, a bottle, a canister, a pouch, a bucket, a vat or a cartridge.

The composition may take the form of a one-component or of a multi-component, especially two-component, composition.

In the present document, "one-component" refers to a composition in which all constituents of the composition are stored in a mixture in the same container and which is curable with moisture.

In the present document, "two-component" refers to a composition in which the constituents of the composition are present in two different components which are stored in separate containers. Only shortly before or during the application of the composition are the two components mixed with one another, whereupon the mixed composition cures, optionally under the action of moisture.

If the composition comprises a polyorganosiloxane having terminal silane groups, preference is given either to a one-component composition, also referred to as RTV-1, or to a two-component composition, also referred to as RTV-2. In the case of an RTV-2 composition, the polyorganosiloxane having terminal silane groups is preferably a constituent of the first component, and a silane crosslinker, especially a silane of the formula (V), is preferably a constituent of the second component. The catalyst of the formula (I) may be present in the first and/or the second component.

If the composition comprises an organic polymer containing silane groups, the composition is preferably a one-component composition. Any second or optionally further components is/are mixed with the first component prior to or on application, especially by means of a static mixer or by means of a dynamic mixer.

The composition is especially applied at ambient temperature, preferably within a temperature range between 0° C. and 45° C., especially 5° C. to 35° C., and also cures under these conditions.

On application, the crosslinking reaction of the silane groups commences, if appropriate under the influence of moisture. Silane groups present can condense with silanol groups present to give siloxane groups (Si—O—Si groups). Silane groups present can also be hydrolyzed on contact with moisture to give silanol groups (Si—OH groups) and form siloxane groups (Si—O—Si groups) through subsequent condensation reactions. As a result of these reactions, the composition ultimately cures. The catalyst of the formula (I) accelerates this curing.

If water is required for the curing, this can either come from the air (air humidity), or else the composition can be contacted with a water-containing component, for example by painting, for example with a smoothing agent, or by spraying, or water or a water-containing component can be added to the composition on application, for example in the form of a water-containing or water-releasing liquid or paste. A paste is especially suitable if the composition itself is in the form of a paste.

In the case of curing by means of air humidity, the composition cures from the outside inward, at first forming a skin on the surface of the composition. What is called the skin time is a measure of the curing rate of the composition. The speed of curing is generally determined by various factors, for example the availability of water, temperature, etc.

The composition is suitable for a multitude of uses, especially as a paint, varnish or primer, as a resin for production of fiber composites, as a rigid foam, flexible foam, molding, elastomer, fiber, film or membrane, as a potting compound, sealant, adhesive, covering, coating or paint for construction and industrial applications, for example as a seam seal, cavity seal, electrical insulation compound, spackling compound, joint sealant, weld or crimp seam sealant, assembly adhesive, bodywork adhesive, glazing adhesive, sandwich element adhesive, laminating adhesive, laminate adhesive, packaging adhesive, wood adhesive, parquet adhesive, anchoring adhesive, floor covering, floor coating, balcony coating, roof coating, concrete protection coating, parking garage coating, seal, pipe coating, anticorrosion coating, textile coating, damping element, sealing element or spackling compound. The composition is particularly suitable as an adhesive and/or sealant, especially for joint sealing and for elastic adhesive bonds in construction and industrial applications, and as elastic coating with crack-bridging properties, especially for protection and/or sealing of, for example, roofs, floors, balconies, parking decks or concrete pipes.

The composition is thus preferably an adhesive or a sealant or a coating.

A composition of this kind typically comprises plasticizers, fillers, adhesion promoters and/or crosslinkers and desiccants, and optionally further auxiliaries and additives.

For an application as adhesive or sealant, the composition preferably has a pasty consistency with structurally viscous properties. Such a pasty sealant or adhesive is especially applied to a substrate from standard cartridges which are operated manually, by means of compressed air or with a battery, or from a vat or hobbock by means of a delivery pump or an extruder, optionally by means of an application robot.

For an application as coating, the composition preferably has a liquid consistency at room temperature with self-leveling properties. It may be slightly thixotropic, such that the coating is applicable to sloping to vertical surfaces without flowing away immediately. It is especially applied by means of a roller or brush or by pouring-out and distribution by means, for example, of a roller, a scraper or a notched trowel.

On application, the composition is preferably applied to at least one substrate. Suitable substrates are especially
- glass, glass ceramic, concrete, mortar, brick, tile, gypsum and natural rocks such as limestone, granite or marble;
- metals and alloys such as aluminum, iron, steel and nonferrous metals, and also surface-finished metals and alloys such as galvanized or chromed metals;
- leather, textiles, paper, wood, woodbase materials bonded with resins, for example phenolic, melamine or epoxy resins, resin-textile composites and further polymer composites;
- plastics such as polyvinyl chloride (rigid and flexible PVC), acrylonitrile-butadiene-styrene copolymers (ABS), polycarbonate (PC), polyamide (PA), polyesters, poly(methyl methacrylate) (PMMA), epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), and also fiber-reinforced plastics such as carbon fiber-reinforced plastics (CFP), glass fiber-reinforced plastics (GFP) and sheet molding compounds (SMC), where the plastics may preferably have been surface-treated by means of plasma, corona or flames;
- coated substrates such as powder-coated metals or alloys;
- paints or varnishes, especially automotive topcoats.

If required, the substrates can be pretreated prior to the application of the composition, especially by chemical and/or physical cleaning methods or by the application of an adhesion promoter, an adhesion promoter solution or a primer.

The composition is particularly suitable for contact with substrates that are particularly sensitive to defects caused by migrating substances, especially by the formation of discoloration or specks. These are, in particular, fine-pore substrates such as marble, limestone or other natural stones, gypsum, cement mortar or concrete, but also plastics. Especially on PVC, severe discoloration is observed in the presence of catalysts, for example DBU or TMG, and cannot be removed by cleaning. No such effects are observed with the catalyst of the formula (I).

It is possible to bond or seal two identical or two different substrates, especially the aforementioned substrates.

After the curing of the composition with water, especially in the form of air humidity, and/or with at least one suitable crosslinker, a cured composition is obtained.

The use of the composition gives rise to an article which especially has been bonded, sealed or coated with the composition. The article is especially a built structure, especially a structure built by structural engineering or civil engineering, an industrially manufactured good or a consumable good, especially a window, a domestic appliance or a mode of transport such as, more particularly, an automobile, a bus, a truck, a rail vehicle, a ship, an aircraft or a helicopter; or the article may be an installable component thereof.

EXAMPLES

Adduced hereinafter are working examples which are intended to elucidate the invention described in detail. It will be appreciated that the invention is not restricted to these described working examples.

"Standard climatic conditions" refer to a temperature of 23±1° C. and a relative air humidity of 50±5%.

"EEW" stands for epoxy equivalent weight.

$^1$H NMR spectra were measured on a spectrometer of the Bruker Ascend 400 type at 400.14 MHz; the chemical shifts δ are reported in ppm relative to tetramethylsilane (TMS). Coupling constants J are reported in Hz. No distinction was made between true coupling and pseudo-coupling patterns.

Infrared spectra (FT-IR) were measured on a Nicolet iS5 FT-IR instrument from Thermo Scientific equipped with a horizontal ATR measurement unit with a diamond crystal. Liquid samples were applied undiluted as films; solid samples were dissolved in $CH_2Cl_2$. The absorption bands are reported in wavenumbers ($cm^{-1}$) (measurement window: 4000-650 $cm^{-1}$).

Gas chromatograms (GC) were measured within the temperature range of 60 to 320° C. with a heating rate of 15° C./min and a run time of 10 min at 320° C. The injector temperature was 250° C. A Zebron ZB-5 column was used (L=30 m, ID=0.25 mm, dj=0.5 µm) with a gas flow rate of 1.5 ml/min. Detection was effected by means of flame ionization (FID), with evaluation of the signals via the area percent method.

The skin time (ST) was determined by applying a few grams of the composition to cardboard in a layer thickness of about 2 mm and measuring, under standard climatic conditions, the time until, when the surface of the composition was gently tapped by means of an LDPE pipette, there were for the first time no residues remaining any longer on the pipette. The characteristics of the surface were tested by touch.

The mechanical properties of tensile strength, elongation at break and modulus of elasticity (at 0-5% and at 0-50% or 0-100% elongation) were measured in accordance with DIN EN 53504 at a pulling speed of 200 mm/min.

Reagents Used:
DCC N,N'-dicyclohexylcarbodiimide (Sigma-Aldrich)
DIC N,N'-diisopropylcarbodiimide (Sigma-Aldrich)
Functional Compounds Used:
TMPTA 1,1,1-trimethylolpropane triacrylate (Sartomer SR-351, from Sartomer)
Polymer-NCO-1 reaction product of 500 g of Acclaim® 4200 polyol (polyoxypropylenediol with a low level of unsaturation, from Bayer; OH number 28.0 mg KOH/g) and 2000 g of Caradol® MD34-02 polyol (polyoxypropylenepolyoxyethylenetriol, from Shell; OH number 35.0 mg KOH/g) with 253 g of tolylene diisocyanate (Desmodur® T80 P, from Bayer); NCO content: 2.06% by weight
Polymer-HEA-1 reaction product of 169.47 g of polymer NCO-1 with 9.60 g of 2-hydroxyethyl acrylate (HEA) and 0.2 g of bismuth neodecanoate at 80° C. for 3 h (until complete conversion of the isocyanate band at 2277 $cm^{-1}$ in the FT-IR spectrum)
Polymer-NCO-2 reaction product of 3.2 kg of Acclaim® 12200 polyol (polyoxypropylenediol with a low level of unsaturation, from Bayer; OH number 11.0 mg KOH/g) with 149.4 g of isophorone diisocyanate (Vestanat® IPDI, from Evonik) and 0.5 g of bismuth tris(neodecanoate); NCO content: 0.88% by weight EHGE 2-ethylhexyl glycidyl ether (D.E.R.™ 728, from Dow, EEW about 210 g/eq)

DY-E monoglycidyl ether of $C_{12}$-$C_{14}$ alcohols (Araldite® DY-E, from Huntsman, EEW about 282 g/eq)

DY-K o-cresyl glycidyl ether (Araldite® DY-E, from Huntsman, EEW about 282 g/eq)

BADGE bisphenol A diglycidyl ether (Araldite® MY 790, from Huntsman, EEW about 186 g/eq)

DY-F polypropylene glycol diglycidyl ether (Araldite® DY-F, from Huntsman, EEW about 510 g/eq)

2,2-dimethyl-3-lauroyloxypropanal (prepared as in U.S. Pat. No. 7,625,993, aldehyde A1)

2,2-dimethyl-3-(N-morpholino)propanal (prepared as in U.S. Pat. No. 8,252,859)

1,2-propylene carbonate (Sigma-Aldrich)

pentane-2,4-dione (Sigma-Aldrich)

N,N-diethylacetoacetamide (Sigma-Aldrich)

Preparation of Guanidines of the Formula (II)

Compound G-1:
1-(3-aminopropyl)-2,3-dicyclohexylguanidine

In a round-bottom flask, 2.50 g of 1,3-diaminopropane and 6.89 g of DCC were mixed and heated to 120° C. while stirring. After 1 hour, the carbodiimide band at about 2120 $cm^{-1}$ (FT-IR spectroscopy) had completely disappeared. Thereafter, the reaction mixture was freed of the volatile constituents under reduced pressure. This gave 9.36 g of a pale yellow oil of low odor, which solidified after a few days to give a solid mass.

$^1$H-NMR (CDCl$_3$): δ 1.05-1.2 and 1.25-1.40 (2×m, 10H), 1.54-1.78 (m, 10H), 1.88-2.0 (m, 4H), 2.73 (m, 2H), 3.12 (m, 2H), 3.22 (br s, 2H).

FT-IR: 3371 (N—H), 2921, 2849, 1627 (C=N), 1502, 1447, 1324, 1238, 1147, 1111, 888, 713.

Compound G-2: 1-(2-aminopropyl)-2,3-dicyclohexylguanidine and 1-(3-aminoprop-2-yl)-2,3-dicyclohexylguanidine In a round-bottom flask, 7.78 g of 1,2-diaminopropane and 20.63 g of DCC were mixed and heated to 120° C. while stirring. After 3 hours, the carbodiimide band at about 2120 $cm^{-1}$ (FT-IR spectroscopy) had completely disappeared. Thereafter, the reaction mixture was freed of the volatile constituents under reduced pressure. This gave 28.0 g of a pale yellow oil of low odor.

FT-IR: 3270 (N—H), 2922, 2849, 1626 (C=N), 1497, 1447, 1363, 1336, 1285, 1237, 1189, 1146, 1112, 1091, 1073, 1050, 1027, 977, 888, 860, 804, 715.

Compound G-3: 1-(6-amino-3,3(5),5-trimethyl-hexyl)-2,3-dicyclohexylguanidine and 1-(6-amino-2,2(4),4-trimethylhexyl)-2,3-dicyclohexylguanidine In a round-bottom flask, 16.62 g of Vestamin® TMD (mixture of 2,2,4- and 2,4,4-trimethylhexamethylene-1,6-diamine, from Evonik) and 20.63 g of DCC were mixed and heated to 120° C. while stirring. After 3 hours, the carbodiimide band at about 2120 $cm^{-1}$ (FT-IR spectroscopy) had completely disappeared. Thereafter, the reaction mixture was freed of the volatile constituents under reduced pressure. This gave 36.5 g of a pale yellow oil of low odor.

FT-IR: 3281 (N—H), 2923, 2850, 1635 (C=N), 1496, 1463, 1448, 1362, 1325, 1284, 1237, 1188, 1146, 1112, 1090, 1071, 1051, 1027, 977, 888, 860, 845, 804, 785, 714.

Compound G-4: 1-(3-cyclohexylaminopropyl)-2,3-diisopropylguanidine

In a round-bottom flask, 34.38 g of 3-(cyclohexylamino)propylamine (from BASF) and 25.24 g of DIC were mixed and heated to 120° C. while stirring. After 2 hours, the carbodiimide band at about 2120 $cm^{-1}$ (FT-IR spectroscopy) had completely disappeared. Thereafter, the reaction mixture was freed of the volatile constituents under reduced pressure. This gave 56.50 g of a pale yellow oil of low odor.

FT-IR: 3292 (N—H), 2960, 2924, 2852, 1633 (C=N), 1505, 1448, 1361, 1329, 1176, 1125, 889, 714.

Compound G-5: 1-(2-(2-hydroxyethoxy)ethyl)-2,3-dicyclohexylguanidine

In a round-bottom flask, 3.55 g of 2-(2-aminoethoxy)ethanol (Diglycolamine® Agent, from Huntsman) and 6.81 g of DCC were mixed and heated to 120° C. while stirring. After 24 hours, the carbodiimide band at about 2120 $cm^{-1}$ (FT-IR spectroscopy) had completely disappeared. This gave a pale yellow oil of low odor.

$^1$H-NMR (CDCl$_3$): δ 1.05-1.3 and 1.3-1.45 (2×m, 10H, CH$_2$), 1.54-1.78 (m, 8H), 1.88-2.0 (m, 4H), 3.13 (t, 2H, CH$_2$N), 3.69 (m, 4H, CH$_2$O), 3.81 (t, 2H, OCH$_2$CH$_2$N).

FT-IR: 3355 (O—H), 2922, 2849, 1617 (C=N), 1520, 1447, 1340, 1257, 1240, 1117, 1066, 888, 717.

Compound G-6: 1-(2-(2-hydroxyethoxy)ethyl)-2,3-diisopropylguanidine

In a round-bottom flask, 23.14 g of 2-(2-aminoethoxy)ethanol (Diglycolamine® Agent, from Huntsman) and 25.24 g of DIC were mixed and heated to 120° C. while stirring. After 24 hours, the carbodiimide band at about 2120 $cm^{-1}$ (FT-IR spectroscopy) had completely disappeared. Thereafter, the reaction mixture was freed of the volatile constituents under reduced pressure. This gave 56.50 g of a mobile, pale yellow oil of low odor.

FT-IR: 3354 (O—H), 2963, 2921, 2865, 1616 (C=N), 1524, 1465, 1362, 1337, 1178, 1121, 1066, 884, 829, 715.

Preparation of Amine Intermediates

Compound A-1: N-(2,2-dimethyl-3-lauroyloxypropylidene)-1,3-diaminopropane

In a round-bottom flask, 3.82 g of 1,3-diaminopropane and 14.21 g of 2,2-dimethyl-3-lauroyloxypropanal were mixed and heated to 60° C. while stirring. After 30 minutes, the volatile constituents were removed by means of reduced pressure at 80° C. This gave 16.96 g of a yellowish oil.

FT-IR: 3308, 2922, 2853, 1733, 1668, 1556, 1466, 1432, 1394, 1376, 1350, 1316, 1235, 1165, 1134, 1108, 1048, 1031, 1005, 946, 902, 877, 854, 798, 767, 722.

Compound A-2: N-(2,2-dimethyl-3-lauroyloxypropylidene)-1,2-diaminopropane

In a round-bottom flask, 3.81 g of 1,2-diaminopropane and 14.25 g of 2,2-dimethyl-3-lauroyloxypropanal were mixed and heated to 60° C. while stirring. After 20 minutes, the volatile constituents were removed by means of reduced pressure at 80° C. This gave 16.97 g of a colorless oil.

FT-IR: 3353, 2956, 2923, 2853, 1733, 1667, 1632, 1466, 1418, 1391, 1376, 1301, 1253, 1161, 1112, 1076, 1056, 1001, 934, 883, 826, 722.

Compound A-3: N-(2,2-dimethyl-3-(N-morpholino) propylidene)-1,3-diaminopropane

In a round-bottom flask, 3.16 g of 1,3-diaminopropane and 6.87 g of 2,2-dimethyl-3-(N-morpholino)propanal were mixed and heated to 80° C. while stirring. After 40 minutes, the volatile constituents were removed by means of reduced pressure at 80° C. This gave 8.67 g of a yellowish oil.

FT-IR: 3286, 2934, 2848, 2800, 1665, 1573, 1455, 1430, 1375, 1349, 1313, 1282, 1263, 1203, 1133, 1115, 1070, 1337, 1010, 983, 923, 863, 803, 767.

Preparation of Catalysts of the Formula (I)

Catalyst K-1: 1,1,1-trimethylolpropane tris(3-(3-(2, 3-dicyclohexylguanidino)propylamino)propionate)

In a round-bottom flask, 28.05 g of the previously prepared compound G-1 were mixed with 9.88 g of TMPTA and heated to 120° C. After 4 hours, the acrylate band at about 809 cm$^{-1}$ (FT-IR spectroscopy) had completely disappeared. Thereafter, the reaction mixture was freed of the volatile constituents under reduced pressure. This gave 37.93 g of a highly viscous, odorless oil.

FT-IR: 3291 (N—H), 2923, 2850, 1732 (C=O), 1628 (C=N), 1515, 1448, 1381, 1362, 1343, 1254, 1170, 1113, 1051, 1025, 888, 843, 782, 707.

Catalyst K-2: 1,1,1-trimethylolpropane tris(3-(N-cyclohexyl-3-(2,3-diisopropylguanidino)propylamino)propionate)

In a round-bottom flask, 28.25 g of the previously prepared compound G-4 were mixed with 9.88 g of TMPTA and heated to 120° C. After 24 hours, the acrylate band at about 809 cm$^{-1}$ (FT-IR spectroscopy) had completely disappeared. Thereafter, the reaction mixture was freed of the volatile constituents under reduced pressure. This gave 38.10 g of a highly viscous, odorless oil.

FT-IR: 2961, 2925, 2852, 1735 (C=O), 1627 (C=N), 1449, 1362, 1346, 1305, 1250, 1163, 1125, 1055, 889, 718.

Catalyst K-3

To an initial charge of 179.27 g of polymer HEA-1 in a round-bottom flask were added 23.45 g of the previously prepared compound G-4, and the reaction mixture was heated to 100° C. After 3 hours, the acrylate band at about 815 cm$^{-1}$ (FT-IR spectroscopy) had completely disappeared. This gave an odorless oil of moderate viscosity.

FT-IR: 2969, 2929, 2866, 1720 (C=O), 1644 (C=N), 1525, 1452, 1372, 1343, 1296, 1096, 1013, 925, 866, 832, 700.

Catalyst K-4

To an initial charge of 179.27 g of polymer HEA-1 in a round-bottom flask were added 23.19 g of the previously prepared compound G-2, and the reaction mixture was heated to 100° C. After 2 hours, the acrylate band at about 815 cm$^{-1}$ (FT-IR spectroscopy) had completely disappeared. This gave an odorless oil of moderate viscosity.

FT-IR: 3305, 1969, 2928, 2864, 1730 (C=O), 1682, 1621 (C=N), 1533, 1450, 1372, 1344, 1296, 1226, 1096, 1013, 926, 866, 825, 768, 718.

Catalyst K-5

To an initial charge of 179.27 g of polymer HEA-1 in a round-bottom flask were added 30.15 g of the previously prepared compound G-3, and the reaction mixture was heated to 100° C. After 2 hours, the acrylate band at about 815 cm$^{-1}$ (FT-IR spectroscopy) had completely disappeared. This gave an odorless oil of moderate viscosity.

FT-IR: 3312, 2969, 2928, 2865, 1728 (C=O), 1682, 1629 (C=N), 1538, 1450, 1372, 1344, 1296, 1226, 1097, 1013, 926, 865, 825, 767, 714.

Catalyst K-6

To an initial charge of 179.27 g of polymer HEA-1 in a round-bottom flask were added 24.40 g of the previously prepared compound G-1, and the reaction mixture was heated to 100° C. After 2 hours, the acrylate band at about 815 cm$^{-1}$ (FT-IR spectroscopy) had completely disappeared. This gave an odorless oil of moderate viscosity.

FT-IR: 3309, 2970, 2930, 2867, 1730 (C=O), 1620 (C=N), 1601, 1533, 1452, 1408, 1372, 1344, 1296, 1225, 1180, 1093, 1013, 926, 867, 811, 768.

Catalyst K-7

An initial charge of 282.2 g of polymer NCO-2 in a round-bottom flask was mixed with 17.79 g of the previously prepared compound G-5 under reduced pressure and heated to 50° C. After 1 hour, the isocyanate band at about 2263 cm$^{-1}$ (FT-IR spectroscopy) had completely disappeared. Then 1.5 g of vinyltrimethoxysilane were added. This gave an odorless oil of moderate viscosity.

FT-IR: 2969, 2929, 2866, 1720 (C=O), 1644 (C=N), 1525, 1452, 1372, 1343, 1296, 1096, 1013, 925, 866, 832, 700.

Catalyst K-8

An initial charge of 282.2 g of polymer NCO-2 in a round-bottom flask was mixed with 13.21 g of the previously prepared compound G-6 under reduced pressure and heated to 50° C. After 5 minutes, the isocyanate band at about 2263 cm$^{-1}$ (FT-IR spectroscopy) had completely disappeared. Then 1.5 g of vinyltrimethoxysilane were added. This gave an odorless oil of moderate viscosity.

FT-IR: 2969, 2930, 2867, 1720 (C=O), 1675, 1644 (C=N), 1525, 1454, 1372, 1343, 1296, 1096, 1013, 925, 867, 831.

Catalyst K-9: 1-(3-((3-((2-ethylhexyl)oxy)-2-hydroxypropyl)amino)propyl)-2,3-dicyclohexylguanidine In a round-bottom flask, 2.89 g of the previously prepared compound G-1 were mixed with 1.86 g of EHGE and heated to 50° C. After 24 hours, the epoxide band at about 911 cm$^{-1}$ (FT-IR spectroscopy) had almost completely disappeared, and then the reaction mixture was stirred at 80° C. for 3 hours. This gave a colorless, odorless oil of moderate viscosity, which solidified to give a wax after a few hours at room temperature.

FT-IR: 2923, 2851, 1627 (C=N), 1507, 1448, 1360, 1340, 1256, 1238, 1104, 977, 888, 845, 767, 725.

Catalyst K-10: 1-(3-((3-(((C$_{12-14}$-alkyl)oxy)-2-hydroxypropyl)amino)propyl)-2,3-dicyclohexylguanidine In a round-bottom flask, 2.89 g of the previously prepared compound G-1 were mixed with 2.82 g of DY-E and heated to 80° C. After 6 hours, the epoxide band at about 912 cm$^{-1}$ (FT-IR spectroscopy) had completely disappeared. This gave a colorless, odorless oil of moderate viscosity.

FT-IR: 3246, 2921, 2851, 1627 (C=N), 1505, 1463, 1449, 1405, 1361, 1344, 1304, 1257, 1239, 1112, 1028, 977, 889, 844, 814, 720.

Catalyst K-11: 1-(3-((3-((2-methylphenyl)oxy)-2-hydroxypropyl)amino)propyl)-2,3-dicyclohexylguanidine In a round-bottom flask, 2.89 g of the previously prepared compound G-1 were mixed with 1.83 g of DY-K and heated to 80° C. After 6 hours, the epoxide band at about 915 cm$^{-1}$ (FT-IR spectroscopy) had completely disappeared. This gave a colorless, odorless oil of moderate viscosity.

FT-IR: 3270, 2923, 2849, 1622 (C=N), 1602, 1494, 1448, 1360, 1339, 1307, 1287, 1243, 1190, 1147, 1120, 1050, 1034, 977, 924, 888, 940, 747, 712.

Catalyst K-12: 2,2-bis(4-(2-hydroxy-3-(3-(2,3-dicyclohexylguanidino)propyl)aminopropoxy)phenyl)propane In a round-bottom flask, 2.89 g of the previously prepared compound G-1 were mixed with 1.86 g of BADGE and heated to 80° C. After 6 hours, the epoxide band at about 914 cm$^{-1}$ (FT-IR spectroscopy) had completely disappeared. This gave a colorless, odorless oil of high viscosity.

FT-IR: 3357 (O—H), 2924, 2851, 1606 (C=N), 1580, 1507, 1450, 1383, 1343, 1296, 1235, 1181, 1105, 1084, 1033, 967, 915, 826, 757, 737, 726, 668.

Catalyst K-13: α,ω-bis(2-hydroxy-3-(3-(2,3-dicyclohexylguanidino)propyl)aminopropyl)polypropylene glycol In a round-bottom flask, 2.89 g of the previously prepared compound G-1 were mixed with 5.10 g of DY-F and heated to 80° C. After 6 hours, the epoxide band at about 907 cm$^{-1}$ (FT-IR spectroscopy) had completely disappeared. This gave a colorless, odorless oil of moderate viscosity, which took on a pasty consistency after a few hours at room temperature.

FT-IR: 3270, 2969, 2926, 2852, 1623 (C=N), 1507, 1449, 1372, 1343, 1298, 1257, 1099, 1014, 926, 889, 862, 836, 712.

Catalyst K-14: 2-hydroxypropyl N-(3-(2,3-dicyclohexylguanidino)propyl)carbamate and 3-hydroxy-2-propyl N-(3-(2,3-dicyclohexylguanidino)propyl)carbamate In a round-bottom flask, 2.89 g of the previously prepared compound G-1 were mixed with 1.12 g of 1,2-propylene carbonate and heated to 90° C. After 30 minutes, the volatile constituents were removed by means of reduced pressure at 80° C. This gave 4.03 g of a transparent, odorless solid.

FT-IR: 3335, 2925, 2851, 1699, 1621, 1518, 1448, 1361, 1338, 1257, 1145, 1109, 1054, 992, 978, 889, 845, 800, 775, 715.

Catalyst K-15: 1-(3-(3-acetylprop-2-en-2-yl)aminopropyl)-2,3-dicyclohexylguanidine In a round-bottom flask, 2.89 g of the previously prepared compound G-1 were mixed with 1.10 g of pentane-2,4-dione and, after 10 minutes, the volatile constituents were removed by means of reduced pressure at 80° C. This gave 3.98 g of a yellow, odorless solid.

FT-IR: 3192, 3044, 2925, 2852, 1608, 1570, 1483, 1445, 1360, 1295, 1245, 1237, 1211, 1191, 1173, 1150, 1103, 1074, 1052, 1000, 952, 890, 846, 785, 738.

Catalyst K-16: 1-(3-(3-(N,N-diethylaminocarbonyl)prop-2-en-2-yl)aminopropyl)-2,3-dicyclohexylguanidine In a round-bottom flask, 2.89 g of the previously prepared compound G-1 were mixed with 1.61 g of N,N-diethylacetoacetamide and, after 10 minutes, the volatile constituents were removed by means of reduced pressure. This gave 3.89 g of a white, odorless solid.

FT-IR: 3197, 2970, 2926, 2852, 1722, 1633, 1591, 1473, 1493, 1476, 1448, 1360, 1347, 1315, 1257, 1231, 1150, 1122, 1069, 999, 980, 954, 913, 890, 843, 827, 772, 710.

Catalyst K-17: 3-((3-(2,3-dicyclohexylguanidino)propyl)imino)-2,2-dimethylpropyl dodecanoate In a round-bottom flask, 2.89 g of the previously prepared compound G-1 were mixed with 2.97 g of 2,2-dimethyl-3-lauroyloxypropanal, the mixture was stirred at room temperature for 10 minutes and then the volatile constituents were removed by means of reduced pressure at 80° C. This gave 5.72 g of a yellowish, odorless oil of moderate viscosity.

FT-IR: 3202, 2923, 2852, 1739, 1661, 1627, 1564, 1450, 1417, 1392, 1364, 1348, 1288, 1246, 1190, 1151, 1107, 1067, 1028, 999, 890, 845, 800, 720.

Catalyst K-18: 3-((3-(2,3-dicyclohexylguanidino)propyl)imino)-2,2-dimethylpropyl dodecanoate In a round-bottom flask, 7.06 g of the previously prepared compound A-1 were mixed with 4.05 g of DCC and heated to 110° C. while stirring. After 48 hours, the carbodiimide band at about 2120 cm$^{-1}$ (FT-IR spectroscopy) had completely disappeared. Thereafter, the reaction mixture was freed of the volatile constituents under reduced pressure. This gave 11.12 g of a yellow, odorless oil of low viscosity.

FT-IR: 3292, 2922, 2851, 1738, 1640, 1543, 1449, 1364, 1315, 1253, 1151, 1110, 1070, 889, 845, 721.

Catalyst K-19: 3-((3-(2,3-diisopropylguanidino)propyl)imino)-2,2-dimethylpropyl dodecanoate In a round-bottom flask, 5.79 g of the previously prepared compound A-1 were mixed with 1.96 g of DIC and heated to 110° C. while stirring. After 4 days, the carbodiimide band at about 2120 cm$^{-1}$ (FT-IR spectroscopy) had completely disappeared. Thereafter, the reaction mixture was freed of the volatile constituents under reduced pressure. This gave 7.75 g of a yellow, odorless oil of low viscosity.

FT-IR: 3290, 2958, 2923, 2853, 1738, 1640, 1538, 1465, 1364, 1258, 1166, 1124, 1012, 933, 721.

Catalyst K-20: 3-((3-(2,3-dicyclohexylguanidino)prop-2-yl)imino)-2,2-dimethylpropyl dodecanoate In a round-bottom flask, 7.65 g of the previously prepared compound A-2 were mixed with 4.41 g of DCC and heated to 110° C. while stirring. After 7 days, the carbodiimide band at about 2120 cm$^{-1}$ (FT-IR spectroscopy) had completely disappeared. Thereafter, the reaction mixture was freed of the volatile constituents under reduced pressure. This gave 12.06 g of an orange, odorless oil of low viscosity.

FT-IR: 3304, 2923, 2852, 1738, 1643, 1538, 1463, 1449, 1374, 1345, 1318, 1252, 1237, 1151, 1111, 1072, 1027, 978, 940, 889, 861, 845, 721.

Catalyst K-21: 1-(3-((3-(N-morpholino)-2,2-dimethylpropylidene)amino)propyl)-2,3-dicyclohexylguanidine In a round-bottom flask, 7.56 g of the previously prepared compound A-3 were mixed with 4.11 g of DCC and heated to 90° C. while stirring. After 7 days, the carbodiimide band at about 2120 cm$^{-1}$ (FT-IR spectroscopy) had completely disappeared. Thereafter, the reaction mixture was freed of the volatile constituents under reduced pressure. This gave 8.63 g of a yellow, odorless oil of low viscosity.

FT-IR: 3355, 2923, 2849, 2807, 1636, 1504, 1449, 1360, 1345, 1282, 1268, 1257, 1236, 1136, 1116, 1070, 1051, 1012, 978, 929, 888, 864, 802, 713.

Preparation of Polyethers Containing Silane Groups

Polymer STP-1:

With exclusion of moisture, 1000 g of Acclaim® 12200 polyol (polyoxy-propylenediol having a low level of unsaturation, from Bayer; OH number 11.0 mg KOH/g), 43.6 g of isophorone diisocyanate (IPDI; Vestanat® IPDI, from Evonik), 126.4 g of diisodecyl phthalate (DIDP) and 0.1 g of bismuth tris(neodecanoate) (10% by weight in DIDP) were heated up to 90° C. while stirring constantly and left at this temperature until the content of free isocyanate groups determined by titrimetry had reached a stable value of 0.63% by weight. Subsequently, 63.0 g of diethyl N-(3-trimethoxysilylpropyl)-aminosuccinate (adduct formed from 3-aminopropyltrimethoxysilane and diethyl maleate; prepared according to the details in U.S. Pat. No. 5,364,955) were mixed in and the mixture was stirred at 90° C. until it was no longer possible to detect any free isocyanate by means of FT-IR spectroscopy. The polyether containing trimethoxysilane groups thus obtained, having a silane equivalent weight of about 6880 g/eq (calculated from the amounts used), was cooled down to room temperature and stored with exclusion of moisture.

Polymer STP-2:

With exclusion of moisture, 1000 g of Acclaim® 12200 polyol (polyoxy-propylenediol having a low level of unsaturation, from Bayer; OH number 11.0 mg KOH/g), 43.6 g of isophorone diisocyanate (IPDI; Vestanat® IPDI, from Evonik), 126.4 g of diisodecyl phthalate (DIDP) and 0.1 g of bismuth tris(neodecanoate) (10% by weight in DIDP) were heated up to 90° C. while stirring constantly and left at this temperature until the content of free isocyanate groups determined by titrimetry had reached a stable value of 0.64% by weight. Subsequently, 70.6 g of diethyl N-(3-triethoxysilylpropyl)-aminosuccinate (adduct formed from 3-aminopropyltriethoxysilane and diethyl maleate) were mixed in and the mixture was stirred at 90° C. until it was no longer possible to detect any free isocyanate by means of FT-IR spectroscopy. The polyether containing triethoxysilane groups thus obtained, having a silane equivalent weight of about 6920 g/eq (calculated from the amounts used), was cooled down to room temperature and stored with exclusion of moisture.

Commercial Catalysts Used:
DBU  1,8-diazabicyclo[5.4.0]undec-7-ene (Lupragen® N 700, from BASF) TMG 1,1,3,3-tetramethylguanidine (from Sigma-Aldrich)
IBAY  bis(ethylacetoacetato)diisobutoxytitanium(IV) (Tyzor® IBAY, from Dorf Ketal)

Compositions Based on Polymers Containing Silane Groups:

Comparative examples in tables 1 to 8 are indicated by "(Ref)".

Compositions Z1 to Z26:

A composition composed of 96.5 g of polymer STP-1, 0.5 g of vinyltrimethoxy-silane and 3.0 g of 3-aminopropyltrimethoxysilane was blended with various catalysts in the amount specified according to table 1, and the mixture was tested for viscosity and skin time (ST) under standard climatic conditions, before and after storage. The skin time serves as a measure of the activity of the catalyst in relation to the crosslinking reaction of the silane groups, i.e. of the crosslinking rate; the change in viscosity and the skin time after storage are a measure of storage stability. In addition, the mixture applied, after 24 hours under standard climatic conditions, was tested as to whether the surface was dry as desired or whether a greasy film had formed, which is a sign of the exudation of the catalyst owing to poor compatibility with the cured polymer, and/or whether the surface was tacky, which is a sign of incomplete curing. In addition, the mixture was used to produce a film of thickness 2 mm, which was left to cure under standard climatic conditions for 7 days and tested for mechanical properties. The results are shown in tables 1 and 2. "Comp." stands for "composition".

TABLE 1

| Comp. | Catalyst | Amount | Concentration[1] | Viscosity [Pa · s] fresh | stored[2] | increase | ST fresh | stored[2] |
|---|---|---|---|---|---|---|---|---|
| Z1 | K-1[3] | 0.70 g | 1.90 | 28.1 | 36.3 | 29% | 16' | 23' |
| Z2 | K-2[3] | 0.70 g | 1.90 | 30.2 | 41.8 | 38% | 12' | 18' |
| Z3 | K-3 | 4.66 g | 2.00 | 26.4 | 29.5 | 12% | 38' | 30' |
| Z4 | K-4 | 4.73 g | 2.00 | 34.6 | 47.2 | 36% | 26' | 21' |
| Z5 | K-5 | 4.89 g | 2.00 | 32.6 | 37.6 | 15% | 20' | 29' |
| Z6 | K-6 | 4.52 g | 2.00 | 29.0 | 31.0 | 7% | 30' | 21' |
| Z7 | K-7 | 12.80 g | 1.90 | 32.5 | 50.8 | 56% | 32' | 11' |
| Z8 | K-8 | 12.65 g | 1.90 | 26.5 | 49.3 | 86% | 51' | 11' |

TABLE 1-continued

| Comp. | Catalyst | Amount | Concentration[1] | Viscosity [Pa·s] fresh | stored[2] | increase | ST fresh | stored[2] |
|---|---|---|---|---|---|---|---|---|
| Z9 | K-9[3] | 0.85 g | 1.90 | 21.4 | 26.2 | 22% | 12' | 21' |
| Z10 | K-9[3] | 0.11 g | 0.25 | 25.2 | 32.9 | 31% | 44' | 80' |
|  | IBAY | 0.25 g | 0.50 |  |  |  |  |  |
| Z11 | K-10 | 1.02 g | 1.90 | 22.0 | 32.8 | 49% | 10' | 25' |
| Z12 | K-11[3] | 0.84 g | 1.90 | 19.4 | 25.5 | 31% | 33' | 31' |
| Z13 | K-12[3] | 0.85 g | 1.90 | 20.8 | 26.2 | 26% | 9' | 22' |
| Z14 | K-13[3] | 1.42 g | 1.90 | 20.1 | 30.5 | 52% | 14' | 21' |
| Z15 | K-13[3] | 0.19 g | 0.25 | 27.3 | 36.3 | 33% | 75' | 80' |
|  | IBAY | 0.25 g | 0.50 |  |  |  |  |  |
| Z16 | K-14[3] | 0.70 g | 1.90 | 21.0 | 32.0 | 52% | 10' | 11' |
| Z17 | K-15[3] | 0.67 g | 1.90 | 25.0 | 44.6 | 78% | 14' | 9' |
| Z18 | K-16[3] | 0.77 g | 1.90 | 27.8 | 59.6 | 114% | 7' | 7' |
| Z19 | K-17[3] | 1.00 g | 1.90 | 26.4 | 43.8 | 66% | 20' | 13' |
| Z20 | K-18[3] | 1.00 g | 1.90 | 34.5 | 48.6 | 41% | 21' | 18' |
| Z21 | K-19 | 1.86 g | 1.90 | 36.2 | 52.2 | 44% | 23' | 18' |
| Z22 | K-20 | 1.00 g | 1.90 | 35.4 | 51.8 | 46% | 25' | 19' |
| Z23 | K-21 | 0.80 g | 1.90 | 43.3 | 77.3 | 79% | 14' | 7' |
| Z24 (Ref) | DBU | 0.28 g | 1.90 | 27.2 | 36.9 | 36% | 25' | 29' |
| Z25 (Ref) | TMG | 0.21 g | 1.90 | 22.3 | 24.6 | 10% | 65' | 75' |
| Z26 (Ref) | DBU | 0.04 g | 0.25 | 26.9 | 28.9 | 7% | 54' | 90' |
|  | IBAY | 0.25 g | 0.50 |  |  |  |  |  |

[1]mmol of amidine or guanidine groups/metal atoms per 100 g of polyether containing silane groups.
[2]for 7 days at 60° C. in a closed container.
[3]as a solution (40% by wt.) in N-ethylpyrrolidone.

TABLE 2

| Comp. | Surface after 24 h | Tensile strength | Elongation at break | Modulus of elasticity 0-5% | 0-50% |
|---|---|---|---|---|---|
| Z1 | dry | 0.74 MPa | 123% | 1.00 MPa | 0.72 MPa |
| Z2 | dry | 0.67 MPa | 104% | 1.02 MPa | 0.71 MPa |
| Z3 | dry | 0.82 MPa | 133% | 0.82 MPa | 0.74 MPa |
| Z4 | dry | 0.76 MPa | 124% | 1.26 MPa | 0.74 MPa |
| Z5 | dry | 0.81 MPa | 139% | 1.21 MPa | 0.72 MPa |
| Z6 | dry | 0.79 MPa | 126% | 1.07 MPa | 0.74 MPa |
| Z7 | dry | 0.73 MPa | 136% | 0.94 MPa | 0.66 MPa |
| Z8 | dry | 0.70 MPa | 115% | 1.00 MPa | 0.70 MPa |
| Z9 | dry | 0.72 MPa | 97% | 1.14 MPa | 0.79 MPa |
| Z10 | dry | 0.66 MPa | 88% | 0.90 MPa | 0.77 MPa |
| Z11 | dry | 0.73 MPa | 106% | 1.02 MPa | 0.77 MPa |
| Z12 | dry | 0.69 MPa | 95% | 0.98 MPa | 0.77 MPa |
| Z13 | dry | 0.96 MPa | 140% | 1.10 MPa | 0.84 MPa |
| Z14 | dry | 0.68 MPa | 95% | 1.00 MPa | 0.78 MPa |
| Z15 | dry | 0.75 MPa | 116% | 0.90 MPa | 0.75 MPa |
| Z16 | dry | 0.59 MPa | 71% | 0.94 MPa | 0.78 MPa |
| Z17 | dry | 0.68 MPa | 91% | 1.00 MPa | 0.78 MPa |
| Z18 | dry | 0.60 MPa | 77% | 0.98 MPa | 0.77 MPa |
| Z19 | dry | 0.61 MPa | 79% | 0.94 MPa | 0.77 MPa |
| Z20 | almost dry | 0.63 MPa | 82% | 1.08 MPa | 0.80 MPa |
| Z21 | almost dry | 0.62 MPa | 81% | 1.14 MPa | 0.81 MPa |
| Z22 | dry | 0.66 MPa | 89% | 1.10 MPa | 0.80 MPa |
| Z23 | dry | 0.57 MPa | 65% | 1.25 MPa | 0.81 MPa |
| Z24(Ref) | greasy | 0.58 MPa | 72% | 1.16 MPa | 0.77 MPa |
| Z25(Ref) | tacky | 0.62 MPa | 90% | 1.19 MPa | 0.75 MPa |
| Z26(Ref) | dry | 0.66 MPa | 91% | 0.93 MPa | 0.74 MPa |

Compositions Z27 to Z37:

A composition composed of 95.9 g of polymer STP-2, 0.4 g of vinyltriethoxy-silane and 3.7 g of N-(2-aminoethyl)-3-aminopropyltriethoxysilane was blended with various catalysts in the amount specified according to table 3, and the mixture was tested as described for composition Z1 for viscosity, skin time (ST), surface characteristics and mechanical properties. The results are shown in tables 3 and 4. "Comp." stands for "composition".

TABLE 3

| Comp. | Catalyst | Amount | Concentration[1] | Viscosity [Pa·s] fresh | stored[2] | increase | ST fresh | stored[2] |
|---|---|---|---|---|---|---|---|---|
| Z27 | K-3 | 9.72 g | 4.2 | 36.4 | 66.4 | 82% | 4 h 20' | 1 h 23' |
| Z28 | K-4 | 9.86 g | 4.2 | 40.8 | 48.9 | 20% | 4 h 29' | 2 h 24' |
| Z29 | K-5 | 10.20 g | 4.2 | 41.5 | 47.8 | 15% | 4 h 11' | 2 h 53' |
| Z30 | K-6 | 9.43 g | 4.2 | 39.2 | 42.0 | 7% | 4 h | 3 h 36' |
| Z31 | K-9 | 1.68 g | 3.8 | 79.6 | 101.9 | 28% | 1 h 16' | 1 h 25' |
| Z32 | K-10 | 2.02 g | 3.8 | 76.3 | 96.6 | 27% | 1 h 49' | 1 h 51' |
| Z33 | K-11[3] | 1.67 g | 3.8 | 58.4 | 83.0 | 42% | 1 h 33' | 1 h 21' |
| Z34 | K-12[3] | 1.68 g | 3.8 | 58.2 | 97.5 | 68% | 38' | 33' |
| Z35 | K-13 | 2.83 g | 3.8 | 36.6 | 61.0 | 67% | 1 h 07' | 1 h 15' |
| Z36 (Ref) | DBU | 0.55 g | 3.8 | 48.8 | 58.1 | 19% | 2 h 7' | 2 h 35' |
| Z37 (Ref) | TMG | 0.42 g | 3.8 | 44.5 | 53.4 | 20% | >12 h | >12 h |

[1]mmol of amidine or guanidine groups per 100 g of polyether containing silane groups.
[2]for 7 days at 60° C. in a closed container.
[3]as a solution (40% by wt.) in N-ethylpyrrolidone.

TABLE 4

| Comp. | Surface after 24 h | Tensile strength | Elongation at break | Modulus of elasticity 0-5% | Modulus of elasticity 0-50% |
|---|---|---|---|---|---|
| Z27 | slightly tacky | 0.52 MPa | 129% | 0.39 MPa | 0.43 MPa |
| Z28 | dry | 0.67 MPa | 160% | 0.86 MPa | 0.52 MPa |
| Z29 | dry | 0.67 MPa | 167% | 0.81 MPa | 0.49 MPa |
| Z30 | dry | 0.57 MPa | 135% | 0.67 MPa | 0.48 MPa |
| Z31 | almost dry | 0.59 MPa | 241% | 0.31 MPa | 0.31 MPa |
| Z32 | almost dry | 0.50 MPa | 194% | 0.31 MPa | 0.30 MPa |
| Z33 | almost dry | 0.54 MPa | 225% | 0.30 MPa | 0.29 MPa |
| Z34 | almost dry | 0.60 MPa | 233% | 0.30 MPa | 0.30 MPa |
| Z35 | almost dry | 0.56 MPa | 129% | 0.68 MPa | 0.50 MPa |
| Z36 (Ref) | greasy, highly tacky | 0.43 MPa | 157% | 0.28 MPa | 0.28 MPa |
| Z37 (Ref) | very highly tacky | n.d. | n.d. | n.d. | n.d. | n.d. = not determined/not measurable.

Compositions Z38 to Z42:

In a planetary mixer, 30.8 g of polymer STP-1, 25.7 g of ground chalk (Omyacarb® 5 GU, from Omya), 25.7 g of precipitated chalk (Socal® U1S2, from Solvay), 15.4 g of diisononyl cyclohexane-1,2-dicarboxylate (Hexamoll® DINCH, from BASF), 1.2 g of vinyltrimethoxysilane, 1.2 g of 3-aminopropyltrimethoxysilane and various catalysts in the amount specified according to table 5 were blended, and the mixture was tested as described for composition Z1 for skin time (ST), surface characteristics and mechanical properties. The results are shown in table 5. "Comp." stands for "composition".

TABLE 5

| Comp. | Catalyst | Amount | Concentration[1] | ST | Surface after 24 h | Tensile strength | Elongation at break | Modulus of elasticity [MPa] 0-5% | Modulus of elasticity [MPa] 0-100% |
|---|---|---|---|---|---|---|---|---|---|
| Z38 | K-1[2] | 0.19 g | 0.5 | 71' | dry | 2.0 MPa | 263% | 2.0 | 1.2 |
| Z39 | K-2[2] | 0.19 g | 0.5 | 29' | dry | 2.0 MPa | 255% | 1.9 | 1.2 |
| Z40 | K-7 | 2.99 g | 0.4 | 23' | dry | 2.0 MPa | 248% | 1.9 | 1.2 |
| Z41 | K-8 | 2.96 g | 0.4 | 22' | dry | 1.9 MPa | 275% | 1.9 | 1.1 |
| Z42 (Ref) | DBU | 0.08 g | 0.5 | 35' | greasy | 2.1 MPa | 283% | 1.8 | 1.2 |

[1] mmol of amidine or guanidine groups per 100 g of composition.
[2] as a solution (40% by wt.) in N-ethylpyrrolidone.

Compositions Z43 to Z52:

In a planetary mixer, 36.2 g of polymer STP-1, 60.2 g of ground chalk (Omyacarb® 5 GU, from Omya), 1.2 g of thixotropic paste prepared as described below, 1.2 g of vinyltrimethoxysilane, 1.2 g of 3-aminopropyltrimethoxysilane and various catalysts in the amount specified according to table 6 were blended, and the mixture was tested as described for composition Z1 for skin time (ST), surface characteristics and mechanical properties. The results are shown in table 6. "Comp." stands for "composition". The thixotropic paste was prepared by initially charging a vacuum mixer with 300 g of diisodecyl phthalate (Palatinol® Z, from BASF) and 48 g of 4,4'-methylene diphenyl diisocyanate (Desmodur® 44 MC L, from Bayer), gently heating the initial charge and then slowly adding 27 g of n-butylamine dropwise while stirring vigorously. The resultant paste was stirred for a further hour under reduced pressure while cooling.

TABLE 6

| Comp. | Catalyst | Amount | Concentration[1] | ST | Surface after 24 h | Tensile strength | Elongation at break | Modulus of elasticity [MPa] 0-5% | Modulus of elasticity [MPa] 0-100% |
|---|---|---|---|---|---|---|---|---|---|
| Z43 | K-3 | 4.83 g | 2.0 | 27' | dry | 2.7 MPa | 132% | 4.2 | 2.4 |
| Z44 | K-4 | 4.90 g | 2.0 | 15' | dry | 2.7 MPa | 118% | 4.5 | 2.5 |
| Z45 | K-5 | 5.07 g | 2.0 | 16' | dry | 2.6 MPa | 114% | 4.5 | 2.4 |
| Z46 | K-6 | 4.68 g | 2.0 | 11' | dry | 3.0 MPa | 134% | 4.6 | 2.5 |
| Z47 | K-9 | 0.18 g | 0.4 | 27' | dry | 2.9 MPa | 117% | 6.0 | 2.6 |
| Z48 | K-10 | 0.22 g | 0.4 | 31' | dry | 2.7 MPa | 91% | 6.1 | — |
| Z49 | K-11[2] | 0.18 g | 0.4 | 21' | dry | 2.4 MPa | 69% | 6.0 | — |
| Z50 | K-12[2] | 0.18 g | 0.4 | 33' | dry | 2.9 MPa | 116% | 5.9 | 2.6 |

TABLE 6-continued

| Comp. | Catalyst | Amount | Concentration[1] | ST | Surface after 24 h | Tensile strength | Elongation at break | Modulus of elasticity [MPa] 0-5% | 0-100% |
|---|---|---|---|---|---|---|---|---|---|
| Z51 | K-13 | 0.31 g | 0.4 | 25' | dry | 2.9 MPa | 104% | 5.9 | 2.7 |
| Z52 (Ref) | DBU | 0.12 g | 0.8 | 25' | slightly greasy | 2.5 MPa | 103% | 6.1 | 2.8 |

[1] mmol of amidine or guanidine groups per 100 g of composition.
[2] as a solution (40% by wt.) in N-ethylpyrrolidone.

Compositions Z53 to Z61:

In a planetary mixer, 36.2 g of polymer STP-2, 60.2 g of ground chalk (Omyacarb® 5 GU, from Omya), 1.2 g of thixotropic paste prepared as described for composition Z27, 1.2 g of vinyltriethoxysilane, 1.2 g of 3-aminopropyltriethoxysilane and various catalysts in the amount specified according to table 7 were blended, and the mixture was tested as described for composition Z1 for skin time (ST), surface characteristics and mechanical properties. The results are shown in table 7. "Comp." stands for "composition".

TABLE 7

| Comp. | Catalyst | Amount | Concentration[1] | ST | Surface after 24 h | Tensile strength | Elongation at break | Modulus of elasticity [MPa] 0-5% | 0-100% |
|---|---|---|---|---|---|---|---|---|---|
| Z53 | K-4 | 9.79 g | 4.0 | 169' | dry | 2.0 MPa | 167% | 3.1 | 1.5 |
| Z54 | K-5 | 10.13 g | 4.0 | 69' | dry | 2.1 MPa | 164% | 3.6 | 1.6 |
| Z55 | K-6 | 9.36 g | 4.0 | 125' | dry | 2.4 MPa | 180% | 3.1 | 1.7 |
| Z56 | K-9 | 1.20 g | 2.6 | 67' | s. tacky | 2.6 MPa | 108% | 4.9 | 2.5 |
| Z57 | K-10 | 1.44 g | 2.6 | 83' | s. tacky | 2.6 MPa | 127% | 4.6 | 2.3 |
| Z58 | K-11[2] | 1.19 g | 2.6 | 96' | s. tacky | 2.9 MPa | 145% | 5.0 | 2.4 |
| Z59 | K-12[2] | 1.20 g | 2.6 | 77' | s. tacky | 2.2 MPa | 106% | 6.7 | 1.9 |
| Z60 | K-13 | 2.02 g | 2.6 | 79' | s. tacky | 2.5 MPa | 127% | 5.9 | 2.2 |
| Z61 (Ref) | DBU | 0.40 g | 2.6 | 83' | slightly greasy | 2.5 MPa | 155% | 4.0 | 2.0 |

[1] mmol of amidine or guanidine groups per 100 g of polyether containing silane groups.
[2] as a solution (40% by wt.) in N-ethylpyrrolidone.
"s." stands for "slightly".

Compositions Z62 and Z63:

A composition composed of 96.0 g of GENIOSIL® STP-E 15 polyether containing silane groups (from Wacker), 0.35 g of vinyltrimethoxysilane and 3.72 g of 3-aminopropyltrimethoxysilane was blended with various catalysts in the amount specified according to table 8, and the mixture was tested as described for composition Z1 for skin time (ST), surface characteristics and mechanical properties. The results are shown in table 8. "Comp." stands for "composition".

TABLE 8

| Comp. | Catalyst | Amount | Concentration[1] | ST | Surface after 24 h | Tensile strength | Elongation at break | Modulus of elasticity 0-5% |
|---|---|---|---|---|---|---|---|---|
| Z62 | K-13 | 1.51 g | 1.9 | 23' | dry | 0.82 MPa | 60% | 1.77 MPa |
| Z63 (Ref) | DBU | 0.28 g | 1.9 | 60' | greasy | 0.72 MPa | 48% | 1.84 MPa |

[1] mmol of amidine or guanidine groups per 100 g of polyether containing silane groups.

The invention claimed is:

1. A method of crosslinking a curable composition, comprising crosslinking the curable composition with a catalyst of formula (I)

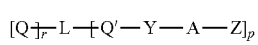

formed from a reaction of a group $L\text{-}Q_{p+r}$ and p (HX-A-Z) groups where p is an integer from 1 to 6 and r is an integer from 0 to 5, where (p+r) is an integer from 1 to 6, L is a (p+r)-valent hydrocarbyl radical having a mean molecular weight in the range from 14 to 20,000 g/mol, optionally having heteroatoms, or is a (p+r+1)-valent hydrocarbyl radical having 4 to 12 carbon atoms, which together with Q' forms an optionally substituted 5- or 6-membered ring, or is a covalent bond,
or is a hydrogen radical,
Q is a reactive group selected from epoxide, aziridine, carbonate, carboxylic anhydride, carboxylic acid, carboxylic ester, lactone, carbonyl chloride, ketone, aldehyde, 1,3-diketone, 1,3-keto ester, 1,3-keto amide, cyanate, thiocyanate, isocyanate, isothiocyanate, (meth)acrylate, (meth)acrylamide, (meth)acrylonitrile, maleate, maleamide, maleimide, fumarate, fumaramide, itaconate, itaconamide, crotonate and crotonamide,
Q' is a di- or trivalent connecting unit residue formed from the reaction of Q with HX,
Y is N or X, where X is O or S or $NR^3$ where $R^3$ is a hydrogen radical or is an alkyl or cycloalkyl or aralkyl radical which has 1 to 8 carbon atoms and optionally contains a tertiary amino group or a guanidine group,
A is a divalent hydrocarbyl radical which has 2 to 30 carbon atoms and optionally contains unsaturated components and optionally ether oxygen or secondary or tertiary amine nitrogen,
where A together with $R^3$ may also be a trivalent hydrocarbyl radical which has 5 to 10 carbon atoms and optionally contains a tertiary amine nitrogen, and
Z is a guanidine group which is bonded via a nitrogen atom and does not contain any nitrogen atom which is bonded directly to an aromatic ring or is part of a heteroaromatic ring system.

2. The method as claimed in claim 1, wherein A is either selected from the group consisting of 1,2-ethylene, 1,2-propylene, 1,3-propylene, 1,3-pentylene, 1,1-dimethyl-1,2-ethyl, 1,5-pentylene, 2-methyl-1,5-pentylene, 1,6-hexylene, 2,2(4),4-trimethyl-1,6-hexamethylene, 1,8-octylene, 1,10-decylene, 1,12-dodecylene, (1,5,5-trimethylcyclohexan-1-yl)methane-1,3, 1,3-cyclohexylenebis(methylene), 1,4-cyclohexylene-bis(methylene), 1,3-phenylenebis(methylene), 2- and/or 4-methyl-1,3-cyclohexylene, N-methyl-4-aza-1,7-heptylene, 3-oxa-1,5-pentylene, 3,6-dioxa-1,8-octylene, 4,7-dioxa-1,10-decylene and a polyoxypropylene radical having a mean molecular weight in the range from about 200 to 250 g/mol, or A together with $R^3$ including the nitrogen atom of X is a radical selected from the group consisting of piperidin-4-ylmethyl, 2-(piperidin-4-yl)ethyl and 2-piperazinoethyl.

3. The method as claimed in claim 1, wherein Z is

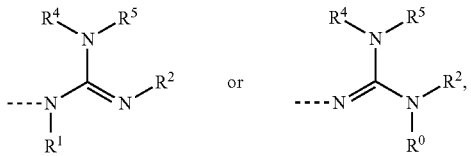

where
$R^0$ and $R^1$ are independently a hydrogen radical or an alkyl or cycloalkyl or aralkyl radical having 1 to 8 carbon atoms,
$R^2$ is a hydrogen radical or an alkyl, cycloalkyl or aralkyl radical which has 1 to 18 carbon atoms and optionally contains ether oxygen or tertiary amine nitrogen,
$R^4$ and $R^5$ are each independently a hydrogen radical or an alkyl, cycloalkyl or aralkyl radical which has 1 to 18 carbon atoms and optionally contains an ether oxygen or a tertiary amine nitrogen, where
$R^2$ and $R^0$ together may also be an alkylene radical which has 3 to 6 carbon atoms and optionally contains an ether oxygen or a tertiary amine nitrogen,
$R^4$ and $R^5$ together may also be an alkylene radical which has 4 to 7 carbon atoms and optionally contains an ether oxygen or a tertiary amine nitrogen, and
$R^2$ and $R^5$ together may also be an alkylene radical having 2 to 12 carbon atoms.

4. The method as claimed in claim 3, wherein Z is

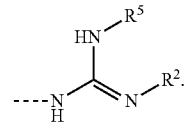

5. The method as claimed in claim 1, wherein Q' is selected from the group consisting of

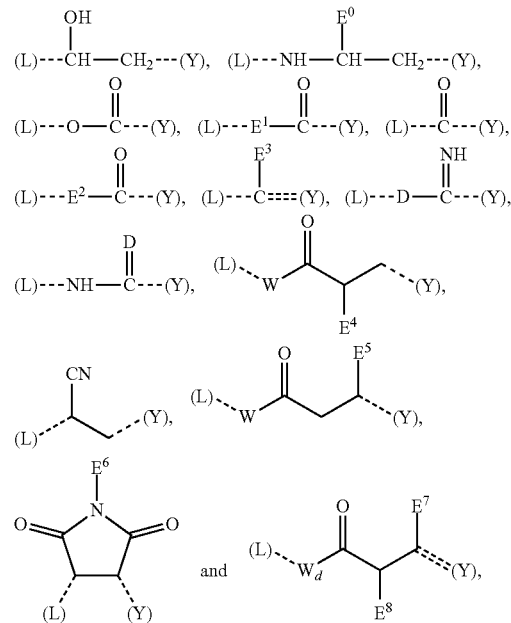

where
D is O or S,
W is O or $NR^6$ where $R^6$ is a hydrogen radical or is a monovalent hydrocarbyl radical having 1 to 8 carbon atoms,
$E^0$ is a hydrogen radical or is a methyl radical,
$E^1$ is a carboxyl-substituted alkylene, alkenediyl or phenylene radical having 2 to 8 carbon atoms,
$E^2$ is a hydroxyalkylene radical having 2 to 5 carbon atoms or is an O-bonded hydroxyalkyleneoxy radical having 2 or 3 carbon atoms,
$E^3$ is a hydrogen radical or is a monovalent hydrocarbyl radical which has 1 to 6 carbon atoms and optionally has heteroatoms in the form of ether, ester, amino or amide groups, or together with L is an optionally substituted 1,4-butylene or 1,5-pentylene radical,
$E^4$ is a hydrogen or methyl or alkoxycarbonylmethyl radical having 2 to 9 carbon atoms,
$E^5$ is an alkoxycarbonyl radical having 1 to 8 carbon atoms or is a methyl radical, $E^6$ is a hydrogen radical or is an alkyl radical having 1 to 8 carbon atoms, $E^7$ is a monovalent hydrocarbyl radical having 1 to 6 carbon atoms, $E^8$ is a hydrogen radical or is a monovalent hydrocarbyl radical having 1 to 6 carbon atoms, and d is 0 or 1.

6. The method as claimed in claim 1, wherein p is 1 or 2 or 3 and r is 0.

7. The method as claimed in claim 1, wherein the curable composition is an epoxy resin composition or a polyurethane composition or an epoxy resin/polyurethane composition or a cyanate ester resin composition or a composition containing silane groups.

8. The method as claimed in claim 1, wherein the curable composition is a composition based on polymers containing silane groups.

9. The method as claimed in claim 8, wherein the polymer containing silane groups is selected from the group consisting of polyorganosiloxanes having terminal silane groups and organic polymers containing silane groups.

10. A process for preparing a catalyst of formula (I):

 (I)

formed from a reaction of a group $L-Q_{p+r}$ and p (HX-A-Z) groups where p is an integer from 1 to 6 and r is an integer from 0 to 5, where (p+r) is an integer from 1 to 6, L is a (p+r)-valent hydrocarbyl radical having a mean molecular weight in the range from 14 to 20'000 g/mol, optionally having heteroatoms, or is a (p+r+1)-valent hydrocarbyl radical having 4 to 12 carbon atoms, which together with Q' forms an optionally substituted 5- or 6-membered ring, or is a covalent bond, or is a hydrogen radical, Q is a reactive group selected from epoxide, aziridine, carbonate, carboxylic anhydride, carboxylic acid, carboxylic ester, lactone, carbonyl chloride, ketone, aldehyde, 1,3-diketone, 1,3-keto ester, 1,3-keto amide, cyanate, thiocyanate, isocyanate, isothiocyanate, (meth)acrylate, (meth)acrylamide, (meth)acrylonitrile, maleate, maleamide, maleimide, fumarate, fumaramide, itaconate, itaconamide, crotonate and crotonamide, Q' is a di- or trivalent connecting unit residue formed from the reaction of Q with HX, Y is N or X, where X is O or S or $NR^3$ where $R^3$ is a hydrogen radical or is an alkyl or cycloalkyl or aralkyl radical which has 1 to 8 carbon atoms and optionally contains a tertiary amino group or a guanidine group, A is a divalent hydrocarbyl radical which has 2 to 30 carbon atoms and optionally contains unsaturated components and optionally ether oxygen or secondary or tertiary amine nitrogen, where A together with $R^3$ may also be a trivalent hydrocarbyl radical which has 5 to 10 carbon atoms and optionally contains a tertiary amine nitrogen, and Z is a guanidine group which is bonded via a nitrogen atom and does not contain any nitrogen atom which is bonded directly to an aromatic ring or is part of a heteroaromatic ring system, the process comprising reacting at least one guanidine of the formula (II)

 (II)

with at least one functional compound having at least one reactive group selected from epoxide, aziridine, carbonate, carboxylic anhydride, carboxylic acid, carboxylic ester, lactone, carbonyl chloride, ketone, aldehyde, 1,3-diketone, 1,3-keto ester, 1,3-keto amide, cyanate, thiocyanate, isocyanate, isothiocyanate, (meth)acrylate, (meth)acrylamide, (meth)acrylonitrile, maleate, maleamide, maleimide, fumarate, fumaramide, itaconate, itaconamide, crotonate and crotonamide.

11. A curable composition comprising at least one catalyst of formula (I)

 (I)

formed from a reaction of a group $L-Q_{p+r}$ and p (HX-A-Z) groups where p is an integer from 1 to 6 and r is an integer from 0 to 5, where (p+r) is an integer from 1 to 6, L is a (p+r)-valent hydrocarbyl radical having a mean molecular weight in the range from 14 to 20'000 g/mol, optionally having heteroatoms, or is a (p+r+1)-valent hydrocarbyl radical having 4 to 12 carbon atoms, which together with Q' forms an optionally substituted 5- or 6-membered ring, or is a covalent bond, or is a hydrogen radical, Q is a reactive group selected from epoxide, aziridine, carbonate, carboxylic anhydride, carboxylic acid, carboxylic ester, lactone, carbonyl chloride, ketone, aldehyde, 1,3-diketone, 1,3-keto ester, 1,3-keto amide, cyanate, thiocyanate, isocyanate, isothiocyanate, (meth)acrylate, (meth)acrylamide, (meth)acrylonitrile, maleate, maleamide, maleimide, fumarate, fumaramide, itaconate, itaconamide, crotonate and crotonamide, Q' is a di- or trivalent connecting unit residue formed from the reaction of Q with HX, Y is N or X, where X is O or S or $NR^3$ where $R^3$ is a hydrogen radical or is an alkyl or cycloalkyl or aralkyl radical which has 1 to 8 carbon atoms and optionally contains a tertiary amino group or a guanidine group, A is a divalent hydrocarbyl radical which has 2 to 30 carbon atoms and optionally contains unsaturated components and optionally ether oxygen or secondary or tertiary amine nitrogen, where A together with $R^3$ may also be a trivalent hydrocarbyl radical which has 5 to 10 carbon atoms and optionally contains a tertiary amine nitrogen, and Z is a guanidine group which is bonded via a nitrogen atom and does not contain any nitrogen atom which is bonded directly to an aromatic ring or is part of a heteroaromatic ring system.

12. The composition as claimed in claim 11, further comprising at least one polymer containing silane groups.

13. The composition as claimed in claim 12, wherein the polymer containing silane groups is a polyorganosiloxane having terminal silane groups.

14. The composition as claimed in claim 12, wherein the polymer containing silane groups is an organic polymer containing silane groups.

15. The composition as claimed claim 11, wherein it is an adhesive or a sealant or a coating.

* * * * *